United States Patent
Shi et al.

(10) Patent No.: US 12,226,500 B2
(45) Date of Patent: Feb. 18, 2025

(54) METHOD FOR SUPPRESSING ADHESION OF AIR HARMFUL SUBSTANCES

(71) Applicant: KAO CORPORATION, Tokyo (JP)

(72) Inventors: Jia Shi, Sumida-ku (JP); Tomoya Fujii, Sumida-ku (JP); Hiroyuki Takizawa, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 545 days.

(21) Appl. No.: 17/616,455

(22) PCT Filed: Jun. 4, 2020

(86) PCT No.: PCT/JP2020/022176
§ 371 (c)(1),
(2) Date: Dec. 3, 2021

(87) PCT Pub. No.: WO2020/246556
PCT Pub. Date: Dec. 10, 2020

(65) Prior Publication Data
US 2022/0249339 A1     Aug. 11, 2022

(30) Foreign Application Priority Data

| Jun. 6, 2019 | (JP) | 2019-106338 |
| Jun. 6, 2019 | (JP) | 2019-106339 |
| Jun. 6, 2019 | (JP) | 2019-106343 |
| Jun. 6, 2019 | (JP) | 2019-106344 |

(51) Int. Cl.
| A61K 8/19 | (2006.01) |
| A61K 8/27 | (2006.01) |
| A61K 8/29 | (2006.01) |
| A61K 8/31 | (2006.01) |
| A61K 8/37 | (2006.01) |
| A61K 8/89 | (2006.01) |
| A61K 8/891 | (2006.01) |
| A61Q 17/00 | (2006.01) |
| B82Y 5/00 | (2011.01) |

(52) U.S. Cl.
CPC .............. *A61K 8/27* (2013.01); *A61K 8/29* (2013.01); *A61K 8/891* (2013.01); *A61Q 17/00* (2013.01); *A61K 2800/413* (2013.01); *A61K 2800/61* (2013.01); *B82Y 5/00* (2013.01)

(58) Field of Classification Search
None
See application file for complete search history.

(56) References Cited

U.S. PATENT DOCUMENTS

| 6,316,012 B1 | 11/2001 | N'Guyen et al. |
| 2002/0016433 A1 | 2/2002 | Keller et al. |
| 2004/0126341 A1* | 7/2004 | Pauly .............. A61K 8/64 424/59 |
| 2006/0002866 A1 | 1/2006 | Gilles et al. |
| 2007/0184270 A1 | 8/2007 | Higashi et al. |
| 2010/0135938 A1 | 6/2010 | Ishikubo et al. |
| 2010/0297039 A1 | 11/2010 | Ishikubo et al. |
| 2014/0092804 A1 | 4/2014 | Scott |
| 2014/0348765 A1 | 11/2014 | Sasaki |
| 2017/0165154 A1 | 6/2017 | Ashida et al. |
| 2017/0202758 A1 | 7/2017 | Nagare et al. |

FOREIGN PATENT DOCUMENTS

| CN | 101312706 A | 11/2008 |
| CN | 101674798 A | 3/2010 |
| CN | 101686907 A | 3/2010 |
| CN | 104168882 A | 11/2014 |
| CN | 104780900 A | 7/2015 |
| CN | 106456512 A | 2/2017 |
| EP | 2 921 162 A1 | 9/2015 |
| JP | 6-227961 A | 8/1994 |
| JP | 2001-235896 A | 8/2001 |
| JP | 2002-38102 A | 2/2002 |

(Continued)

OTHER PUBLICATIONS

International Search Report issued Aug. 4, 2020 in PCT/JP2020/022176 (with English translation), 4 pages.
Manabu Shiraiwa, et al. "The Role of Long-Lived Reactive Oxygen Intermediates in the Reaction of Ozone with Aerosol Particles" Nature Chemistry, vol. 3, Apr. 2011, pp. 291-295.
Extended European Search Report issued Jun. 27, 2023 in European Application 20819567.7, 8 pages.
"Personal Care Catalog," Momentive Performance Materials Inc., Jun. 2015, 5 pages (with unedited computer-generated English translation).
U.S. Appl. No. 17/616,511, filed Dec. 3, 2021, Hiroyuki Takizawa, et al.
U.S. Appl. No. 17/616,529, filed Dec. 3, 2021, Tomoya Fujii, et al.

*Primary Examiner* — Brian Gulledge
(74) *Attorney, Agent, or Firm* — Oblon, McClelland, Maier & Neustadt, L.L.P.

(57) ABSTRACT

Disclosed are: a method for suppressing adhesion of air harmful substances, including applying a metal oxide (A) having an average primary particle diameter $d_A$ of 800 nm or less to skin in an amount of 0.03 mg/cm$^2$ or more to suppress adhesion of air pollutants to the skin, and a method for suppressing adhesion of air pollutants, including applying an external preparation to skin to suppress adhesion of air pollutants to the skin, wherein the external preparation contains the component (AI), and the component (BI), the component (BII) or the component (BIII), and the ratio by mass of the content of the component (BI), the component (BII) or the component (BIII) to the content of the component (AI) in the external preparation each falls within a specific range. Component (AI): a hydrophobized metal oxide having an average primary particle diameter $d_{AI}$ of 800 nm or less. Component (BI): an ester oil. Component (BII): a nonvolatile hydrocarbon oil. Component (BIII): a nonvolatile silicone oil.

17 Claims, 2 Drawing Sheets

(56) References Cited

FOREIGN PATENT DOCUMENTS

| | | | |
|---|---|---|---|
| JP | 2002-114663 A | 4/2002 | |
| JP | 2004-238788 A | 8/2004 | |
| JP | 2005-68028 A | 3/2005 | |
| JP | 2005-336056 A | 12/2005 | |
| JP | 2006-8980 A | 1/2006 | |
| JP | 2006-510679 A | 3/2006 | |
| JP | 2007-210903 A | 8/2007 | |
| JP | 2009-13543 A | 1/2009 | |
| JP | 2010-1260 A | 1/2010 | |
| JP | 2013 107887 * | 6/2013 | ............. A61Q 19/00 |
| JP | 2013-107887 A | 6/2013 | |
| JP | 2015-229643 A | 12/2015 | |
| JP | 2017-122076 A | 7/2017 | |
| JP | 2017-190299 A | 10/2017 | |
| JP | 6227961 B2 | 11/2017 | |
| JP | 2019-64966 A | 4/2019 | |
| JP | 2019-81803 A | 5/2019 | |
| JP | WO 2019/098134 A1 | 5/2019 | |
| KR | 10-1659456 B1 | 9/2016 | |
| KR | 10-2018-0006536 A | 1/2018 | |
| KR | 10-2018-0012909 A | 2/2018 | |
| TW | 201625203 A | 7/2016 | |
| WO | WO 2014/136993 A2 | 9/2014 | |

* cited by examiner

METHOD FOR SUPPRESSING ADHESION OF AIR HARMFUL SUBSTANCES

FIELD OF THE INVENTION

The present invention relates to a method for suppressing adhesion of air harmful substances.

BACKGROUND OF THE INVENTION

Recently, harmful substances floating in air such as pollens of cedar and Japanese cypress, air pollutants such as smoke and dust, and yellow sand (hereinafter also referred to as "air harmful substances") have become problematic because they cause various health harm to the human body. Among air harmful substances, particulate matters having a diameter of 2.5 μm or less, called PM 2.5, are composed of a carbon material, a sulfate, a nitrate, an ammonium salt, etc., as constituent components, and it is known that PM 2.5 and yellow sand cause diseases of circulatory system and respiratory systems by inhalation. In addition, it is pointed out that PM 2.5 as well as yellow sand and pollens adhere to or penetrate through skin to cause skin troubles. For example, Nature Chemistry, 3, 291-295 (2011) by Shiraiwa, et al. (NPL 1) discloses an academic report relating to PM 2.5 that causes damage to skin. Consequently, demands for cosmetic materials capable of protecting skin from air harmful substances have increased.

For example, WO2014/136993 (PTL 1) describes a skincare cosmetic material containing a specific amount of magnesium metasilicate aluminate and a specific amount of a UV protectant, as a skin-care cosmetic material capable of protecting skin from external stimulations such as air pollutants.

SUMMARY OF THE INVENTION

The present invention relates to the following [1] to [4].

[1] A method for suppressing adhesion of air harmful substances, including applying a metal oxide (A) having an average primary particle diameter $d_A$ of 800 nm or less to skin in an amount of 0.03 mg/cm² or more to suppress adhesion of air harmful substances to the skin.

[2] A method for suppressing adhesion of air harmful substances, including applying an external preparation to skin to suppress adhesion of air harmful substances to the skin, wherein:
the external preparation contains the following component (AI) and component (BI), and the ratio by mass of the content of the component (BI) to the content of the component (AI) in the external preparation [(BI)/(AI)] is 9 or less:
Component (AI): a hydrophobized metal oxide having an average primary particle diameter $d_{AI}$ of 800 nm or less,
Component (BI): an ester oil.

[3] A method for suppressing adhesion of air harmful substances, including applying an external preparation to skin to suppress adhesion of air harmful substances to the skin, wherein:
the external preparation contains the following component (AI) and component (BII), and the ratio by mass of the content of the component (BII) to the content of the component (AI) in the external preparation [(BII)/(AI)] is 3.5 or less:
Component (AI): a hydrophobized metal oxide having an average primary particle diameter $d_{AI}$ of 800 nm or less,
Component (BII): a nonvolatile hydrocarbon oil.

[4] A method for suppressing adhesion of air harmful substances, including applying an external preparation to skin to suppress adhesion of air harmful substances to the skin, wherein:
the external preparation contains the following component (AI) and component (BIII), and the ratio by mass of the content of the component (BIII) to the content of the component (AI) in the external preparation [(BIII)/(AI)] is 0.85 or less:
Component (AI): a hydrophobized metal oxide having an average primary particle diameter $d_{AI}$ of 800 nm or less,
Component (BIII): a nonvolatile silicone oil.

DETAILED DESCRIPTION OF THE INVENTION

Figure 1:
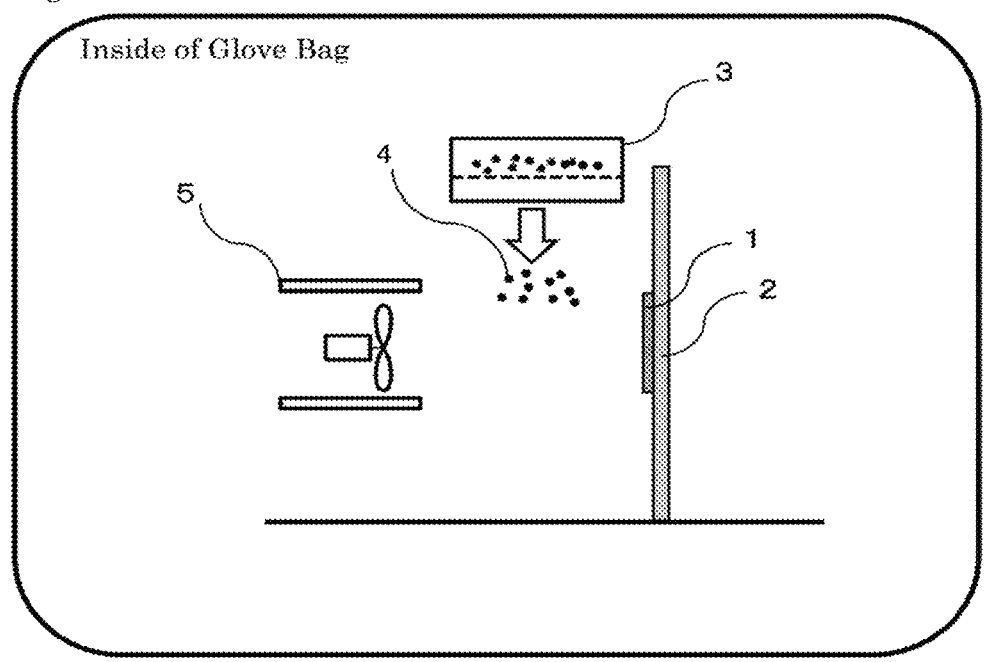
FIG. 1 is an outline view showing an evaluation method for the effect of suppressing adhesion of air harmful substances.
Figure 2:
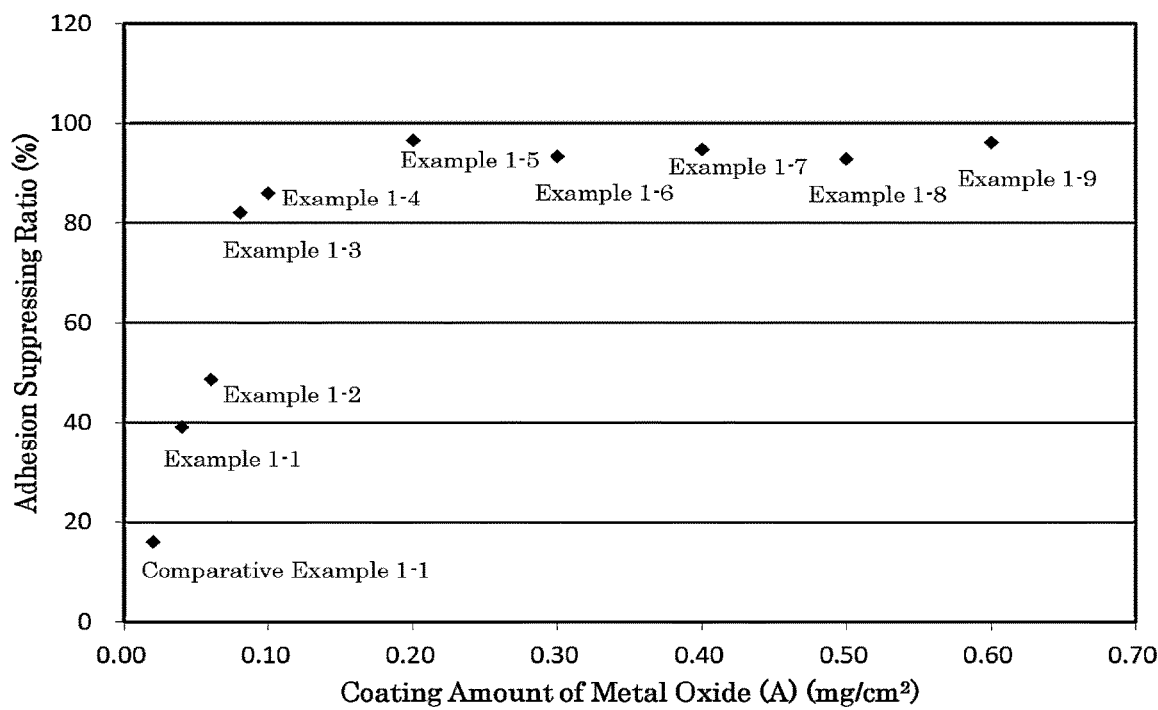
FIG. 2 is a view showing the results of air harmful substances adhesion suppressing ratio relative to the coating amount of the metal oxide (A) in Examples 1-1 to 1-9 and Comparative Example 1-1.

PTL 1 describes that, according to the technique therein, magnesium metasilicate aluminate adsorbs air pollutants by the adsorption performance thereof to prevent them from reaching skin and, in addition, even when acid substances adhere to skin, magnesium metasilicate aluminate can neutralize them by the pH buffering capability thereof, and accordingly skin damage due to these external stimulations can be thereby relieved. In addition, it also describes that a UV protectant can effectively protect skin from UV rays. According to the technique, influences of air pollutants on skin can be reduced but air pollutants cannot be prevented from adhering to skin, and there is room for improvement. In the case where an inorganic powder is blended in an external preparation, users may have a bad feel such as grating in applying the external preparation to the skin. Consequently, a good feel in use by application to skin is also desired.

The present invention relates to a method for suppressing adhesion of air harmful substances capable of effectively suppressing adhesion of air harmful substances to skin.

The present invention also relates to a method for suppressing adhesion of air harmful substances capable of securing a good feel in use in application an external preparation to skin, and capable of effectively suppressing adhesion of air harmful substances to skin.

The present inventors have noted that, not by adsorbing air pollutants as shown in PTL 1, but by applying a specific amount of a metal oxide having a specific average primary particle diameter to skin to form nano-size irregularities on the surface of the skin, adhesion of air harmful substances to skin can be suppressed, and have found out a possibility of providing a method for suppressing adhesion of air harmful substances.

In addition, the present inventors have also noted that, not by adsorbing air pollutants as shown in PTL 1, but by applying an external preparation that contains a hydrophobized metal oxide having an average primary particle diameter falling within a specific range, and an ester oil, a nonvolatile hydrocarbon oil or a nonvolatile silicone oil each in a specific ratio by mass, to skin to form nano-size irregularities on the surface of the skin without worsening the feel in application thereof to thereby suppress adhesion of air harmful substances to skin, and have found out a possibility of providing a method for suppressing adhesion of air harmful substances.

Specifically, the present invention relates to the following aspects [1] to [4].

[1] A method for suppressing adhesion of air harmful substances, including applying a metal oxide (A) having an average primary particle diameter $d_A$ of 800 nm or less to skin in an amount of 0.03 mg/cm² or more to suppress adhesion of air harmful substances to the skin (hereinafter referred to as "the first aspect of the invention").

[2] A method for suppressing adhesion of air harmful substances, including applying an external preparation to skin to suppress adhesion of air harmful substances to the skin, wherein:
the external preparation contains the following component (AI) and component (BI), and the ratio by mass of the content of the component (BI) to the content of the component (AI) in the external preparation [(BI)/(AI)] is 9 or less (hereinafter referred to as "the second aspect of the invention"):
Component (AI): a hydrophobized metal oxide having an average primary particle diameter $d_{AI}$ of 800 nm or less,
Component (BI): an ester oil.

[3] A method for suppressing adhesion of air harmful substances, including applying an external preparation to skin to suppress adhesion of air harmful substances to the skin, wherein:
the external preparation contains the following component (AI) and component (BII), and the ratio by mass of the content of the component (BII) to the content of the component (AI) in the external preparation [(BII)/(AI)] is 3.5 or less (hereinafter referred to as "the third aspect of the invention"):
Component (AI): a hydrophobized metal oxide having an average primary particle diameter $d_{AI}$ of 800 nm or less,
Component (BI): a nonvolatile hydrocarbon oil.

[4] A method for suppressing adhesion of air harmful substances, including applying an external preparation to skin to suppress adhesion of air harmful substances to the skin, wherein:
the external preparation contains the following component (AI) and component (BIII), and the ratio by mass of the content of the component (BIII) to the content of the component (AI) in the external preparation [(BIII)/(AI)] is 0.85 or less (hereinafter referred to as "the fourth aspect of the invention"):
Component (AI): a hydrophobized metal oxide having an average primary particle diameter $d_{AI}$ of 800 nm or less,
Component (BI): a nonvolatile silicone oil.

According to the method of the first aspect of the invention, adhesion of air harmful substances to skin can be effectively suppressed.

Also according to the methods of the second to fourth aspects of the invention, the external preparation can give a good feel to users who use by application thereof to skin, and can effectively suppress adhesion of air harmful substances to skin.

In the present invention, "air harmful substances" mean harmful substances (including PM 2.5) floating in air, such as pollens of cedar and Japanese cypress; air pollutants such as particles containing soot and smoke containing such as sulfur oxide, soot and dust, and nitrogen oxides, powder dust, motor exhaust, hazardous air pollutants such as benzene, trichloroethylene, and tetrachloroethylene, and volatile organic compounds (VOC), etc.; and yellow sand.

Also in the present invention, "hydrophobized metal oxide" means a metal oxide whose surface has been hydrophobized.

In the following description, the effect of suppressing adhesion of air harmful substances in the present invention is expressed simply as "adhesion suppressing effect".

The adhesion suppressing method of the first aspect of the present invention provides a high adhesion suppressing effect against air harmful substances, especially fine particulate air harmful substances. Though not clear, the reason may be considered to be because, in the first aspect of the invention, a specific amount of a metal oxide having an average primary particle diameter falling within a specific range is applied to skin to form nano-size irregularities on the surface of the skin, and accordingly, the contact area between air harmful substances and the metal oxide in contact thereof can be reduced and adhesion of the air harmful substances can be thereby effectively suppressed.

The adhesion suppressing methods of the second to fourth aspects of the invention provides a good feel to users who use by application to skin, and provides a high adhesion suppressing effect against air harmful substances, especially fine particulate air harmful substances. The reason why the aforementioned advantageous effects can be attained is considered as follows though it is not clearly determined yet.

In the second to fourth aspects of the invention, a metal oxide having an average primary particle diameter falling within a specific range and having been hydrophobized on the surface thereof is applied to skin, and accordingly, nano-size irregularities are formed on the surface of the skin so as to reduce the contact area between air harmful substances and the metal oxide in contact thereof to thereby effectively suppress adhesion of air harmful substances.

In addition, the external preparations for use in the second to fourth aspects of the invention each contain a hydrophobized metal oxide, and an ester oil, a nonvolatile hydrocarbon oil or a nonvolatile silicone oil as an oily agent each in a specific ratio by mass, and therefore it is considered that the external preparations can express a good feel in use by the lubricating effect of the ester oil, the nonvolatile hydrocarbon oil or the nonvolatile silicone oil, without interfering with the adhesion suppressing effect against air harmful substances. Further, the hydrophobized metal oxide can smoothly spread on the surface of skin along with the ester oil, the nonvolatile hydrocarbon oil or the nonvolatile silicone oil, and is therefore considered to also contribute toward giving a good feel in use.

[Adhesion Suppressing Method Against Air Harmful Substances: First Aspect of Invention]

The adhesion suppressing method against air harmful substances of the first aspect of the invention includes applying a metal oxide (A) having an average primary particle diameter $d_A$ of 800 nm or less to skin in an amount of 0.03 mg/cm² or more to suppress adhesion of air harmful substances to the skin.

<Metal Oxide (A)>

The average primary particle diameter $d_A$ of the metal oxide (A) is, from the viewpoint of improving the adhesion suppressing effect, 800 nm or less, preferably 500 nm or less, more preferably 300 nm or less, even more preferably 200 nm or less, further more preferably 80 nm or less, further more preferably 50 nm or less, and is, from the viewpoint of general versatility, preferably 5 nm or more, more preferably 10 nm or more. More specifically, the average primary particle diameter $d_A$ is, from the viewpoint of improving the adhesion suppressing effect and from the viewpoint of general versatility, preferably 5 to 800 nm, more preferably 5 to 500 nm, even more preferably 5 to 300 nm, further more preferably 5 to 200 nm, further more preferably 5 to 80 nm, further more preferably 5 to 50 nm, further more preferably 10 to 50 nm.

The average primary particle diameter $d_A$ in the first aspect of the invention can be determined on the observation image with a transmission electron microscope (TEM). Specifically, the particles are observed with TEM under the condition of an observation magnification power of 50,000 times, the maximum minor diameters of 300 primary particles on the observation image are measured, and the data are averaged to give a number-average value. Here, the maximum minor diameter means a minor diameter having a maximum length of minor diameters perpendicular to major diameter in the case where the metal oxide (A) has a shape different from a tabular one. In the case where the metal oxide (A) is a tabular one, the thicknesses of 300 primary particles in the image observed under the same condition as above are measured, and the data are averaged to give a number-average value. Specifically, the average primary particle diameter is measured according to the method described in the section of Examples.

The metal oxide (A) is not particularly limited as long as it can be generally used in external preparations such as cosmetic materials. Specific examples of the metal oxide (A) include titanium oxide, zinc oxide, cerium oxide, aluminum oxide (alumina), magnesium oxide, calcium oxide, zirconium oxide, iron oxide, and chromium oxide. Among these, from the viewpoint of giving UV protecting performance, preferred are at least one selected from the group consisting of titanium oxide, zinc oxide and cerium oxide, and more preferred are at least one selected from the group consisting of titanium oxide and zinc oxide.

In the case where the metal oxide (A) is titanium oxide, the crystal structure of titanium oxide may be any of an anatase-type, rutile-type or Brookite-type one, but is, from the viewpoint of general versatility, preferably a rutile-type or anatase-type one.

The shape of the metal oxide (A) includes spherical, spindle-shaped, tabular and vesicular ones. Among these, from the viewpoint of improving the adhesion suppressing effect, a spherical, spindle-shaped or tabular one is preferred.

In the case where the metal oxide (A) is titanium oxide, preferably it is a spindle-shaped one from the viewpoint of improving the adhesion suppressing effect.

In the case where the metal oxide (A) is zinc oxide, preferably it is a spherical or tabular one from the viewpoint of improving the adhesion suppressing effect.

The existence form of the metal oxide (A) may be in a form of primary particles or may also be in a form containing aggregates formed by aggregating primary particles (secondary particles), so far as the average primary particle diameter $d_A$ thereof satisfies the above-mentioned range.

The metal oxide (A) may be one whose surface is not treated, or may also be a surface-treated one, but from the viewpoint of enhancing the dispersibility of the metal oxide (A) in use in external preparations such as cosmetic materials to thereby improve the adhesion suppressing effect thereof, preferred is a surface-treated one. The surface treatment includes a hydrophobizing treatment and a hydrophilizing treatment.

The hydrophobizing treatment includes a silicone treatment; an alkylalkoxysilane treatment; a fatty acid treatment; a fluorine-containing compound treatment with a perfluoroalkyl phosphate, a perfluoroalcohol or a perfluoroalkylalkoxysilane; an amino acid treatment with an N-acylglutamic acid; and an alkyl phosphate treatment.

Among these, from the viewpoint of enhancing the dispersibility of the metal oxide (A) in cosmetic materials to improve the adhesion suppressing effect, a silicone treatment, an alkylalkoxysilane treatment and a fatty acid treatment are preferred.

The surface treatment agent for use in the silicone treatment includes various silicone oils such as methylpolysiloxane, dimethylpolysiloxane, methylphenylpolysiloxane, methylhydrogen polysiloxane, methylcyclopolysiloxane, dodecamethylcyclohexasiloxane, tetradecamethylhexasiloxane, dimethylsiloxane/methyl(polyoxyethylene)siloxane/ methyl(polyoxypropylene)siloxane copolymer, dimethylsiloxane/methyl(polyoxyethylene)siloxane copolymer, dimethylsiloxane/methyl(polyoxypropylene)siloxane copolymer, dimethylsiloxane/methylcetyloxysiloxane copolymer, dimethylsiloxane/methylstearoxysiloxane copolymer, and alkyl acrylate/dimethicone copolymer. Among these, from the viewpoint of enhancing the dispersibility of the metal oxide (A) in cosmetic materials to improve the adhesion suppressing effect, preferred are methylhydrogen polysiloxane and dimethylpolysiloxane.

The surface treatment agent for use in the alkylalkoxysilane treatment is, from the viewpoint of enhancing the dispersibility of the metal oxide (A) in cosmetic materials to improve the adhesion suppressing effect, preferably one having a linear or branched alkyl group having 6 or more and 20 or less carbon atoms, more preferably octyltriethoxysilane or octyltrimethoxysilane.

The surface treatment agent for use in the fatty acid treatment includes a linear or branched fatty acid having 12 or more and 22 or less carbon atoms. Above all, from the viewpoint of enhancing the dispersibility of the metal oxide (A) in cosmetic materials to improve the adhesion suppressing effect, preferred is a linear or branched higher fatty acid having 14 or more and 22 or less carbon atoms, even more preferred is a linear or branched high fatty acid having 16 or more and 20 or less carbon atoms, and even more preferred are stearic acid and isostearic acid.

Commercial products of the hydrophobized metal oxide (A) include "JR-800S" (silicone-treated titanium oxide), "MPY-70M" (silicone-treated titanium oxide), "MZ-504R3M" (silicone-treated zinc oxide), "MT-600KS" (silicone-treated zinc oxide), "MT-100TV" (stearic acid-treated titanium oxide), and "MT-100Z" (stearic acid-treated titanium oxide) all by Tayca Corporation; "MPT-171" (stearic acid-treated titanium oxide) by Ishihara Sangyo Kaisha Ltd.; "D-FZN" (silicone-treated zinc oxide) by Daito Kasei Corporation; "STR-100A-LP" (silicone-treated titanium oxide), "FINEX-50-LPTM" (silicone-treated zinc oxide), "FINEX-30-OTS" (octyltriethoxysilane-treated zinc oxide), "STR-100C-LF" (stearic acid-treated titanium oxide), "STR-100W-OTS" (octyltriethoxysilane-treated titanium oxide" and "FINEX-50-OTS" (octyltriethoxysilane-treated zinc oxide) all by Sakai Chemical Industry Co., Ltd.

The hydrophilizing treatment includes a treatment with hydrous silica; a hydrous oxide, an oxide or a hydroxide of a metal such as aluminum or zirconia; a water-soluble polymer such as a polyacrylic acid, alginic acid or a salt thereof. Among these, at least one selected from the group consisting of a hydrous silica treatment and an aluminum hydroxide treatment are preferred.

Commercial products of the hydrophilized metal oxide (A) include "MT-100WP" (hydrous silica-treated titanium oxide" by Tayca Corporation; and "STR-100W" (hydrous silica-treated titanium oxide), "STR-100C" (aluminum hydroxide-treated titanium oxide) and "FINEX-33W" (hydrous silica-treated zinc oxide) all by Sakai Chemical Industry Co., Ltd.

One alone or two or more kinds of the above-mentioned surface treatment agents can be used either singly or as combined.

The treatment amount of hydrophobizing treatment or hydrophilizing treatment is, from the viewpoint of enhancing the dispersibility of the metal oxide (A) in cosmetic materials to improve the adhesion suppressing effect, preferably 0.1% by mass or more, and is preferably 40% by mass or less, more preferably 30% by mass or less, on the basis of the metal oxide (A).

In the case where the metal oxide (A) is hydrophobized or hydrophilized on the surface thereof, the mass, the coating amount and the average primary particle diameter $d_A$ of the metal oxide (A) mean the mass, the coating amount and the average primary particle diameter $d_A$ thereof, respectively, including the surface treatment agent.

In the case where the metal oxide (A) is titanium oxide, the $TiO_2$ content in titanium oxide is, from the viewpoint of improving the adhesion suppressing effect, preferably 60% by mass or more, more preferably 70% by mass or more, and is preferably 100% by mass or less.

In the case where the metal oxide (A) is zinc oxide, the ZnO content in zinc oxide is, from the viewpoint of improving the adhesion suppressing effect, preferably 60% by mass or more, more preferably 70% by mass or more, and is preferably 100% by mass or less.

From the viewpoint of enhancing the dispersibility of the metal oxide (A) in cosmetic materials to improve the adhesion suppressing effect, the metal oxide (A) is preferably hydrophobized or hydrophilized on the surface thereof, more preferably hydrophobized on the surface thereof, and is even more preferably at least one selected from the group consisting of a titanium oxide that has been hydrophobized (hereinafter referred to as "a hydrophobized titanium oxide") and a zinc oxide that has been hydrophobized (hereinafter referred to as "a hydrophobized zinc oxide"), further more preferably at least one selected from the group consisting of a silicone-treated titanium oxide, a silicone-treated zinc oxide, a fatty acid-treated titanium oxide, a fatty acid-treated zinc oxide, an alkylalkoxysilane-treated titanium oxide and an alkylalkoxysilane-treated zinc oxide, further more preferably at least one selected from the group consisting of a silicone-treated titanium oxide, a silicone-treated zinc oxide, a fatty acid-treated titanium oxide and an alkylalkoxysilane-treated zinc oxide.

In the method of applying the metal oxide (A) to skin in the first aspect of the invention, the metal oxide (A) may be directly applied thereto not using a solvent, but depending on the mode of use and the intended object, a solvent, an oily agent and additives that are generally used in external preparations such as cosmetic materials can be appropriately blended therein before application. Here, "applying to skin" includes not only direct application of the metal oxide (A) to the surface of skin by hand or the like, but also adhesion of the metal oxide (A) to the surface of skin by spraying or the like.

In the first aspect of the invention, from the viewpoint of improving the uniformity of the coating film in applying to skin to improve the adhesion suppressing effect, preferably, the metal oxide (A) is previously mixed by stirring with a solvent or an oily agent to be dispersed in the solvent or the oily agent, and then applied to skin.

The solvent that is used in applying the metal oxide (A) to skin includes a monohydric or polyhydric alcohol having 1 or more and 6 or less carbon atoms, such as ethanol, glycerin, 1,3-butylene glycol, propylene glycol, and sorbitol. Above all, from the viewpoint of general versatility, ethanol is preferably contained.

The blending amount of the solvent is, in terms of a ratio by mass of the metal oxide (A) to the solvent [metal oxide (A)/solvent], from the viewpoint of improving the adhesion suppressing effect, preferably 0.02 or more, more preferably 0.03 or more, even more preferably 0.04 or more, and is preferably 1 or less, more preferably 0.7 or less, even more preferably 0.5 or less.

The oily agent that is used in applying the metal oxide (A) to skin is preferably a volatile oil.

"Volatility" in this description means that the amount of evaporation for 6 hours at 25° C., as measured according to the following method, is more than 20%.

Measurement method: A piece of filter paper having a diameter of 90 mm is put in a glass dish having a diameter of 120 mm, 1 g of a sample is put in the filter paper, and stored in room (25° C.) at 65% RH for 6 hours. The mass of the sample before and after storage is measured, and the amount of evaporation is calculated according to the following formula.

Amount of evaporation (%)=(mass of sample before storage−mass of sample after storage)/(mass of sample before storage)×100

The volatile oil includes a volatile silicone oil, and a volatile hydrocarbon oil.

The volatile silicone oil in the first aspect of the invention is preferably a silicone oil having a kinematic viscosity at 25° C. of less than 5 mm$^2$/s. The kinematic viscosity at 25° C. can be measured with a Ubellohde's viscometer according to ASTM D 445-46T or JIS Z 8803.

The volatile silicone oil includes a linear organopolysiloxane and a cyclic organopolysiloxane.

Specific examples of the linear organopolysiloxane include octamethyltrisiloxane, decamethyltetrasiloxane, dodecamethylpentasiloxane, and 1,1,1,3,5,5,5-heptamethyl-3-[(trimethylsilyl)oxy]-trisiloxane.

The cyclic organopolysiloxane includes a 4- to 6-membered cyclic siloxane having an alkyl group with 1 or more and 5 or less carbon atoms as a substituent, and specific examples thereof include octamethylcyclotetrasiloxane, and decamethylcyclopentasiloxane.

Commercial products of the volatile silicone oil include "KF-96A-1cs" (octamethyltrisiloxane), "KF-96L-1.5cs" (decamethyltetrasiloxane), "KF-96L-2cs" (dodecamethylpentasiloxane", "KF-995" (decamethylcyclopentasiloxane), and "TMF-1.5" (1,1,1,3,5,5,5-heptamethyl-3-[(trimethylsilyl)oxy]-trisiloxane) all by Shin-Etsu Chemical Industry Co., Ltd.; "SH200C Fluid 1cs" (octamethyltrisiloxane), "SH200C Fluid 1.5cs" (decamethyltetrasiloxane), "SH200C Fluid 2cs" (dodecamethylpentasiloxane), and "SH245 Fluid" (decamethylcyclopentasiloxane) all by Toray Dow Corning Corporation; and "TSF405" (decamethylcyclopentasiloxane) by Momentive Performance Materials Corporation.

The volatile hydrocarbon oil in the first aspect of the invention is preferably a saturated or unsaturated hydrocarbon oil having 8 or more and 16 or less carbon atoms, and examples thereof include a paraffinic hydrocarbon oil such as n-decane, n-undecane and n-dodecane; an isoparaffinic hydrocarbon oil such as isodecane, isododecane, and hydrogenated polyisobutene (light liquid isoparaffin); and a cycloparaffinic hydrocarbon oil such as cyclodecane and cyclododecane.

The blending amount of the oily agent is, in terms of a ratio by mass of the metal oxide (A) to the oily agent [metal oxide (A)/oily agent], from the viewpoint of improving the adhesion suppressing effect, preferably 0.02 or more, more preferably 0.03 or more, even more preferably 0.04 or more, and is preferably 1 or less, more preferably 0.7 or less, even more preferably 0.5 or less.

The coating amount of the metal oxide (A) on the surface of skin is, from the viewpoint of improving the adhesion suppressing effect, 0.03 mg/cm$^2$ or more, preferably 0.04 mg/cm$^2$ or more, more preferably 0.05 mg/cm$^2$ or more, even more preferably 0.07 mg/cm$^2$ or more, further more preferably 0.10 mg/cm$^2$ or more, further more preferably 0.15 mg/cm$^2$ or more, and is, from the viewpoint of economy and feel in use as external preparations, preferably 0.8 mg/cm$^2$ or less, more preferably 0.7 mg/cm$^2$ or less. More specifically, the coating amount of the metal oxide (A) on the surface of skin is, from the viewpoint of improving the adhesion suppressing effect and also from the viewpoint of economy and feel in use as external preparations, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.10 to 0.8 mg/cm$^2$, further more preferably 0.15 to 0.8 mg/cm$^2$, further more preferably 0.15 to 0.7 mg/cm$^2$.

In the first aspect of the invention, the metal oxide (A) can be used by blending in external preparations that are applied to, for example, skin and hair. The external preparations are, from the viewpoint of the adhesion suppressing effect, preferably cosmetic materials, more preferably skin cosmetic materials.

The form of the external preparation for the first aspect of the invention incudes a water-based type having one aqueous phase as a dispersion medium, an oil-based type having one oily phase as a dispersion medium, an oil-in-water type (O/W type), and a water-in-oil type (W/O type), and these can be appropriately selected.

The preparation form of the external preparation is not specifically limited, and may be in any preparation form of a liquid form, a foamy form, a paste form, a cream form, or a solid form. The external preparation that is a liquid form, a foamy form, a paste form, a cream form or a solid form can be generally directly applied as it is, or can be applied by spraying or the like.

The external preparation can appropriately contain, in addition to the metal oxide (A) therein, beauty components and pharmaceutical components used in accordance with the intended use of the external preparation, and also any other components generally used in external preparations such as skin cosmetic materials, unless the objects of the present invention are adversely affected by inclusion thereof. The components include, except the metal oxide (A), an antioxidant, a UV absorbent, a surfactant, a thickener, an oily agent, a pH regulator, a bactericide, an anti-inflammatory agent, a preservative, a colorant, a chelating agent, a moisturizer, a pearly agent, ceramides, an antiperspirant, and fragrances.

In the first aspect of the invention, the content of the metal oxide (A) in the external preparation is, from the viewpoint of improving the adhesion suppressing effect, preferably 1% by mass or more, more preferably 5% by mass or more, even more preferably 7% by mass or more, and is, from the viewpoint of economy and feel in use as external preparations, preferably 50% by mass or less, more preferably 40% by mass or less, even more preferably 35% by mass or less.

In the case where the external preparation of the first aspect of the invention is an oil-in-water (O/W) type, the coating amount of the metal oxide (A) on the surface of skin is, from the viewpoint of improving the adhesion suppressing effect, 0.03 mg/cm$^2$ or more, preferably 0.04 mg/cm$^2$ or more, more preferably 0.05 mg/cm$^2$ or more, even more preferably 0.07 mg/cm$^2$ or more, further more preferably 0.10 mg/cm$^2$ or more, further more preferably 0.15 mg/cm$^2$ or more, and is, from the viewpoint of economy and feel in use as external preparations, preferably 0.8 mg/cm$^2$ or less, more preferably 0.7 mg/cm$^2$ or less, even more preferably 0.5 mg/cm$^2$ or less, further more preferably 0.3 mg/cm$^2$ or less. More specifically, the coating amount of the metal oxide (A) on the surface of skin is, from the viewpoint of improving the adhesion suppressing effect and also from the viewpoint of economy and feel in use as external preparation, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.7 mg/cm$^2$, further more preferably 0.10 to 0.5 mg/cm$^2$, further more preferably 0.10 to 0.3 mg/cm$^2$, further more preferably 0.15 to 0.3 mg/cm$^2$.

In the case where the external preparation of the first aspect of the invention is a water-in-oil (W/O) type, the coating amount of the metal oxide (A) on the surface of skin is, from the viewpoint of improving the adhesion suppressing effect, 0.03 mg/cm$^2$ or more, preferably 0.04 mg/cm$^2$ or more, more preferably 0.05 mg/cm$^2$ or more, even more preferably 0.07 mg/cm$^2$ or more, further more preferably 0.10 mg/cm$^2$ or more, further more preferably 0.15 mg/cm$^2$ or more, and is, from the viewpoint of economy and feel in use as external preparations, preferably 0.8 mg/cm$^2$ or less, more preferably 0.7 mg/cm$^2$ or less. More specifically, the coating amount of the metal oxide (A) on the surface of skin is, from the viewpoint of improving the adhesion suppressing effect and also from the viewpoint of economy and feel in use as external preparation, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.10 to 0.8 mg/cm$^2$, further more preferably 0.15 to 0.8 mg/cm$^2$, further more preferably 0.15 to 0.7 mg/cm$^2$.

[Adhesion Suppressing Method Against Air Harmful Substances: Second to Fourth Aspects of Invention]

The adhesion suppressing method against air harmful substances of the second aspect of the invention is a method for suppressing adhesion of air harmful substances that includes applying an external preparation to skin to suppress adhesion of air harmful substances to the skin, wherein:

the external preparation contains the following component (AI) and component (BI), and the ratio by mass of the content of the component (BI) to the content of the component (AI) in the external preparation [(BI)/(AI)] is 9 or less:

Component (AI): a hydrophobized metal oxide having an average primary particle diameter $d_{AI}$ of 800 nm or less, Component (BI): an ester oil.

The adhesion suppressing method against air harmful substances of the third aspect of the invention is a method for suppressing adhesion of air harmful substances that includes applying an external preparation to skin to suppress adhesion of air harmful substances to the skin, wherein:

the external preparation contains the following component (AI) and component (BII), and the ratio by mass of the content of the component (BII) to the content of the component (AI) in the external preparation [(BII)/(AI)] is 3.5 or less:

Component (AI): a hydrophobized metal oxide having an average primary particle diameter $d_{AI}$ of 800 nm or less, Component (BI): a nonvolatile hydrocarbon oil.

The adhesion suppressing method against air harmful substances of the fourth aspect of the invention is a method for suppressing adhesion of air harmful substances that includes applying an external preparation to skin to suppress adhesion of air harmful substances to the skin, wherein:

the external preparation contains the following component (AI) and component (BIII), and the ratio by mass of the content of the component (BIII) to the content of the component (AI) in the external preparation [(BIII)/(AI)] is 0.85 or less:

Component (AI): a hydrophobized metal oxide having an average primary particle diameter $d_{AI}$ of 800 nm or less, Component (BI): a nonvolatile silicone oil.

<External Preparation>

The external preparation that is used in the second to fourth aspects of the invention, from the viewpoint of improving the adhesion suppressing effect and also from the viewpoint of improving the feel in use in application to skin, contains the component (AI), and the component (BI), (BII) or (BIII).

[Component (AI): Hydrophobized Metal Oxide]

The component (AI) is a hydrophobized metal oxide having an average primary particle diameter $d_{AI}$ of 800 nm or less (hereinafter also referred to as "hydrophobized metal oxide").

The average primary particle diameter $d_{AI}$ of the component (AI) is, from the viewpoint of improving the adhesion suppressing effect, 800 nm or less, preferably 500 nm or less, more preferably 300 nm or less, even more preferably 200 nm or less, further more preferably 80 nm or less, further more preferably 50 nm or less, and is, from the viewpoint of general versatility, preferably 5 nm or more, more preferably 10 nm or more. More specifically, the average primary particle diameter $d_{AI}$ is, from the viewpoint of improving the adhesion suppressing effect and from the viewpoint of general versatility, preferably 5 to 800 nm, more preferably 5 to 500 nm, even more preferably 5 to 300 nm, further more preferably 5 to 200 nm, further more preferably 5 to 80 nm, further more preferably 5 to 50 nm, further more preferably 10 to 50 nm.

In the second to fourth aspects of the invention, the average primary particle diameter $d_{AI}$ can be determined on the observation image with a transmission electron microscope (TEM), like the average primary particle diameter $d_{AI}$ mentioned hereinabove. Here, the maximum minor diameter means a minor diameter having a maximum length of minor diameters perpendicular to the major diameter in the case where the component (AI) has a shape different from a tabular one. In the case where the component (AI) is a tabular one, the thicknesses of 300 primary particles in the image observed under the same condition as above are measured, and the data are averaged to give a number-average value. Specifically, the average primary particle diameter is measured according to the method described in the section of Examples.

The metal oxide of the component (AI) is not particularly limited as long as it can be generally used in external preparations such as cosmetic materials. Specific examples of the metal oxide (A) include titanium oxide, zinc oxide, cerium oxide, aluminum oxide (alumina), magnesium oxide, calcium oxide, zirconium oxide, iron oxide, and chromium oxide. Among these, from the viewpoint of giving UV protecting performance, preferred are at least one selected from the group consisting of titanium oxide, zinc oxide and cerium oxide, and more preferred are at least one selected from the group consisting of titanium oxide and zinc oxide.

In the case where the metal oxide of the component (AI) is titanium oxide, the crystal structure of titanium oxide may be any of an anatase-type, rutile-type or Brookite-type one, but is, from the viewpoint of general versatility, preferably a rutile-type or anatase-type one.

The shape of the component (AI) includes spherical, spindle-shaped, tabular and vesicular ones. Among these, from the viewpoint of improving the adhesion suppressing effect, a spherical, spindle-shaped or tabular one is preferred.

In the case where the metal oxide of the component (AI) is titanium oxide, preferably it is a spindle-shaped one from the viewpoint of improving the adhesion suppressing effect.

In the case where the metal oxide of the component (AI) is zinc oxide, preferably it is a spherical or tabular one from the viewpoint of improving the adhesion suppressing effect.

The existence form of the component (AI) may be in a form of primary particles or may also be in a form containing aggregates formed by aggregating primary particles (secondary particles), so far as the average primary particle diameter $d_{AI}$ thereof satisfies the above-mentioned range.

The external preparation for use in the present invention contains the hydrophobized component (AI), and the dispersibility of the component (AI) in the external preparation containing the component (BI), the component (BII) or the component (BIII) is improved to improve the adhesion suppressing effect.

The hydrophobizing treatment includes a fatty acid treatment; an alkylalkoxysilane treatment; a silicone treatment; a fluorine-containing compound treatment with a perfluoroalkyl phosphate, a perfluoroalcohol or a perfluoroalkylalkoxysilane; an amino acid treatment with an N-acylglutamic acid; and an alkyl phosphate treatment.

Among these, from the viewpoint of enhancing the dispersibility of the component (AI) in the external preparation containing the component (BI), the component (BII) or the component (BIII) to improve the adhesion suppressing effect, a fatty acid treatment, an alkylalkoxysilane treatment and a silicone treatment are preferred.

Specifically, from the viewpoint of enhancing the dispersibility of the component (AI) in the external preparation containing the component (BI), the component (BII) or the component (BIII) to improve the adhesion suppressing effect, the component (AI) is preferably at least one selected from the group consisting of the following component (AI-1), component (AI-2) and component (AI-3).

Component (AI-1): a fatty acid-treated metal oxide having an average primary particle diameter $d_{AI}$ of 800 nm or less.

Component (AI-2): an alkylalkoxysilane-treated metal oxide having an average primary particle diameter $d_{AI}$ of 800 nm or less.

Component (AI-3): a silicone-treated metal oxide having an average primary particle diameter $d_{AI}$ of 800 nm or less.

The surface treatment agent for use in the fatty acid treatment for the component (AI-1) includes a linear or branched fatty acid having 12 or more and 22 or less carbon atoms. Above all, from the viewpoint of enhancing the dispersibility of the component (AI) in the external preparation containing the component (BI), the component (BII) or the component (BIII) to improve the adhesion suppressing effect, preferred is a linear or branched higher fatty acid having 14 or more and 22 or less carbon atoms, more preferred is a linear or branched higher fatty acid having 16 or more and 20 or less carbon atoms, and even more preferred are stearic acid and isostearic acid.

The surface treatment agent for use in the alkylalkoxysilane treatment for the component (AI-2) is, from the viewpoint of enhancing the dispersibility of the component (AI) in the external preparation containing the component (BI), the component (BII) or the component (BIII) to improve the adhesion suppressing effect, preferably one having a linear or branched alkyl group with 6 or more and 20 or less carbon atoms, and is more preferably octyltriethoxysilane and octyltrimethoxysilane.

The surface treatment agent for use in the silicone treatment for the component (AI-3) includes various silicone oils such as methylpolysiloxane, dimethylpolysiloxane, methylphenylpolysiloxane, methylhydrogen polysiloxane, methylcyclopolysiloxane, dodecamethylcyclohexasiloxane, tetradecamethylhexasiloxane, dimethylsiloxane/methyl(polyoxyethylene)siloxane/methyl(polyoxypropylene)siloxane copolymer, dimethylsiloxane/methyl(polyoxyethylene)siloxane copolymer, dimethylsiloxane/methyl(polyoxypropylene)siloxane copolymer, dimethylsiloxane/methylcetyloxysiloxane copolymer, dimethylsiloxane/methylstearoxysiloxane copolymer, and alkyl acrylate/dimethicone copolymer. Among these, from the viewpoint of enhancing the dispersibility of the component (AI) in the external preparation containing the component (BI), the component (BII) or the component (BIII) to improve the adhesion suppressing effect, preferred are methylhydrogen polysiloxane and dimethylpolysiloxane.

One alone or two or more kinds of the above-mentioned surface treatment agents can be used either singly or as combined.

The treatment amount of hydrophobizing treatment is, from the viewpoint of enhancing the dispersibility of the component (AI) in the external preparation containing the component (BI), the component (BII) or the component (BIII) to improve the adhesion suppressing effect, preferably 0.1% by mass or more, and is preferably 40% by mass or less, more preferably 30% by mass or less, on the basis of the component (AI).

In the second to fourth aspects of the invention, the mass, the coating amount and the average primary particle diameter $d_{AI}$ of the component (AI) mean the mass, the coating amount and the average primary particle diameter $d_{AI}$ thereof, respectively, including the surface treatment agent.

In the case where the component (AI) is a hydrophobized titanium oxide, the $TiO_2$ content in the hydrophobized titanium oxide is, from the viewpoint of improving the adhesion suppressing effect, preferably 60% by mass or more, more preferably 70% by mass or more, and is preferably less than 100% by mass.

In the case where the component (AI) is hydrophobized zinc oxide, the ZnO content in the hydrophobized zinc oxide is, from the viewpoint of improving the adhesion suppressing effect, preferably 60% by mass or more, more preferably 70% by mass or more, and is preferably less than 100% by mass.

In the second aspect of the invention, the component (AI) is, from the viewpoint of enhancing the dispersibility of the component (AI) in the external preparation containing the component (BI) to improve the adhesion suppressing effect, preferably at least one selected from the group consisting a fatty acid-treated titanium oxide and a fatty acid-treated zinc oxide as the component (AI-1), an alkylalkoxysilane-treated titanium oxide and an alkylalkoxysilane-treated zinc oxide as the component (AI-2), and a silicone-treated titanium oxide and a silicone-treated zinc oxide as the component (AI-3), more preferably at least one selected from the group consisting an alkylalkoxysilane-treated titanium oxide and an alkylalkoxysilane-treated zinc oxide as the component (AI-2), and a silicone-treated titanium oxide and a silicone-treated zinc oxide as the component (AI-3), even more preferably at least one selected from selected from the group consisting an alkylalkoxysilane-treated titanium oxide and an alkylalkoxysilane-treated zinc oxide as the component (AI-2).

In the third aspect of the invention, the component (AI) is, from the viewpoint of enhancing the dispersibility of the component (AI) in the external preparation containing the component (BII) to improve the adhesion suppressing effect, preferably at least one selected from the group consisting a fatty acid-treated titanium oxide and a fatty acid-treated zinc oxide as the component (AI-1), an alkylalkoxysilane-treated titanium oxide and an alkylalkoxysilane-treated zinc oxide as the component (AI-2), and a silicone-treated titanium oxide and a silicone-treated zinc oxide as the component (AI-3), more preferably at least one selected from the group consisting a fatty acid-treated titanium oxide and a fatty acid-treated zinc oxide as the component (AI-1), and an alkylalkoxysilane-treated titanium oxide and an alkylalkoxysilane-treated zinc oxide as the component (AI-2), even more preferably at least one selected from the group consisting an alkylalkoxysilane-treated titanium oxide and an alkylalkoxysilane-treated zinc oxide as the component (AI-2).

In the second fourth of the invention, the component (AI) is, from the viewpoint of enhancing the dispersibility of the component (AI) in the external preparation containing the component (BIII) to improve the adhesion suppressing effect, preferably at least one selected from the group consisting a fatty acid-treated titanium oxide and a fatty acid-treated zinc oxide as the component (AI-1), an alkylalkoxysilane-treated titanium oxide and an alkylalkoxysilane-treated zinc oxide as the component (AI-2), and a silicone-treated titanium oxide and a silicone-treated zinc oxide as the component (AI-3), more preferably at least one selected from the group consisting a fatty acid-treated titanium oxide and a fatty acid-treated zinc oxide as the component (AI-1), and an alkylalkoxysilane-treated titanium oxide and an alkylalkoxysilane-treated zinc oxide as the component (AI-2), even more preferably at least one selected from the group consisting an alkylalkoxysilane-treated titanium oxide and an alkylalkoxysilane-treated zinc oxide as the component (AI-2).

Commercial products of the component (AI-1) include "STR-100C-LF" (stearic acid-treated titanium oxide) by Sakai Chemical Industry Co., Ltd.; "MPT-171" (stearic acid-treated titanium oxide) by Ishihara Sangyo Kaisha Ltd.; and "MT-100TV" (stearic acid-treated titanium oxide) and "MT-100Z" (stearic acid-treated titanium oxide) by Tayca Corporation.

Commercial products of the component (AI-2) include "STR-100C-OTS" (octyltriethoxysilane-treated titanium oxide), "STR-100W-OTS" (octyltriethoxysilane-treated titanium oxide), "FINEX-50-OTS" (octyltriethoxysilane-treated zinc oxide) and "FINEX-30-OTS" (octyltriethoxysilane-treated zinc oxide), all by Sakai Chemical Industry Co., Ltd.

Commercial products of the component (AI-3) include "STR-100A-LP" (silicone-treated titanium oxide) and "FINEX-50-LPTM" (silicone-treated zinc oxide), both by Sakai Chemical Industry Co., Ltd.; "JR-800S" (silicone-treated titanium oxide), "MPY-70M" (silicone-treated titanium oxide), "MICRO ZINC OXIDE MZ-405R3M (silicone-treated zinc oxide) and "MT-600KS" (silicone-treated zinc oxide), all by Tayca Corporation; and "D-FZN" (silicone-treated zinc oxide) by Daito Chemical Industry Co., Ltd.

[Component (BI): Ester Oil]

The external preparation in the second aspect of the invention contains the component (AI) and the component (BI).

The component (BI) is an oily agent, and is an ester oil. The ester oil includes a synthetic ester oil and natural oils and fats.

The component (BI) includes an ester of a monocarboxylic acid and a monoalcohol, an ester of a monocarboxylic acid and a polyalcohol, and an ester of a polycarboxylic acid and a monoalcohol.

The ester of a monocarboxylic acid and a monoalcohol includes an ester represented by the following general formula (1):

$$R^1\text{---COO---}R^2 \tag{1}$$

In the general formula (1), $R^1$ represents a linear or branched alkyl or alkenyl group having 1 or more and 25 or less carbon atoms or an aromatic moiety-containing hydrocarbon group having 6 or more and 24 or less carbon atoms, which may be substituted with a hydroxy group; and $R^2$ represents a linear or branched alkyl or alkenyl group having 1 or more and 30 or less carbon atoms.

In the case where $R^1$ is an alkyl group or an alkenyl group, the carbon number thereof is, from the viewpoint of improving the feel in use in application to skin, preferably 7 or more, more preferably 9 or more, even more preferably 11 or more, and is, from the same viewpoint as above, preferably 23 or less, more preferably 21 or less, even more preferably 19 or less.

In the case where $R^1$ is an aromatic moiety-containing hydrocarbon group, the carbon number thereof is, from the viewpoint of improving the feel in use in application to skin, preferably 8 or more, more preferably 10 or more, and is, from the same viewpoint as above, preferably 22 or less, more preferably 20 or less.

The carbon number of $R^2$ is, from the viewpoint of improving the feel in use in application to skin, preferably 2 or more, and is, from the same viewpoint as above, preferably 28 or less, more preferably 20 or less, even more preferably 18 or less.

Also from the viewpoint of improving the feel in use in application to skin, preferably, at least one of $R^1$ and $R^2$ is a branched alkyl group.

Specific examples of the ester represented by the general formula (1) include at least one selected from the group consisting of myristyl 2-ethylhexanoate, cetyl 2-ethylhexanoate, stearyl 2-ethylhexanoate, isodecyl octanoate, cetyl octanoate, isocetyl octanoate, isononyl isononanoate, isotridecyl isononanoate, hexyldecyl dimethyloctanoate, hexyl laurate, isopropyl myristate, isotridecyl myristate, 2-hexyldecyl myristate, myristyl myristate, octyldodecyl myristate, isopropyl palmitate, 2-ethylhexyl palmitate, 2-hexyldecyl palmitate, 2-heptylundecyl palmitate, butyl stearate, 2-ethylhexyl stearate, stearyl stearate, isocetyl stearate, cetyl stearate, isocetyl isostearate, cholesteryl isostearate, decyl oleate, oleyl oleate, octyldodecyl oleate, lanolin acetate, cholesteryl hydroxystearate, isopropyl lanolin fatty acid, cholesteryl lanolin fatty acid, methyl castor oil fatty acid (methyl ricinoleate), cetyl lactate, myristyl lactate, and alkyl benzoates where the alkyl has 12 to 15 carbon atoms).

The ester of a monocarboxylic acid and a monoalcohol also includes an ester represented by the following general formula (2):

$$R^3\text{---COO-(AO)}_n\text{---}R^4 \tag{2}$$

In the general formula (2), $R^3$ represents a linear or branched alkyl or alkenyl group having 1 or more and 25 or less carbon atoms which may be substituted with a hydroxy group; $R^4$ represents an aromatic moiety-containing hydrocarbon group having 6 or more and 24 or less carbon atoms. AO represents an alkyleneoxy group having 2 or more and 4 or less carbon atoms, and n represents an average addition molar number of 1 or more and 50 or less.

$R^3$ is, from the viewpoint of improving the feel in use in application to skin, preferably an alkyl group having a carbon number of 7 or more, and is, from the same viewpoint as above, preferably an alkyl group having a carbon number of 23 or less, more preferably 21 or less, even more preferably 19 or less.

$R^4$ is, from the viewpoint of improving the feel in use in application to skin, preferably an aromatic moiety-containing hydrocarbon group having a carbon number of 6 or more, and is, from the same viewpoint as above, preferably an aromatic moiety-containing hydrocarbon group having a carbon number of 22 or less, more preferably 20 or less, even more preferably 18 or less. Even more preferably, $R^4$ is a benzyl group.

The group AO is, from the viewpoint of improving the feel in use in application to skin, preferably a propyleneoxy group, and from the same viewpoint as above, n is preferably 1 or more and 10 or less, more preferably 1 or more and 5 or less.

Specific examples of the ester represented by the general formula (2) include an ester of myristic acid and an addition product of propylene oxide (3 mols) of benzyl alcohol ("Crodamol STS" by Croda Japan), and an ester of 2-ethylhexanoic acid and an addition product of propylene oxide (3 mols) of benzyl alcohol ("Crodamol SFX" by Croda Japan).

The ester of a monocarboxylic acid and a polyalcohol includes an ester represented by the following general formula (3):

$$R^5\text{---(OCOR}^6)_p \tag{3}$$

In the general formula (3), $R^5$ represents a polyalcohol residue, and $R^5$ is preferably a linear or branched hydrocarbon group having 2 or more and 10 or less carbon atoms, $R^6$ represents a monocarboxylic acid residue having 1 or more and 25 or less carbon atoms, and p represents an integer of 2 or more and 10 or less.

$R^5$ may have an ether bond. p is preferably the same number of the hydroxy groups that the polyalcohol has.

$R^6$ is, from the viewpoint of improving the feel in use in application to skin, preferably an alkyl group having a carbon number of 7 or more, more preferably 9 or more, even more preferably 11 or more, and is, from the same viewpoint as above, an alkyl group having a carbon number of 23 or less, more preferably 21 or less, even more preferably 19 or less.

The ester represented by the general formula (3) includes neopentyl glycol dicaprylate, neopentyl glycol di-2-ethylhexanoate, propanediol di(caprylate/caprate), propanediol diisostearate, ethylene glycol di-2-ethylhexanoate, glyceryl tri(caprylate/caprate), glyceryl tri-2-ethylhexylate, glyceryl tri-2-heptylundecanoate, glyceryl trimyristate, trimethylolpropane tri-2-ethylhexylate, trimethylolpropane triisostearate, pentaerythritol tetra-2-ethylhexanoate, dipentaerythritol fatty acid, and natural oils and fats.

The natural oils and fats include castor oil, cacao oil, mink oil, avocado oil, olive oil, sunflower oil, *Camellia* oil, apricot kernel oil, almond oil, wheat germ oil, *Theobroma grandiflorum* seed oil, grape seed oil, babassu oil, jojoba oil, macadamia nut oil, *Camellia oleifera* oil, Shea butter oil, *Camellia reticulata* seed oil, and meadowfoam oil.

The ester of a polycarboxylic acid and a monoalcohol includes an ester represented by the following general formula (4):

$$R^7—(COOR^8)_q \quad (4)$$

In the general formula (4), $R^7$ represents a polycarboxylic acid residue having 2 or more and 10 or less carbon atoms, $R^8$ represents a monoalcohol residue having 1 or more and 25 or less carbon atoms, q represents an integer of 2 or more and 10 or less. Preferably, q is the same number of the carboxy groups that the polycarboxylic acid has.

The carbon number of $R^8$ is, from the viewpoint of improving the feel in use in application to skin, preferably 3 or more, more preferably 7 or more, and is, from the same viewpoint as above, preferably 23 or less, more preferably 21 or less, even more preferably 19 or less.

Specifically, the ester includes diisostearyl malate, 2-ethylhexyl succinate, diisobutyl adipate, di-2-heptylundecyl adipate, di-2-hexyldecyl adipate, di-2-ethylhexyl sebacate, and diisopropyl sebacate.

The component (BI) may be an ester-based UV absorbent having UV absorption performance by the structure thereof from the viewpoint of protecting skin damage from UV rays.

The ester-based UV absorbent includes a salicylate-based UV absorbent such as homomenthyl salicylate, octyl salicylate, and triethanolamine salicylate; a para-aminobenzoic acid-based UV absorbent such as para-aminobenzoic acid, ethyldihydroxypropyl-para-aminobenzoic acid, glyceryl para-aminobenzoate, octyl dimethyl-para-aminobenzoate, amyl dimethyl-para-aminobenzoate, and 2-ethylhexyl dimethyl-para-aminobenzoate; a cinnamate-based UV absorbent such as 2-ethylhexyl para-methoxycinnamate (e.g., "Uvinul MC80" by BASF Japan Ltd.), glyceryl diparamethoxycinnamate mono-2-ethylhexanoate, methyl 2,5-diisopropylcinnamate, 2,4,6-tris[4-(2-ethylhexyloxycarbonyl)anilinol-1,3,5-triazine (ethylhexyltriazone) (e.g., "Uvinul T150" by BASF Japan Ltd.), methylbis(trimethylsiloxy)silylisopentyl trimethoxycinnamate, a cinnamate mixture of isopropyl/diisopropyl paramethoxycinnamate, and p-methoxyhydrocinnamate diethanolamine salt; octocrylene (e.g., "Parasol 340" by DSM Nutrition Japan Ltd.); 2-ethylhexyl dimethoxybenzylidene-dioxoimidazolidinepropionate (e.g., "Softshade DH" by Ajinomoto Co., Inc.): cinoxate; methyl O-aminobenzoate; and hexyl diethylaminohydroxybenzoylbenzoate (e.g., "Uvinul A Plus" and "Uvinul Plus GRANULAR", both by BASF Japan Ltd.).

The component (BI) is, from the viewpoint of improving the adhesion suppressing effect and from the viewpoint of improving the feel in use in application to skin, preferably an ester oil that is liquid at 25° C. The ester oil liquid at 25° C. is an ester oil having a melting point of 25° C. or lower. Namely, the component (BI) is preferably an ester oil that is fluid at 25° C. under an atmospheric pressure. Specifically, the component (BI) is preferably an ester represented by the general formula (1) or the general formula (3), and is more preferably at least one selected from the group consisting of isopropyl palmitate, isononyl isononanoate, neopentyl glycol dicaprylate, neopentyl glycol di-2-ethylhexanoate, and glyceryl tri-2-ethylhexylate.

In the case where an ester-based UV absorbent is used as the component (BI), the component (BI) is, from the viewpoint of improving the adhesion suppressing effect and from the viewpoint of improving the feel in use in application to skin, preferably one or more selected from 2-ethylhexyl parametoxycinnamate, 2,4,6-tris[4-(2-ethylhexyloxycarbonyl)anilino]-1,3,5-triazine and hexyl diethylaminohydroxybenzoylbenzoate.

[Component (BII): Nonvolatile Hydrocarbon Oil]

The external preparation in the third aspect of the invention contains the component (AI) and the component (BII).

The component (BII) is an oily agent, and is a nonvolatile hydrocarbon oil.

"Nonvolatile" as referred to in the third aspect of the invention means that the amount of evaporation at 25° C. for 6 hours is less than 20%, measured by the above-mentioned method.

The component (BII) is, from the viewpoint of improving the feel in use in application to skin, preferably a saturated or unsaturated hydrocarbon having 18 or more carbon atoms.

Specific examples of the component (BII) include a hydrocarbon oil liquid at 25° C., such as squalene, squalane, liquid paraffin, hydrogenated polyisobutene (liquid isoparaffin, heavy liquid isoparaffin), liquid ozokerite, α-olefin oligomer, cycloparaffin, polybutene, and pristane; and a hydrocarbon oil solid at 25° C., such as vaseline, ceresin, ozokerite, paraffin wax, microcrystalline wax, and polyethylene wax. One alone or two or more of the above can be used as the component (BII) either singly or as combined.

Among these, from the viewpoint of improving the feel in use in application to skin, preferred is a hydrocarbon oil not having a melting point but liquid at 25° C., more preferred is a hydrocarbon oil having a kinematic viscosity at 25° C. of 5 $mm^2$/s or more and 100,000 $mm^2$/s or less, even more preferred is a hydrogenated polyisobutene, and further more preferred is a liquid isoparaffin.

The kinematic viscosity at 25° C. of the component (BII) is, from the viewpoint of bettering the feel in use in application to skin, more preferably 6 $mm^2$/s or more, and is, from the same viewpoint, even more preferably 10,000 $mm^2$/s or less, further more preferably 5,000 $mm^2$/s or less, further more preferably 1,000 $mm^2$/s or less, further more preferably 500 $mm^2$/s or less, further more preferably 300 $mm^2$/s or less, further more preferably 100 $mm^2$/s or less, further more preferably 50 $mm^2$/s or less, further more preferably 30 $mm^2$/s or less.

The kinematic viscosity at 25° C. of the component (BII) can be measured according to the same method as in the first aspect of the invention.

Commercial products of the component (BII) include "Parleam EX" (liquid isoparaffin) by NOF Corporation.

[Component (BIII): Nonvolatile Silicone Oil]

The external preparation in the fourth aspect of the invention contains the component (AI) and the component (BIII).

The component (BIII) is an oily agent and is a nonvolatile silicone oil.

"Nonvolatile" as referred to in the fourth aspect of the invention is the same as in the third aspect of the invention.

Specifically, the component (BIII) includes a linear organopolysiloxane such as dimethylpolysiloxane, methylphenylpolysiloxane, methylhydrogen polysiloxane, and dimethiconol (dimethylpolysiloxane blocked with a hydroxy group at both ends); a modified silicone such as an amino-modified silicone (dimethylpolysiloxane having an amino group in the molecule), and a polyglycerin-modified silicone having a branched polyglycerol chain at both ends; an amino derivative silicone; and a liquid, semisolid, or solid silicone oil such as silicone wax. One alone or two or more kinds of the above can be used as the component (BIII) either singly or as combined.

Among these, from the viewpoint of improving the feel in use in application to skin, preferred is a linear organopolysiloxane, and more preferred is dimethylpolysiloxane.

The component (BIII) is, from the viewpoint of improving the feel in use in application to skin and from the viewpoint of improving the adhesion suppressing effect, preferably a silicone oil having a kinematic viscosity at 25° C. of 5 mm$^2$/s or more and 100,000 mm$^2$/s or less.

The kinematic viscosity at 25° C. of the component (BIII) is, from the viewpoint of improving the feel in use in application to skin, more preferably 6 mm$^2$/s or more, and is, from the viewpoint of improving the adhesion suppressing effect and from the viewpoint of improving the feel in use in application to skin, more preferably 10,000 mm$^2$/s or less, even more preferably 5,000 mm$^2$/s or less, further more preferably 1,000 mm$^2$/s or less, further more preferably 500 mm$^2$/s or less, further more preferably 300 mm$^2$/s or less, further more preferably 100 mm$^2$/s or less, further more preferably 50 mm$^2$/s or less, further more preferably 30 mm$^2$/s or less. More specifically, the kinematic viscosity at 25° C. of the component (BIII) is, from the viewpoint of improving the adhesion suppressing effect and from the viewpoint of improving the feel in use in application to skin, preferably 5 to 100,000 mm$^2$/s, more preferably 5 to 10,000 mm$^2$/s, even more preferably 5 to 5,000 mm$^2$/s, further more preferably 5 to 1,000 mm$^2$/s, further more preferably 5 to 500 mm$^2$/s, further more preferably 5 to 300 mm$^2$/s, further more preferably 5 to 100 mm$^2$/s, further more preferably 5 to 50 mm$^2$/s, further more preferably 5 to 30 mm$^2$/s, further more preferably 6 to 30 mm$^2$/s.

The kinematic viscosity at 25° C. of the component (BIII) can be measured according to the same method as in the first aspect of the invention.

Commercial products of the component (BIII) include "KF-96A-6cs" (dimethylpolysiloxane) and "KF-96A-10cs" (dimethylpolysiloxane), both by Shin-etsu Chemical Industry Co., Ltd.

The external preparation in the second aspect of the invention can appropriately contain, in addition to the component (AI) and the component (BI), beauty components and pharmaceutical components used in accordance with the intended use of the external preparation, and also any other components generally used in external preparations such as skin cosmetic materials, unless the objects of the present invention are adversely affected by inclusion thereof. The components include, except the component (AI) and the component (BI), an oily agent, an antioxidant, a UV absorbent, a surfactant, a thickener, a pH regulator, a bactericide, an anti-inflammatory agent, a preservative, a colorant, a chelating agent, a moisturizer, a pearly agent, ceramides, an antiperspirant, and fragrances.

[Component (CI): Nonvolatile Oily Agent Except Component (BI)]

The external preparation in the second aspect of the invention may further contain any other nonvolatile oily agent than the component (BI), as a component (CI).

"Nonvolatile" in the second aspect of the invention is the same as in the third aspect of the invention.

The component (CI) includes one or more selected from a hydrocarbon oil, a silicone oil, a higher fatty acid, and a higher alcohol. Above all, preferred are at least one selected from the group consisting of a nonvolatile hydrocarbon oil (CI-1) (hereinafter this may also be referred to as "component (CI-1)"), and a nonvolatile silicone oil (CI-2) (hereinafter this may also be referred to as "component (CI-2)").

The component (CI-1) is, from the viewpoint of improving the feel in use in application to skin, preferably a saturated or unsaturated hydrocarbon having 18 or more carbon atoms.

Specific examples and commercial products of the component (CI-1) are the same as those exemplified hereinabove for the above-mentioned component (BII). One alone or two or more kinds of the above can be used as the component (CI-1) either singly or as combined.

Above all, from the viewpoint of improving the feel in use in application to skin, the component (CI-1) is preferably a hydrocarbon oil not having a melting point but liquid at 25° C., more preferably a hydrocarbon oil having a kinematic viscosity at 25° C. of 5 mm$^2$/s or more and 100,000 mm$^2$/s or less, even more preferably a hydrogenated polyisobutene, further more preferably a liquid isoparaffin.

The kinematic viscosity at 25° C. of the component (CI-1) is, from the viewpoint of improving the feel in use in application to skin, more preferably 6 mm$^2$/s or more, and is, from the same viewpoint as above, more preferably 10,000 mm$^2$/s or less, even more preferably 5,000 mm$^2$/s or less, further more preferably 1,000 mm$^2$/s or less, further more preferably 500 mm$^2$/s or less, further more preferably 300 mm$^2$/s or less, further more preferably 100 mm$^2$/s or less, further more preferably 50 mm$^2$/s or less, further more preferably 30 mm$^2$/s or less.

The kinematic viscosity at 25° C. of the component (CI-1) can be measured in the same manner as above.

The component (CI-2) is a nonvolatile silicone oil, and specific examples and commercial products of the component (CI-2) are the same as those exemplified hereinabove for the component (BIII). One alone or two or more kinds of the above can be used as the component (CI-2) either singly or as combined.

Above all, from the viewpoint of improving the feel in use in application to skin, the component (CI-2) is preferably a linear organopolysiloxane, more preferably dimethylpolysiloxane.

The component (CI-2) is, from the viewpoint of improving the feel in use in application to skin and from the viewpoint of improving the adhesion suppressing effect, preferably a silicone oil having a kinematic viscosity at 25° C. of 5 mm$^2$/s or more and 100,000 mm$^2$/s or less.

The kinematic viscosity at 25° C. of the component (CI-2) is, from the viewpoint of improving the feel in use in applying to skin, more preferably 6 mm$^2$/s or more, and is, from the viewpoint of improving the adhesion suppressing effect and from the viewpoint of improving the feel in use in application to skin, more preferably 10,000 mm$^2$/s or less, even more preferably 5,000 mm$^2$/s or, further more preferably 1,000 mm$^2$/s or less, further more preferably 500 mm$^2$/s or less, further more preferably 300 mm$^2$/s or less, further more preferably 100 mm$^2$/s or less, further more preferably 50 mm$^2$/s or less, further more preferably 30 mm$^2$/s or less.

The kinematic viscosity at 25° C. of the component (CI-2) can be measured in the same manner as above.

The external preparation in the third aspect of the invention can appropriately contain, in addition to the component (AI) and the component (BII), beauty components and pharmaceutical components used in accordance with the intended use of the external preparation, and also any other components generally used in external preparations such as skin cosmetic materials, unless the objects of the present invention are adversely affected by inclusion thereof. The components include, except the component (AI) and the component (BII), an oily agent, an antioxidant, a UV absorbent, a surfactant, a thickener, a pH regulator, a bactericide, an anti-inflammatory agent, a preservative, a colorant, a chelating agent, a moisturizer, a pearly agent, ceramides, an antiperspirant, and fragrances.

[Component (CII): Nonvolatile Oily Agent Except Component (BII)]

The external preparation in the third aspect of the invention may further contain any other nonvolatile oily agent than the component (BII), as a component (CII). The component (CII) includes at least one selected from the group consisting of an ester oil, a silicone oil, a higher fatty acid, and a higher alcohol. Above all, preferred are at least one selected from the group consisting of an ester oil (CII-1) (hereinafter this may also be referred to as "component (CII-1)"), and a nonvolatile silicone oil (CII-2) (hereinafter this may also be referred to as "component (CII-2)").

The component (CII-1) includes a synthetic ester oil and natural oils and fats, and specifically, examples thereof may be the same as those exemplified hereinabove for the component (BI), such as an ester of a monocarboxylic acid and a monoalcohol, an ester of a monocarboxylic acid and a polyalcohol, and an ester of a polycarboxylic acid and a monoalcohol.

The component (CII-1) is, from the viewpoint of improving the adhesion suppressing effect and from the viewpoint of improving the feel in use in application to skin, preferably an ester oil liquid at 25° C. The ester oil liquid at 25° C. is an ester oil having a melting point of 25° C. or lower. Namely, the component (CII-1) is preferably an ester oil that is fluid at 25° C. under an atmospheric pressure. Specifically, the component (CII-1) is preferably an ester represented by the general formula (1) or the general formula (3), and is more preferably at least one selected from the group consisting of isopropyl palmitate, isononyl isononanoate, neopentyl glycol dicaprylate, neopentyl glycol di-2-ethylhexanoate, and glyceryl tri-2-ethylhexylate.

In the case where an ester-based UV absorbent is used as the component (CII-1), the component (CII-1) is, from the viewpoint of improving the adhesion suppressing effect and from the viewpoint of improving the feel in use in application to skin, preferably at least one selected from the group consisting of 2-ethylhexyl paramethoxycinnamate, 2,4,6-tris[4-(2-ethylhexyloxycarbonyl)anilino]-1,3,5-triazine and hexyl diethylaminohydroxybenzoylbenzoate.

The component (CII-2) is a nonvolatile silicone oil, and specific examples and commercial products of the component (CII-2) are the same as those exemplified hereinabove for the component (BIII). One alone or two or more kinds of the above can be used as the component (CII-2) either singly or as combined.

Above all, the component (CII-2) is, from the viewpoint of improving the feel in use in application to skin, preferably a linear organopolysiloxane, more preferably dimethylpolysiloxane.

The component (CII-2) is, from the viewpoint of improving the feel in use in application to skin and from the viewpoint of improving the adhesion suppressing effect, preferably a silicone oil having a kinematic viscosity at 25° C. of 5 mm$^2$/s or more and 100,000 mm$^2$/s or less.

The kinematic viscosity at 25° C. of the component (CII-2) is, from the viewpoint of improving the feel in use in application to skin, more preferably 6 mm$^2$/s or more, and is, from the viewpoint of improving the adhesion suppressing effect and from the viewpoint of improving the feel in use in application to skin, more preferably 10,000 mm$^2$/s or less, even more preferably 5,000 mm$^2$/s or, further more preferably 1,000 mm$^2$/s or less, further more preferably 500 mm$^2$/s or less, further more preferably 300 mm$^2$/s or less, further more preferably 100 mm$^2$/s or less, further more preferably 50 mm$^2$/s or less, further more preferably 30 mm$^2$/s or less.

The kinematic viscosity at 25° C. of the component (CII-2) can be measured in the same manner as above.

The external preparation in the fourth aspect of the invention can appropriately contain, in addition to the component (AI) and the component (BIII), beauty components and pharmaceutical components used in accordance with the intended use of the external preparation, and also any other components generally used in external preparations such as skin cosmetic materials, unless the objects of the present invention are adversely affected by inclusion thereof. The components include, except the component (AI) and the component (BIII), an oily agent, an antioxidant, a UV absorbent, a surfactant, a thickener, a pH regulator, a bactericide, an anti-inflammatory agent, a preservative, a colorant, a chelating agent, a moisturizer, a pearly agent, ceramides, an antiperspirant, and fragrances.

[Component (CIII): Nonvolatile Oily Agent Except Component (BIII)]

The external preparation in the fourth aspect of the invention may further contain any other nonvolatile oily agent than the component (BIII), as a component (CIII). The component (CIII) includes at least one selected from the group consisting of an ester oil, a hydrocarbon oil, a higher fatty acid, and a higher alcohol. Above all, preferred are at least one selected from the group consisting of an ester oil (CIII-1) (hereinafter this may also be referred to as "component (CIII-1)"), and a nonvolatile hydrocarbon oil (CIII-2) (hereinafter this may also be referred to as "component (CIII-2)").

The component (CIII-1) includes a synthetic ester oil and natural oils and fats, and specifically, examples thereof may be the same as those exemplified hereinabove for the component (BI), such as an ester of a monocarboxylic acid and a monoalcohol, an ester of a monocarboxylic acid and a polyalcohol, and an ester of a polycarboxylic acid and a monoalcohol.

The component (CIII-1) is, from the viewpoint of improving the adhesion suppressing effect and from the viewpoint of improving the feel in use in application to skin, preferably an ester oil liquid at 25° C. The ester oil liquid at 25° C. is an ester oil having a melting point of 25° C. or lower. Namely, the component (CIII-1) is preferably an ester oil that is fluid at 25° C. under an atmospheric pressure. Specifically, the component (CIII-1) is preferably an ester represented by the general formula (1) or the general formula (3), and is more preferably at least one selected from the group consisting of isopropyl palmitate, isononyl isononanoate, neopentyl glycol dicaprylate, neopentyl glycol di-2-ethylhexanoate, and glyceryl tri-2-ethylhexylate.

In the case where an ester-based UV absorbent is used as the component (CIII-1), the component (CIII-1) is, from the viewpoint of improving the adhesion suppressing effect and from the viewpoint of improving the feel in use in application to skin, preferably at least one selected from the group consisting of 2-ethylhexyl paramethoxycinnamate, 2,4,6-tris [4-(2-ethylhexyloxycarbonyl)anilino]-1,3,5-triazine and hexyl diethylaminohydroxybenzoylbenzoate.

The component (CIII-2) is a nonvolatile hydrocarbon oil, and is, from the viewpoint of improving the feel in use in application to skin, preferably a saturated or unsaturated hydrocarbon having 18 or more carbon atoms.

Specific examples and commercial products of the component (CIII-2) are the same as those exemplified hereinabove for the component (BII). One alone or two or more kinds of the above can be used as the component (CIII-2) either singly or as combined.

Above all, the component (CIII-2) is, from the viewpoint of improving the feel in use in application to skin, preferably a hydrocarbon oil not having a melting point but liquid at 25° C., more preferably a hydrocarbon oil having a kinematic viscosity at 25° C. of 5 mm$^2$/s or more and 100,000 mm$^2$/s or less, even more preferably a hydrogenated polyisobutene, further more preferably a liquid isoparaffin.

The kinematic viscosity at 25° C. of the component (CIII-2) is, from the viewpoint of improving the feel in use in application to skin, more preferably 6 mm$^2$/s or more, and is, from the same viewpoint as above, more preferably 10,000 mm$^2$/s or less, even more preferably 5,000 mm$^2$/s or less, further more preferably 1,000 mm$^2$/s or less, further more preferably 500 mm$^2$/s or less, further more preferably 300 mm$^2$/s or less, further more preferably 100 mm$^2$/s or less, further more preferably 50 mm$^2$/s or less, further more preferably 30 mm$^2$/s or less.

The kinematic viscosity at 25° C. of the component (CIII-2) can be measured in the same manner as above.

[Component (D): Volatile Oil]

In the second to fourth aspects of the invention, the external preparation may further contain a volatile oil as a component (D).

"Volatile" in the second to fourth aspects of the invention means that the amount of evaporation at 25° C. for 6 hours, as measured according to the above-mentioned method, is more than 20%.

The component (D) includes a volatile silicone oil and a volatile hydrocarbon oil.

Specific examples and commercial products of the volatile silicone oil and the volatile hydrocarbon oil in the second to fourth aspects of the invention are the same as those exemplified hereinabove in the first aspect of the invention, and preferred volatile silicone oils and volatile hydrocarbon oils are also the same as in the first aspect of the invention.

[Production of External Preparation]

The external preparation for use in the second to fourth aspects of the invention can be produced by appropriately employing known methods in accordance with the form of the external preparation. For example, there is mentioned a method of blending the component (AI), the component (BI), the component (BII) or the component (BIII) and optionally the above-mentioned other components by stirring and mixing them with a disperser or the like.

In the case where the external preparation is a water-in-oil (W/O) type or an oil-in-water (O/W) type to be mentioned hereinunder, also employable is a method including preparing an aqueous phase and an oily phase and mixing the two.

(Content of Component (AI) in External Preparation)

In the second to fourth aspect of the invention, the content of the component (AI) in the external preparation is, from the viewpoint of improving the adhesion suppressing effect, preferably 1% by mass or more, more preferably 2% by mass or more, even more preferably 3% by mass or more, and is, from the viewpoint of improving the feel in use in application to skin and from the viewpoint of economy, preferably 40% by mass or less, more preferably 35% by mass or less, even more preferably 30% by mass or less. More specifically, the content of the component (AI) is, from the viewpoint of improving the adhesion suppressing effect and from the viewpoint of improving the feel in use in application to skin, preferably 1 to 40% by mass, more preferably 2 to 35% by mass, even more preferably 3 to 30% by mass.

(Total Content of Component (AI-1), Component (AI-2) and Component (AI-3) in External Preparation)

In the second to fourth aspect of the invention, the total content of the component (AI-1), the component (AI-2) and the component (AI-3) in the external preparation is, from the viewpoint of improving the adhesion suppressing effect, preferably 1% by mass or more, more preferably 2% by mass or more, even more preferably 3% by mass or more, and is, from the viewpoint of improving the feel in use in application to skin and from the viewpoint of economy, preferably 40% by mass or less, more preferably 35% by mass or less, even more preferably 30% by mass or less. More specifically, the total content of the component (AI-1), the component (AI-2) and the component (AI-3) is, from the viewpoint of improving the adhesion suppressing effect and from the viewpoint of improving the feel in use in application to skin, preferably 1 to 40% by mass, more preferably 2 to 35% by mass, even more preferably 3 to 30% by mass.

The content and the mass ratio of each component in the external preparation in the second aspect of the invention are as follows.

(Content of Component (BI) in External Preparation)

The content of the component (BI) in the external preparation is, from the viewpoint of improving the feel in use in application to skin, preferably 0.05% by mass or more, more preferably 0.1% by mass or more, even more preferably 1% by mass or more, further more preferably 3% by mass or more, further more preferably 5% by mass or more, further more preferably 8% by mass or more, further more preferably 10% by mass or more, and is, from the same viewpoint and from the viewpoint of enhancing the adhesion suppressing effect, preferably 60% by mass or less, more preferably 50% by mass or less, even more preferably 40% by mass or less, further more preferably 30% by mass or less, further more preferably 25% by mass or less, further more preferably 20% by mass or less, further more preferably 18% by mass or less, further more preferably 16% by mass or less.

(Mass Ratio [(BI)/(AI)])

The ratio by mass of the content of the component (BI) to the content of the component (AI) in the external preparation [(BI)/(AI)] is, from the viewpoint of improving the adhesion suppressing effect, 9 or less, preferably 8 or less, more preferably 6 or less, even more preferably 4 or less, further more preferably 3 or less, and is, from the viewpoint of improving the feel in use in application to skin, preferably 0.01 or more, more preferably 0.05 or more, even more preferably 0.1 or more. More specifically, the mass ratio [(BI)/(AI)] is, from the viewpoint of improving the adhesion suppressing effect and from the viewpoint of improving the feel in use in application to skin, preferably 0.9 or less and 0.01 or more, more preferably 8 or less and 0.01 or more, even more preferably 6 or less and 0.05 or more, further more preferably 4 or less and 0.05 or more, further more preferably 4 or less and 0.1 or more, further more preferably 3 or less and 0.1 or more.

(Mass Ratio [(BI)/[(AI-1)+(AI-2)+(AI-3)]])

In the case where the component (AI) is at least one selected from the group consisting of the component (AI-1), the component (AI-2) and the component (AI-3), the ratio by mass of the content of the component (BI) to the total content of the component (AI-1), the component (AI-2) and the component (AI-3) in the external preparation [(BI)/[(AI-1)+(AI-2)+(AI-3)]] is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more. More specifically, the mass ratio [(BI)/[(AI-1)+(AI-2)+(AI-3)]] is, from the viewpoint of improving the adhesion suppressing effect and from the viewpoint of improving the feel in use in application to skin, preferably 9 or less and 0.01 or more, more preferably 8 or less and 0.01 or more, even more preferably 6 or less and 0.05 or more, further more preferably 4 or less and 0.05 or more, further more preferably 4 or less and 0.1 or more, further more preferably 3 or less and 0.1 or more.

In the case where the external preparation further contains the component (CI-1) (nonvolatile hydrocarbon oil), the ratio by mass of the content of the component (CI-1) to the content of the component (AI) in the external preparation, $\alpha_I 1$ $(=[(CI-1)/(AI)])$ is, from the viewpoint of improving the adhesion suppressing effect, preferably 3.5 or less, more preferably 3 or less, even more preferably 2.5 or less, further more preferably 2 or less, and is, from the viewpoint of improving the feel in use in application to skin, preferably 0.01 or more, more preferably 0.03 or more, even more preferably 0.05 or more, further more preferably 0.1 or more.

The ratio by mass of the total content of the component (BI) and the component (CI-1) to the content of the component (AI) in the external preparation, $\beta_I 1$ $(=[[(BI)+(CI-1)]/(AI)])$ is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $\alpha_I 1$ is 3.5 or less and 0.01 or more and the mass ratio $\beta_I 1$ is 9 or less and 0.01 or more, more preferably the mass ratio $\alpha_I 1$ is 3 or less and 0.03 or more and the mass ratio $\beta_I 1$ is 8 or less and 0.01 or more, even more preferably the mass ratio $\alpha_I 1$ is 2.5 or less and 0.05 or more and the mass ratio $\beta_I 1$ is 6 or less and 0.05 or more, further more preferably the mass ratio $\alpha_I 1$ is 2 or less and 0.1 or more and the mass ratio $\beta_I 1$ is 4 or less and 0.1 or more, further more preferably the mass ratio $\alpha_I 1$ is 2 or less and 0.1 or more and the mass ratio $\beta_I 1$ is 3 or less and 0.1 or more.

In the case where the external preparation further contains the component (CI-1), a preferred numerical range of the ratio by mass of the content of the component (CI-1) to the total content of the component (AI-1), the component (AI-2) and the component (AI-3) in the external preparation, $\alpha_I 1$ $(=[(CI-1)/[(AI-1)+(AI-2)+(AI-3)]])$ is the same as the preferred numerical range of the mass ratio $\alpha_I 1$.

A preferred numerical range of the ratio by mass of the total content of the component (BI) and the component (CI-1) to the total content of the component (AI-1), the component (AI-2) and the component (AI-3) in the external preparation, $\beta_I I$ $(=[[(BI)+(CI-1)]/[(AI-1)+(AI-2)+(AI-3)]])$ is the same as the preferred numerical range of the mass ratio $\beta_I 1$.

From the viewpoint of improving the adhesion suppressing effect and from the viewpoint of improving the feel in use in application to skin, preferably the mass ratio $\alpha_I I$ is 3.5 or less and 0.01 or more and the mass ratio $\beta_I I$ is 9 or less and 0.01 or more, more preferably the mass ratio $\alpha_I I$ is 3 or less and 0.03 or more and the mass ratio $\beta_I I$ is 8 or less and 0.01 or more, even more preferably the mass ratio $\alpha_I I$ is 2.5 or less and 0.05 or more and the mass ratio $\beta_I I$ is 6 or less and 0.05 or more, further more preferably the mass ratio $\alpha_I I$ is 2 or less and 0.1 or more and the mass ratio $\beta_I I$ is 4 or less and 0.1 or more, further more preferably the mass ratio $\alpha_I I$ is 2 or less and 0.1 or more and the mass ratio $\beta_I I$ is 3 or less and 0.1 or more.

In the case where the external preparation further contains the component (CI-2) (nonvolatile silicone oil), the ratio by mass of the content of the component (CI-2) to the content of the component (AI) in the external preparation, $\alpha_I 2$ $(=[(CI-2)/(AI)])$ is, from the viewpoint of improving the adhesion suppressing effect, preferably 0.85 or less, more preferably 0.80 or less, even more preferably 0.75 or less, further more preferably 0.70 or less, and is, from the viewpoint of improving the feel in use in application to skin, preferably 0.01 or more, more preferably 0.02 or more, even more preferably 0.03 or more.

The ratio by mass of the total content of the component (BI) and the component (CI-2) to the content of the component (AI) in the external preparation, $\beta_I 2$ $(=[[(BI)+(CI-2)]/(AI)])$ is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $\alpha_I 2$ is 0.85 or less and 0.01 or more and the mass ratio $\beta_I 2$ is 9 or less and 0.01 or more, more preferably the mass ratio $\alpha_I 2$ is 0.80 or less and 0.01 or more and the mass ratio $\beta_I 2$ is 8 or less and 0.01 or more, even more preferably the mass ratio $\alpha_I 2$ is 0.75 or less and 0.02 or more and the mass ratio $\beta_I 2$ is 6 or less and 0.05 or more, further more preferably the mass ratio $\alpha_I 2$ is 0.70 or less and 0.03 or more and the mass ratio $\beta_I 2$ is 4 or less and 0.1 or more, further more preferably the mass ratio $\alpha_I 2$ is 0.70 or less and 0.03 or more and the mass ratio $\beta_I 2$ is 3 or less and 0.1 or more.

In the case where the external preparation further contains the component (CI-2), a preferred numerical range of the ratio by mass of the content of the component (C2) to the total content of the component (AI-1), the component (AI-2) and the component (AI-3) in the external preparation, $\alpha_I II$ $(=[(CI-2)/[(AI-1)+(AI-2)+(AI-3)]])$ is the same as the preferred numerical range of the mass ratio $\alpha_I 2$.

A preferred numerical range of the ratio by mass of the total content of the component (BI) and the component (CI-2) to the total content of the component (AI-1), the component (AI-2) and the component (AI-3) in the external preparation, $\beta_r II$ ($=[[(BI)+(CI-2)]/[(AI-1)+(AI-2)+(AI-3)]]$) is the same as the preferred numerical range of the mass ratio $\beta_r 2$.

From the viewpoint of improving the adhesion suppressing effect and from the viewpoint of improving the feel in use in application to skin, preferably the mass ratio $\alpha_1 II$ is 0.85 or less and 0.01 or more and the mass ratio $\beta_r II$ is 9 or less and 0.01 or more, more preferably the mass ratio $\alpha_r II$ is 0.80 or less and 0.01 or more and the mass ratio $\beta_r II$ is 8 or less and 0.01 or more, even more preferably the mass ratio $\alpha_r II$ is 0.75 or less and 0.02 or more and the mass ratio $\beta_r II$ is 6 or less and 0.05 or more, further more preferably the mass ratio $\alpha_r II$ is 0.70 or less and 0.03 or more and the mass ratio $\beta_r II$ is 4 or less and 0.1 or more, further more preferably the mass ratio $\alpha_r II$ is 0.70 or less and 0.03 or more and the mass ratio $\beta_r II$ is 3 or less and 0.1 or more.

In the case where the external preparation further contains the component (CI-1) and the component (CI-2), the ratio by mass of the total content of the component (CI-1) and the component (CI-2) to the content of the component (AI) in the external preparation, $\alpha_r(1-2)$ ($=[[(CI-1)+(CI-2)]/(AI)]$) is, from the viewpoint of improving the adhesion suppressing effect, preferably 3.5 or less, more preferably 3 or less, even more preferably 2.5 or less, further more preferably 2 or less, and is, from the viewpoint of improving the feel in use in application to skin, preferably 0.01 or more, more preferably 0.03 or more, even more preferably 0.05 or more, further more preferably 0.1 or more.

The ratio by mass of the total content of the component (BI), the component (CI-1) and the component (CI-2) to the content of the component (AI) in the external preparation, $\beta_r(1-2)$ ($=[[(BI)+(CI-1)+(CI-2)]/(AI)]$) is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $\alpha_r 2$ is 0.85 or less and 0.01 or more and the mass ratio $\alpha_r(1-2)$ is 3.5 or less and 0.01 or more and the mass ratio $\beta_r(1-2)$ is 9 or less and 0.01 or more, more preferably the mass ratio $\alpha_r 2$ is 0.80 or less and 0.01 or more and the mass ratio $\alpha_r(1-2)$ is 3 or less and 0.03 or more and the mass ratio $\beta_r(1-2)$ is 8 or less and 0.01 or more, even more preferably the mass ratio $\alpha_r 2$ is 0.75 or less and 0.02 or more and the mass ratio $\alpha_r(1-2)$ is 2.5 or less and 0.05 or more and the mass ratio $\beta_r(1-2)$ is 6 or less and 0.05 or more, further more preferably the mass ratio $\alpha_r 2$ is 0.70 or less and 0.03 or more and the mass ratio $\alpha_r(1-2)$ is 2 or less and 0.1 or more and the mass ratio $\beta_r(1-2)$ is 4 or less and 0.1 or more, further more preferably the mass ratio $\alpha_r 2$ is 0.70 or less and 0.03 or more and the mass ratio $\alpha_r(1-2)$ is 2 or less and 0.1 or more and the mass ratio $\beta_r(1-2)$ is 3 or less and 0.1 or more.

In the case where the external preparation further contains the component (CI-1) and the component (CI-2), a preferred numerical range of the ratio by mass of the total content of the component (CI-1) and the component (CI-2) to the total content of the component (AI-1), the component (AI-2) and the component (AI-3) in the external preparation, $\alpha_r(I-II)$ ($=[[(C1)+(C2)]/[(AI-1)+(AI-2)+(AI-3)]]$) is the same as the preferred numerical range of the mass ratio $\alpha_r(1-2)$.

A preferred numerical range of the ratio by mass of the total content of the component (BI), the component (CI-1) and the component (CI-2) to the total content of the component (AI-1), the component (AI-2) and the component (AI-3) in the external preparation, $\beta_r(I-II)$ ($=[[(BI)+(CI-1)+(CI-2)]/[(AI-1)+(AI-2)+(AI-3)]]$) is the same as the preferred numerical range of the mass ratio $\beta_r(1-2)$.

From the viewpoint of improving the adhesion suppressing effect and from the viewpoint of improving the feel in use in application to skin, preferably the mass ratio $\alpha_r II$ is 0.85 or less and 0.01 or more and the mass ratio $\alpha_r(I-II)$ is 3.5 or less and 0.01 or more and the mass ratio $\beta_r(I-II)$ is 9 or less and 0.01 or more, more preferably the mass ratio $\alpha_r II$ is 0.80 or less and 0.01 or more and the mass ratio $\alpha_r(I-II)$ is 3 or less and 0.03 or more and the mass ratio $\beta_r(I-II)$ is 8 or less and 0.01 or more, even more preferably the mass ratio $\alpha_r II$ is 0.75 or less and 0.02 or more and the mass ratio $\alpha_r(I-II)$ is 2.5 or less and 0.05 or more and the mass ratio $\beta_r(I-II)$ is 6 or less and 0.05 or more, further more preferably the mass ratio $\alpha_r II$ is 0.70 or less and 0.03 or more and the mass ratio $\alpha_r(I-II)$ is 2 or less and 0.1 or more and the mass ratio $\beta_r(I-II)$ is 4 or less and 0.1 or more, further more preferably the mass ratio $\alpha_r II$ is 0.70 or less and 0.03 or more and the mass ratio $\alpha_r(I-II)$ is 2 or less and 0.1 or more and the mass ratio $\beta_r(I-II)$ is 3 or less and 0.1 or more.

(Content of Component (CI-1))

In the case where the external preparation contains the component (CI-1), the content of the component (CI-1) in the external preparation is, from the viewpoint of improving the feel in use in application to skin, preferably 0.1% by mass or more, more preferably 1% by mass or more, even more preferably 3% by mass or more, further more preferably 5% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

(Content of Component (CI-2))

In the case where the external preparation contains the component (CI-2), the content of the component (CI-2) in the external preparation is, from the viewpoint of improving the feel in use in application to skin, preferably 0.1% by mass or more, more preferably 0.5% by mass or more, even more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mass or less.

The content and the mass ratio of each component in the external preparation in the third aspect of the invention are as follows.

(Content of Component (BII) in External Preparation)

The content of the component (BII) in the external preparation is, from the viewpoint of improving the feel in use in application to skin, preferably 0.05% by mass or more, more preferably 0.1% by mass or more, even more preferably 1% by mass or more, further more preferably 3% by mass or more, further more preferably 5% by mass or more, further more preferably 8% by mass or more, further more preferably 10% by mass or more, and is, from the same viewpoint as above and from the viewpoint of improving the adhesion suppressing effect, preferably 60% by mass or less, more preferably 50% by mass or less, even more preferably 40% by mass or less, further more preferably 30% by mas or less, further more preferably 25% by mass or less, further more preferably 20% by mass or less, further more preferably 18% by mass or less, further more preferably 16% by mass or less.

(Mass Ratio [(BII)/(AI)])

The ratio by mass of the content of the component (BII) to the content of the component (AI) in the external preparation [(BII)/(AI)] (hereinafter referred to as "$x_{II}1$") is, from the viewpoint of improving the adhesion suppressing effect, 3.5 or less, preferably 3 or less, more preferably 2.5 or less, even more preferably 2 or less, and is, from the viewpoint of improving the feel in use in application to skin, preferably 0.01 or more, more preferably 0.03 or more, even more preferably 0.05 or more, further more preferably 0.1 or more. More specifically, $x_{II}1$ is, from the viewpoint of improving the adhesion suppressing effect and from the viewpoint of improving the feel in use in application to skin, preferably 3.5 or less and 0.01 or more, more preferably 3 or less and 0.03 or more, even more preferably 2.5 or less and 0.05 or more, further more preferably 2 or less and 0.1 or more.

(Mass Ratio [(BII)/[(AI-1)+(AI-2)+(AI-3)]])

In the case where the component (AI) is at least one selected from the group consisting of the component (AI-1), the component (AI-2) and the component (AI-3), the ratio by mass of the content of the component (BII) to the total content of the component (AI-1), the component (AI-2) and the component (AI-3) in the external preparation, [(BII)/[(AI-1)+(AI-2)+(AI-3)] (hereinafter referred to as "$x_{II}I$") is, from the viewpoint of improving the adhesion suppressing effect, 3.5 or less, preferably 3 or less, more preferably 2.5 or less, even more preferably 2 or less, and is, from the viewpoint of improving the feel in use in application to skin, preferably 0.01 or more, more preferably 0.03 or more, even more preferably 0.05 or more, further more preferably 0.1 or more. More specifically, $x_{II}I$ is, from the viewpoint of improving the adhesion suppressing effect and from the viewpoint of improving the feel in use in application to skin, preferably 3.5 or less and 0.01 or more, more preferably 3 or less and 0.03 or more, even more preferably 2.5 or less and 0.05 or more, further more preferably 2 or less and 0.1 or more.

In the case where the external preparation further contains the component (CII-1) (ester oil), the ratio by mass of the total content of the component (BII) and the component (CII-1) to the content of the component (A) in the external preparation, $\beta_{II}1$ (=[[(BII)+(CII-1)]/(AI)]) is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $x_{II}1$ is 3.5 or less and 0.01 or more and the mass ratio $\beta_{II}1$ is 9 or less and 0.01 or more, more preferably the mass ratio $x_{II}1$ is 3 or less and 0.03 or more and the mass ratio $\beta_{II}1$ is 8 or less and 0.01 or more, even more preferably the mass ratio $x_{II}1$ is 2.5 or less and 0.05 or more and the mass ratio $\beta_{II}1$ is 6 or less and 0.05 or more, further more preferably the mass ratio $x_{II}1$ is 2 or less and 0.1 or more and the mass ratio $\beta_{II}1$ is 4 or less and 0.1 or more, further more preferably the mass ratio $x_{II}1$ is 2 or less and 0.1 or more and the mass ratio $\beta_{II}1$ is 3 or less and 0.1 or more.

In the case where the external preparation further contains the component (CII-1), a preferred numerical range of the ratio by mass of the total content of the component (BII) and the component (CI-1) to the total content of the component (A-1), the component (A-2) and the component (A-3) in the external preparation, $\beta_{II}I$ (=[[(BII)+(CII-1)]/[(AI-1)+(AI-2)+(AI-3)]]) is the same as the preferred numerical range of the mass ratio $\beta_{II}1$.

From the viewpoint of improving the adhesion suppressing effect and from the viewpoint of improving the feel in use in application to skin, preferably the mass ratio $x_{II}I$ is 3.5 or less and 0.01 or more and the mass ratio $\beta_{II}I$ is 9 or less and 0.01 or more, more preferably the mass ratio $x_{II}I$ is 3 or less and 0.03 or more and the mass ratio $\beta_{II}I$ is 8 or less and 0.01 or more, even more preferably the mass ratio $x_{II}I$ is 2.5 or less and 0.05 or more and the mass ratio $\beta_{II}I$ is 6 or less and 0.05 or more, further more preferably the mass ratio $x_{II}I$ is 2 or less and 0.1 or more and the mass ratio $\beta_{II}I$ is 4 or less and 0.1 or more, further more preferably the mass ratio $x_{II}I$ is 2 or less and 0.1 or more and the mass ratio $\beta_{II}I$ is 3 or less and 0.1 or more.

In the case where the external preparation further contains the component (CII-2) (nonvolatile silicone oil), the ratio by mass of the content of the component (CII-2) to the content of the component (AI) in the external preparation, $\alpha_{II}2$ (=[(CII-2)/(AI)]) is, from the viewpoint of improving the adhesion suppressing effect, preferably 0.85 or less, more preferably 0.80 or less, even more preferably 0.75 or less, further more preferably 0.70 or less, and is, from the viewpoint of improving the feel in use in application to skin, preferably 0.01 or more, more preferably 0.02 or more, even more preferably 0.03 or more.

The ratio by mass of the total content of the component (BII) and the component (CII-2) to the content of the component (AI) in the external preparation, $\beta_{II}2$ (=[[(BII)+(CII-2)]/(AI)]) is, from the viewpoint of improving the adhesion suppressing effect, preferably 3.5 or less, more preferably 3 or less, even more preferably 2.5 or less, further more preferably 2 or less, and is, from the viewpoint of improving the feel in use in application to skin, preferably 0.01 or more, more preferably 0.03 or more, even more preferably 0.05 or more, further more preferably 0.1 or more.

From the viewpoint of improving the adhesion suppressing effect and from the viewpoint of improving the feel in use in application to skin, preferably the mass ratio $\alpha_{II}2$ is 0.85 or less and 0.01 or more and the mass ratio $\beta_{II}2$ is 3.5 or less and 0.01 or more, more preferably the mass ratio $\alpha_{II}2$ is 0.80 or less and 0.01 or more and the mass ratio $\beta_{II}2$ is 3 or less and 0.03 or more, even more preferably the mass ratio $\alpha_{II}2$ is 0.75 or less and 0.02 or more and the mass ratio $\beta_{II}2$ is 2.5 or less and 0.05 or more, further more preferably the mass ratio $\alpha_{II}2$ is 0.70 or less and 0.03 or more and the mass ratio $\beta_{II}2$ is 2 or less and 0.1 or more.

In the case where the external preparation further contains the component (CII-2), a preferred numerical range of the ratio by mass of the content of the component (CII-2) to the total content of the component (AI-1), the component (AI-2) and the component (AI-3) in the external preparation, $\alpha_{II}II$ (=[(CII-2)/[(AI-1)+(AI-2)+(AI-3)]]) is the same as the preferred numerical range of the mass ratio $\alpha_{II}2$.

A preferred numerical range of the ratio by mass of the total content of the component (BII) and the component (CII-2) to the total content of the component (AI-1), the component (AI-2) and the component (AI-3) in the external preparation, $\beta_{II}$II (=[[(BII)+(CII-2)]/[(AI-1)+(AI-2)+(AI-3)]]) is the same as the preferred numerical range of the mass ratio $\beta_{II}$2.

From the viewpoint of improving the adhesion suppressing effect and from the viewpoint of improving the feel in use in application to skin, preferably the mass ratio $\alpha_{II}$II is 0.85 or less and 0.01 or more and the mass ratio $\beta_{II}$II is 3.5 or less and 0.01 or more, more preferably the mass ratio $\alpha_{II}$II is 0.80 or less and 0.01 or more and the mass ratio $\beta_{II}$II is 3 or less and 0.03 or more, even more preferably the mass ratio $\alpha_{II}$II is 0.75 or less and 0.02 or more and the mass ratio $\beta_{II}$II is 2.5 or less and 0.05 or more, further more preferably the mass ratio $\alpha_{II}$II is 0.70 or less and 0.03 or more and the mass ratio $\beta_{II}$II is 2 or less and 0.1 or more.

In the case where the external preparation further contains the component (CII-1) and the component (CII-2), the ratio by mass of the total content of the component (BII), the component (CII-1) and the component (CII-2) to the content of the component (AI) in the external preparation, $\beta_{II}$(1-2) (=[[(BII)+(CII-1)+(CII-2)]/(AI)]) is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $\alpha_{II}$2 is 0.85 or less and 0.01 or more and the mass ratio $\beta_{II}$2 is 3.5 or less and 0.01 or more and the mass ratio $\beta_{II}$(1-2) is 9 or less and 0.01 or more, more preferably the mass ratio $\alpha_{II}$2 is 0.80 or less and 0.01 or more and the mass ratio $\beta_{II}$2 is 3 or less and 0.03 or more and the mass ratio $\beta_{II}$(1-2) is 8 or less and 0.01 or more, even more preferably the mass ratio $\alpha_{II}$2 is 0.75 or less and 0.02 or more and the mass ratio $\beta_{II}$2 is 2.5 or less and 0.05 or more and the mass ratio $\beta_{II}$(1-2) is 6 or less and 0.05 or more, further more preferably the mass ratio $\alpha_{II}$2 is 0.70 or less and 0.03 or more and the mass ratio $\beta_{II}$2 is 2 or less and 0.1 or more and the mass ratio $\beta_{II}$(1-2) is 4 or less and 0.1 or more, further more preferably the mass ratio $\alpha_{II}$2 is 0.70 or less and 0.03 or more and the mass ratio $\beta_{II}$2 is 2 or less and 0.1 or more and the mass ratio $\beta_{II}$(1-2) is 3 or less and 0.1 or more.

In the case where the external preparation further contains the component (CII-1) and the component (CII-2), a preferred numerical range of the ratio by mass of the total content of the the component (BII), the component (CII-1) and the component (CII-2) to the total content of the component (AI-1), the component (AI-2) and the component (AI-3) in the external preparation, $\beta_{II}$(I-II) (=[[(BII)+(CII-1)+(CII-2)]/[(AI-1)+(AI-2)+(AI-3)]]) is the same as the preferred numerical range of the mass ratio $\beta_{II}$(1-2).

From the viewpoint of improving the adhesion suppressing effect and from the viewpoint of improving the feel in use in application to skin, preferably the mass ratio $\alpha_{II}$II is 0.85 or less and 0.01 or more and the mass ratio $\beta_{II}$II is 3.5 or less and 0.01 or more and the mass ratio $\beta_{II}$(I-II) is 9 or less and 0.01 or more, more preferably the mass ratio $\alpha_{II}$II is 0.80 or less and 0.01 or more and the mass ratio $\beta_{II}$II is 3 or less and 0.03 or more and the mass ratio $\beta_{II}$(I-II) is 8 or less and 0.01 or more, even more preferably the mass ratio $\alpha_{II}$II is 0.75 or less and 0.02 or more and the mass ratio $\beta_{II}$II is 2.5 or less and 0.05 or more and the mass ratio $\beta_{II}$(I-II) is 6 or less and 0.05 or more, further more preferably the mass ratio $\alpha_{II}$II is 0.70 or less and 0.03 or more and the mass ratio $\beta_{II}$II is 2 or less and 0.1 or more and the mass ratio $\beta_{II}$(I-II) is 4 or less and 0.1 or more, further more preferably the mass ratio $\alpha_{II}$II is 0.70 or less and 0.03 or more and the mass ratio $\beta_{II}$II is 2 or less and 0.1 or more and the mass ratio $\beta_{II}$(I-II) is 3 or less and 0.1 or more.

(Content of Component (CII-1))

In the case where the external preparation contains the component (CII-1), the content of the component (CII-1) in the external preparation is, from the viewpoint of improving the feel in use in application to skin, preferably 0.1% by mass or more, more preferably 1% by mass or more, even more preferably 3% by mass or more, and is, from the same viewpoint and from the viewpoint of improving the adhesion suppressing effect, preferably 25% by mass or less, more preferably 20% by mass or less, even more preferably 18% by mass or less, further more preferably 16% by mass or less.

(Content of Component (CII-2))

In the case where the external preparation contains the component (CII-2), the content of the component (CII-2) in the external preparation is, from the viewpoint of improving the feel in use in application to skin, preferably 0.1% by mass or more, more preferably 0.5% by mass or more, even more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mass or less.

The content and the mass ratio of each component in the external preparation in the fourth aspect of the invention are as follows.

(Content of Component (BIII) in External Preparation)

The content of the component (BIII) in the external preparation is, from the viewpoint of improving the feel in use in application to skin, preferably 0.05% by mass or more, more preferably 0.1% by mass or more, even more preferably 0.5% by mass or more, further more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mas or less.

(Mass Ratio [(BIII)/(AI)])

The ratio by mass of the content of the component (BIII) to the content of the component (AI) in the external preparation [(BIII)/(AI)] (hereinafter referred to as "$x_{III}$1") is, from the viewpoint of improving the adhesion suppressing effect, 0.85 or less, preferably 0.80 or less, more preferably 0.75 or less, even more preferably 0.70 or less, and is, from the viewpoint of improving the feel in use in application to skin, preferably 0.01 or more, more preferably 0.02 or more, even more preferably 0.03 or more. More specifically, $x_{III}$1 is, from the viewpoint of improving the adhesion suppressing effect and from the viewpoint of improving the feel in use in application to skin, preferably 0.85 or less and 0.01 or more, more preferably 0.80 or less and 0.01 or more, even more preferably 0.75 or less and 0.02 or more, further more preferably 0.70 or less and 0.03 or more.

(Mass Ratio [(BIII)/[(AI-1)+(AI-2)+(AI-3)]])

In the case where the component (AIII) is at least one selected from the group consisting of the component (AI-1), the component (AI-2) and the component (AI-3), the ratio by mass of the content of the component (BIII) to the total content of the component (AI-1), the component (AI-2) and the component (AI-3) in the external preparation, [(BIII)/[(AI-1)+(AI-2)+(AI-3)]] (hereinafter referred to as "$x_{III}$I") is, from the viewpoint of improving the adhesion suppressing effect, 0.85 or less, preferably 0.80 or less, more preferably 0.75 or less, even more preferably 0.70 or less, and is, from the viewpoint of improving the feel in use in application to skin, preferably 0.01 or more, more preferably 0.02 or more, even more preferably 0.03 or more. More specifically, $x_{III}1$ is, from the viewpoint of improving the adhesion suppressing effect and from the viewpoint of improving the feel in use in application to skin, preferably 0.85 or less and 0.01 or more, more preferably 0.80 or less and 0.01 or more, even more preferably 0.75 or less and 0.02 or more, further more preferably 0.70 or less and 0.03 or more.

In the case where the external preparation further contains the component (CIII-1) (ester oil), the ratio by mass of the total content of the component (BIII) and the component (CIII-1) to the content of the component (AI) in the external preparation, $\beta_{III}1$ (=[[(BIII)+(CIII-1)]/(AI)]) is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $x_{III}1$ is 0.85 or less and 0.01 or more and the mass ratio $\beta_{III}1$ is 9 or less and 0.01 or more, more preferably the mass ratio $x_{III}1$ is 0.80 or less and 0.01 or more and the mass ratio $\beta_{III}1$ is 8 or less and 0.01 or more, even more preferably the mass ratio $x_{III}1$ is 0.75 or less and 0.02 or more and the mass ratio $\beta_{III}1$ is 6 or less and 0.05 or more, further more preferably the mass ratio $x_{III}1$ is 0.70 or less and 0.03 or more and the mass ratio $\beta_{III}1$ is 4 or less and 0.1 or more, further more preferably the mass ratio $x_{III}1$ is 0.70 or less and 0.03 or more and the mass ratio $\beta_{III}1$ is 3 or less and 0.1 or more.

In the case where the external preparation further contains the component (CIII-1), a preferred numerical range of the ratio by mass of the total content of the component (BIII) and the component (CIII-1) to the total content of the component (AI-1), the component (AI-2) and the component (AI-3) in the external preparation, $\beta_{III}I$ (=[[(BIII)+(CIII-1)]/[(AI-1)+(AI-2)+(AI-3)]]) is the same as the preferred numerical range of the mass ratio $\beta_{III}1$.

From the viewpoint of improving the adhesion suppressing effect and from the viewpoint of bettering the feel in use in application to skin, preferably the mass ratio $x_{III}I$ is 0.85 or less and 0.01 or more and the mass ratio $\beta_{III}I$ is 9 or less and 0.01 or more, more preferably the mass ratio $x_{III}I$ is 0.80 or less and 0.01 or more and the mass ratio $\beta_{III}I$ is 8 or less and 0.01 or more, even more preferably the mass ratio $x_{III}I$ is 0.75 or less and 0.02 or more and the mass ratio $\beta_{III}I$ is 6 or less and 0.05 or more, further more preferably the mass ratio $x_{III}I$ is 0.70 or less and 0.03 or more and the mass ratio $\beta_{III}I$ is 4 or less and 0.1 or more, further more preferably the mass ratio $x_{III}I$ is 0.70 or less and 0.03 or more and the mass ratio $\beta_{III}I$ is 3 or less and 0.1 or more.

In the case where the external preparation further contains the component (CIII-2) (nonvolatile hydrocarbon oil), the ratio by mass of the total content of the component (BIII) and the component (CIII-2) to the content of the component (AI) in the external preparation, $\beta_{III}2$ (=[[(BIII)+(CIII-2)]/(AI)]) is, from the viewpoint of improving the adhesion suppressing effect, preferably 3.5 or less, more preferably 3 or less, even more preferably 2.5 or less, further more preferably 2 or less, and is, from the viewpoint of improving the feel in use in application to skin, preferably 0.01 or more, more preferably 0.03 or more, even more preferably 0.05 or more, further more preferably 0.1 or more.

From the viewpoint of improving the adhesion suppressing effect and from the viewpoint of improving the feel in use in application to skin, preferably the mass ratio $x_{III}1$ is 0.85 or less and 0.01 or more and the mass ratio $\beta_{III}2$ is 3.5 or less and 0.01 or more, more preferably the mass ratio $x_{III}1$ is 0.80 or less and 0.01 or more and the mass ratio $\beta_{III}2$ is 3 or less and 0.03 or more, even more preferably the mass ratio $x_{III}1$ is 0.75 or less and 0.02 or more and the mass ratio $\beta_{III}2$ is 2.5 or less and 0.05 or more, further more preferably the mass ratio $x_{III}1$ is 0.70 or less and 0.03 or more and the mass ratio $\beta_{III}2$ is 2 or less and 0.1 or more.

In the case where the external preparation further contains the component (CIII-2), a preferred numerical range of the ratio by mass of the total content of the component (BIII) and the component (CIII-2) to the total content of the component (AI-1), the component (AI-2) and the component (AI-3) in the external preparation, $\beta_{III}II$ (=[[(BIII)+(CIII-2)]/[(AI-1)+(AI-2)+(AI-3)]]) is the same as the preferred numerical range of the mass ratio $\beta_{III}2$.

From the viewpoint of improving the adhesion suppressing effect and from the viewpoint of improving the feel in use in application to skin, preferably the mass ratio $x_{III}I$ is 0.85 or less and 0.01 or more and the mass ratio $\beta_{III}II$ is 3.5 or less and 0.01 or more, more preferably the mass ratio $x_{III}I$ is 0.80 or less and 0.01 or more and the mass ratio $\beta_{III}II$ is 3 or less and 0.03 or more, even more preferably the mass ratio $x_{III}I$ is 0.75 or less and 0.02 or more and the mass ratio $\beta_{III}II$ is 2.5 or less and 0.05 or more, further more preferably the mass ratio $x_{III}I$ is 0.70 or less and 0.03 or more and the mass ratio $\beta_{III}II$ is 2 or less and 0.1 or more.

In the case where the external preparation further contains the component (CIII-1) and the component (CIII-2), the ratio by mass of the total content of the component (BIII), the component (CIII-1) and the component (CIII-2) to the content of the component (AI) in the external preparation, $\beta_{III}(1-2)$ (=[[(BIII)+(CIII-1)+(CIII-2)]/(AI)]) is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

From the viewpoint of improving the adhesion suppressing effect and from the viewpoint of improving the feel in use in application to skin, preferably the mass ratio $x_{III}1$ is 0.85 or less and 0.01 or more and the mass ratio $\beta_{III}2$ is 3.5 or less and 0.01 or more and the mass ratio $\beta_{III}(1-2)$ is 9 or less and 0.01 or more, more preferably the mass ratio $x_{III}1$ is 0.80 or less and 0.01 or more and the mass ratio $\beta_{III}2$ is 3 or less and 0.03 or more and the mass ratio $\beta_{III}(1-2)$ is 8 or less and 0.01 or more, even more preferably the mass ratio $x_{III}1$ is 0.75 or less and 0.02 or more and the mass ratio $\beta_{III}2$ is 2.5 or less and 0.05 or more and the mass ratio $\beta_{III}(1-2)$ is 6 or less and 0.05 or more, further more preferably the mass ratio $x_{III}1$ is 0.70 or less and 0.03 or more and the mass ratio $\beta_{III}2$ is 2 or less and 0.1 or more and the mass ratio $\beta_{III}(1-2)$ is 4 or less and 0.1 or more, further more preferably the mass ratio $x_{III}1$ is 0.70 or less and 0.03 or more and the mass ratio $\beta_{III}2$ is 2 or less and 0.1 or more and the mass ratio $\beta_{III}(1-2)$ is 3 or less and 0.1 or more.

In the case where the external preparation further contains the component (CIII-1) and the component (CIII-2), a preferred numerical range of the ratio by mass of the total content of the the component (BIII), the component (CIII-1)

and the component (CIII-2) to the total content of the component (AI-1), the component (AI-2) and the component (AI-3) in the external preparation, $\beta_{III}$(I-II) (=[[(BIII)+(CIII-1)+(CIII-2)]/[(AI-1)+(AI-2)+(AI-3)]]) is the same as the preferred numerical range of the mass ratio $\beta_{III}$(1-2).

From the viewpoint of improving the adhesion suppressing effect and from the viewpoint of improving the feel in use in application to skin, preferably the mass ratio $x_{III}$I is 0.85 or less and 0.01 or more and the mass ratio $\beta_{III}$II is 3.5 or less and 0.01 or more and the mass ratio $\beta_{III}$(I-II) is 9 or less and 0.01 or more, more preferably the mass ratio $x_{III}$I is 0.80 or less and 0.01 or more and the mass ratio $\beta_{III}$II is 3 or less and 0.03 or more and the mass ratio $\beta_{III}$(I-II) is 8 or less and 0.01 or more, even more preferably the mass ratio $x_{III}$I is 0.75 or less and 0.02 or more and the mass ratio $\beta_{III}$II is 2.5 or less and 0.05 or more and the mass ratio $\beta_{III}$(I-II) is 6 or less and 0.05 or more, further more preferably the mass ratio $x_{III}$I is 0.70 or less and 0.03 or more and the mass ratio $\beta_{III}$II is 2 or less and 0.1 or more and the mass ratio $\beta_{III}$(I-II) is 4 or less and 0.1 or more, further more preferably the mass ratio $x_{III}$I is 0.70 or less and 0.03 or more and the mass ratio $\beta_{III}$II is 2 or less and 0.1 or more and the mass ratio $\beta_{III}$(I-II) is 3 or less and 0.1 or more.

(Content of Component (CIII-1))

In the case where the external preparation contains the component (CIII-1), the content of the component (CIII-1) in the external preparation is, from the viewpoint of improving the feel in use in application to skin, preferably 0.1% by mass or more, more preferably 1% by mass or more, even more preferably 3% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

(Content of Component (CIII-2))

In the case where the external preparation contains the component (CIII-2), the content of the component (CIII-2) in the external preparation is, from the viewpoint of bettering the feel in use in application to skin, preferably 0.1% by mass or more, more preferably 1% by mass or more, even more 3% by mass or more, further more preferably 5% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

(Content of Component (D))

In the second aspect of the invention where the external preparation contains the component (D), the content of the component (D) in the external preparation is, from the viewpoint of improving the adhesion suppressing effect, preferably 20% by mass or more, more preferably 25% by mass or more, even more preferably 30% by mass or more, and is preferably 95% by mass or less, more preferably 90% by mass or less, even more preferably 85% by mass or less.

In the third aspect of the invention and the fourth aspect of the invention where the external preparation contains the component (D), the content of the component (D) in the external preparation is, from the viewpoint of improving the adhesion suppressing effect, preferably 20% by mass or more, more preferably 25% by mass or more, even more preferably 30% by mass or more, and is preferably 97% by mass or less, more preferably 95% by mass or less, even more preferably 93% by mass or less.

The form of the external preparation in the second to fourth aspects of the invention incudes an oil-based type having one oily phase as a dispersion medium, an oil-in-water type (hereinafter also referred to as "O/W type") and a water-in-oil type (hereinafter also referred to as "W/O type"), and these can be appropriately selected.

In the second to fourth aspects of the invention, the external preparation can be used as an external preparation applied to the skin and the hair and is, from the viewpoint of the adhesion suppressing effect, preferably cosmetic materials, more preferably skin cosmetic materials.

The preparation form of the external preparation is not specifically limited, and may be in any preparation form of a liquid form, a foamy form, a paste form, a cream form, or a solid form.

In the second to fourth aspects of the invention where the form of the preparation is an oil-based type, the content and the mass ratio of each component therein are as described above. In the case where the external preparation is a W/O type or an O/W type, the content and the mass ratio of each component therein are as described below.

(Content and Mass Ratio of Component in Water-In-Oil (W/O) Type Preparation)

In the second to fourth aspects of the invention where the external preparation is a W/O type form, the content of the component (AI) in the external preparation is, from the viewpoint of improving the adhesion suppressing effect, preferably 1% by mass or more, more preferably 2% by mass or more, even more preferably 3% by mass or more, further more preferably 5% by mass or more, further more preferably 8% by mass or more, further more preferably 10% by mass or more, and is, from the viewpoint of improving the feel in use in application to skin and from the viewpoint of economy, preferably 40% by mass or less, more preferably 35% by mass or less, even more preferably 30% by mass or less.

In the second to fourth aspects of the invention where the external preparation is a W/O type form, the total content of the component (AI-1), the component (AI-2) and the component (AI-3) in the external preparation is, from the viewpoint of improving the adhesion suppressing effect, preferably 1% by mass or more, more preferably 2% by mass or more, even more preferably 3% by mass or more, further more preferably 5% by mass or more, further more preferably 8% by mass or more, further more preferably 10% by mass or more, and is, from the viewpoint of improving the feel in use in application to skin and from the viewpoint of economy, preferably 40% by mass or less, more preferably 35% by mass or less, even more preferably 30% by mass or less.

In the second aspect of the invention where the external preparation is a W/O type form, the content and the mass ratio of each component in the external preparation are as described below.

In the W/O type external preparation, the content of the component (BI) in the external preparation is, from the viewpoint of improving the feel in use in application to skin, preferably 0.05% by mass or more, more preferably 0.1% by mass or more, even more preferably 1% by mass or more, further more preferably 3% by mass or more, and is, from the viewpoint of improving the adhesion suppressing effect and from the viewpoint of improving the feel in use in application to skin, preferably 30% by mass or less, more preferably 25% by mass or less, even more preferably 20% by mass or less, further more preferably 18% by mass or less, further more preferably 16% by mass or less.

In the case where the external preparation is a W/O type form, the ratio by mass of the content of the component (BI) to the component (AI) in the external preparation, [(BI)/

(AI)] is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

In the case where the external preparation is a W/O type form and where the component (AI) is at least one selected from the group consisting of the component (AI-1), the component (AI-2) and the component (AI-3), the ratio by mass of the content of the component (BI) to the total content of the component (AI-1), the component (AI-2) and the component (AI-3) in the external preparation, [(BI)/[(AI-1)+(AI-2)+(AI-3)]] is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more.

In the case where the external preparation is a W/O type form and where the external preparation contains the component (CI-1), the content of the component (CI-1) in the external preparation is, from the viewpoint of improving the feel in use in application to skin, preferably 0.1% by mass or more, more preferably 1% by mass or more, even more preferably 3% by mass or more, further more preferably 5% by mass or more, further more preferably 8% by mass or more, and is, from the same viewpoint as above and from the viewpoint of improving the adhesion suppressing effect, preferably 25% by mass or less, more preferably 20% by mass or less, even more preferably 16% by mass or less, further more preferably 12% by mass or less.

In the case where the external preparation is a W/O type form and where the external preparation contains the component (CI-2), the content of the component (CI-2) in the external preparation is, from the viewpoint of improving the feel in use in application to skin, preferably 0.1% by mass or more, more preferably 0.5% by mass or more, even more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mass or less.

In the third aspect of the invention where the external preparation is a W/O type form, the content and the mass ratio of each component in the external preparation are as described below.

In the W/O type external preparation, the content of the component (BII) in the external preparation is, from the viewpoint of improving the feel in use in application to skin, preferably 0.05% by mass or more, more preferably 0.1% by mass or more, even more preferably 1% by mass or more, further more preferably 3% by mass or more, further more preferably 5% by mass or more, further more preferably 8% by mass or more, and is, from the viewpoint of improving the adhesion suppressing effect and from the viewpoint of improving the feel in use in application to skin, preferably 30% by mass or less, more preferably 25% by mass or less, even more preferably 20% by mass or less, further more preferably 16% by mass or less, further more preferably 12% by mass or less.

In the case where the external preparation is a W/O type form, the ratio by mass of the content of the component (BII) to the component (AI) in the external preparation, [(BII)/(AI)] is, from the viewpoint of improving the adhesion suppressing effect, 3.5 or less, preferably 3 or less, more preferably 2.5 or less, even more preferably 2 or less, and is, from the viewpoint of improving the feel in use in application to skin, preferably 0.01 or more, more preferably 0.03 or more, even more preferably 0.05 or more, further more preferably 0.1 or more.

In the case where the external preparation is a W/O type form and where the component (AI) is at least one selected from the group consisting of the component (AI-1), the component (AI-2) and the component (AI-3), the ratio by mass of the content of the component (BII) to the total content of the component (AI-1), the component (AI-2) and the component (AI-3) in the external preparation, [(BII)/[(AI-1)+(AI-2)+(AI-3)]] is, from the viewpoint of improving the adhesion suppressing effect, 3.5 or less, preferably 3 or less, more preferably 2.5 or less, even more preferably 2 or less, and is, from the viewpoint of improving the feel in use in application to skin, preferably 0.01 or more, more preferably 0.03 or more, even more preferably 0.05 or more, further more preferably 0.1 or more.

In the case where the external preparation is a W/O type form and where the external preparation contains the component (CII-1), the content of the component (CII-1) in the external preparation is, from the viewpoint of improving the feel in use in application to skin, preferably 0.1% by mass or more, more preferably 1% by mass or more, even more preferably 3% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

In the case where the external preparation is a W/O type form and where the external preparation contains the component (CII-2), the content of the component (CII-2) in the external preparation is, from the viewpoint of improving the feel in use in application to skin, preferably 0.1% by mass or more, more preferably 0.5% by mass or more, even more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mass or less.

In the fourth aspect of the invention where the external preparation is a W/O type form, the content and the mass ratio of each component in the external preparation are as described below.

In the W/O type external preparation, the content of the component (BIII) in the external preparation is, from the viewpoint of improving the feel in use in application to skin, preferably 0.05% by mass or more, more preferably 0.1% by mass or more, even more preferably 0.5% by mass or more, further more preferably 1% by mass or more, and is, from the viewpoint of improving the adhesion suppressing effect and from the viewpoint of the feel in use such as stickiness, preferably 15% by mass or less, more preferably 10% by mass or less, even more preferably 8% by mass or less, further more preferably 6% by mass or less.

In the case where the external preparation is a W/O type form, the ratio by mass of the content of the component (BIII) to the component (AI) in the external preparation, [(BIII)/(AI)] is, from the viewpoint of improving the adhesion suppressing effect, 0.85 or less, preferably 0.80 or less, more preferably 0.75 or less, even more preferably 0.70 or less, and is, from the viewpoint of improving the feel in use in application to skin, preferably 0.01 or more, more preferably 0.02 or more, even more preferably 0.03 or more.

In the case where the external preparation is a W/O type form and where the component (AI) is at least one selected from the group consisting of the component (AI-1), the component (AI-2) and the component (AI-3), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.85 or less, preferably 0.80 or less, more preferably 0.75 or less, even more preferably 0.70 or less, and is, from the viewpoint of improving the feel in use in application to skin, preferably 0.01 or more, more preferably 0.02 or more, even more preferably 0.03 or more.

In the case where the external preparation is a W/O type form and where the external preparation contains the component (CIII-1), the content of the component (CIII-1) in the external preparation is, from the viewpoint of improving the feel in use in application to skin, preferably 0.1% by mass or more, more preferably 1% by mass or more, even more preferably 3% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

In the case where the external preparation is a W/O type form and where the external preparation contains the component (CIII-2), the content of the component (CIII-2) in the external preparation is, from the viewpoint of improving the feel in use in application to skin, preferably 0.1% by mass or more, more preferably 1% by mass or more, even more preferably 3% by mass or more, further more preferably 5% by mass or more, further more preferably 8% by mass or more, and is, from the same viewpoint as above and from the viewpoint of improving the adhesion suppressing effect, preferably 25% by mass or less, more preferably 20% by mass or less, even more preferably 16% by mass or less, further more preferably 12% by mass or less.

In the second to fourth aspects of the invention where the external preparation is a W/O type form and where the external preparation contains the component (D), the content of the component (D) in the external preparation is, from the viewpoint of improving the adhesion suppressing effect, preferably 20% by mass or more, more preferably 25% by mass or more, even more preferably 30% by mass or more, and is preferably 70% by mass or less, more preferably 60% by mass or less, even more preferably 50% by mass or less.

(Content and Mass Ratio of Component in Oil-In-Water (O/W) Type Preparation)

In the second to fourth aspects of the invention where the external preparation is an O/W type form, the content of the component (AI) in the external preparation is, from the viewpoint of improving the adhesion suppressing effect, preferably 1% by mass or more, more preferably 2% by mass or more, even more preferably 3% by mass or more, and is, from the viewpoint of improving the feel in use in application to skin and from the viewpoint of economy, preferably 40% by mass or less, more preferably 35% by mass or less, even more preferably 30% by mass or less, further more preferably 20% by mass or less, further more preferably 15% by mass or less.

In the second to fourth aspects of the invention where the external preparation is an O/W type form, the total content of the component (AI-1), the component (AI-2) and the component (AI-3) in the external preparation is, from the viewpoint of improving the adhesion suppressing effect, preferably 1% by mass or more, more preferably 2% by mass or more, even more preferably 3% by mass or more, and is, from the viewpoint of improving the feel in use in application to skin and from the viewpoint of economy, preferably 40% by mass or less, more preferably 35% by mass or less, even more preferably 30% by mass or less, further more preferably 20% by mass or less, further more preferably 15% by mass or less.

In the second aspect of the invention where the external preparation is an O/W type form, the content and the mass ratio of each component in the external preparation are as described below.

In the O/W type external preparation, the content of the component (BI) in the external preparation is, from the viewpoint of improving the feel in use in application to skin, preferably 0.05% by mass or more, more preferably 0.1% by mass or more, even more preferably 1% by mass or more, further more preferably 3% by mass or more, further more preferably 5% by mass or more, further more preferably 8% by mass or more, further more preferably 10% by mass or more, and is, from the viewpoint of improving the adhesion suppressing effect and from the viewpoint of the feel in use as the external preparation such as stickiness, preferably 30% by mass or less, more preferably 25% by mass or less, even more preferably 20% by mass or less, further more preferably 18% by mass or less, further more preferably 16% by mass or less.

In the case where the external preparation is an O/W type form, the ratio by mass of the content of the component (BI) to the component (AI) in the external preparation, [(BI)/(AI)] is, from the viewpoint of improving the adhesion suppressing effect, 9 or less, preferably 8 or less, more preferably 6 or less, even more preferably 4 or less, further more preferably 3 or less, and is, from the viewpoint of improving the feel in use in application to skin, preferably 0.01 or more, more preferably 0.05 or more, even more preferably 0.1 or more, further more preferably 0.2 or more.

In the case where the external preparation is an O/W type form and where the component (AI) is one or more selected from the component (AI-1), the component (AI-2) and the component (AI-3), the ratio by mass of the content of the component (BI) to the total content of the component (AI-1), the component (AI-2) and the component (AI-3) in the external preparation, [(BI)/[(AI-1)+(AI-2)+(AI-3)]] is, from the viewpoint of improving the adhesion suppressing effect, preferably 9 or less, more preferably 8 or less, even more preferably 6 or less, further more preferably 4 or less, further more preferably 3 or less, and is, from the viewpoint of improving the feel in use in application to skin, preferably 0.01 or more, more preferably 0.05 or more, even more preferably 0.1 or more, further more preferably 0.2 or more.

In the case where the external preparation is an O/W type form and where the external preparation contains the component (CI-1), the content of the component (CI-1) in the external preparation is, from the viewpoint of improving the feel in use in application to skin, preferably 0.1% by mass or more, more preferably 1% by mass or more, even more preferably 3% by mass or more, further more preferably 5% by mass or more, further more preferably 8% by mass or more, further more preferably 10% by mass or more, and is, from the same viewpoint as above and from the viewpoint of improving the adhesion suppressing effect, preferably 25% by mass or less, more preferably 20% by mass or less, even more preferably 16% by mass or less.

In the case where the external preparation is an O/W type form and where the external preparation contains the component (CI-2), the content of the component (CI-2) in the external preparation is, from the viewpoint of improving the feel in use in application to skin, preferably 0.1% by mass or more, more preferably 0.5% by mass or more, even more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mass or less.

In the third aspect of the invention where the external preparation is an O/W type form, the content and the mass ratio of each component in the external preparation are as described below.

In the O/W type external preparation, the content of the component (BII) in the external preparation is, from the viewpoint of improving the feel in use in application to skin, preferably 0.05% by mass or more, more preferably 0.1% by mass or more, even more preferably 1% by mass or more, further more preferably 3% by mass or more, further more preferably 5% by mass or more, further more preferably 8% by mass or more, further more preferably 10% by mass or more, and is, from the viewpoint of improving the adhesion suppressing effect and from the viewpoint of the feel in use such as stickiness, preferably 30% by mass or less, more preferably 25% by mass or less, even more preferably 20% by mass or less, further more preferably 16% by mass or less.

In the case where the external preparation is an O/W type form, the ratio by mass of the content of the component (BII) to the component (AI) in the external preparation, [(BII)/(AI)] is, from the viewpoint of improving the adhesion suppressing effect, 3.5 or less, preferably 3 or less, more preferably 2.5 or less, even more preferably 2 or less, and is, from the viewpoint of improving the feel in use in application to skin, preferably 0.01 or more, more preferably 0.03 or more, even more preferably 0.05 or more, further more preferably 0.1 or more.

In the case where the external preparation is an O/W type form and where the component (AI) is at least one selected from the group consisting of the component (AI-1), the component (AI-2) and the component (AI-3), the ratio by mass of the content of the component (BII) to the total content of the component (AI-1), the component (AI-2) and the component (AI-3) in the external preparation, [(BII)/[(AI-1)+(AI-2)+(AI-3)]] is, from the viewpoint of improving the adhesion suppressing effect, preferably 3.5 or less, more preferably 3 or less, even more preferably 2.5 or less, further more preferably 2 or less, and is, from the viewpoint of improving the feel in use in application to skin, preferably 0.01 or more, more preferably 0.03 or more, even more preferably 0.05 or more, further more preferably 0.1 or more.

In the case where the external preparation is an O/W type form and where the external preparation contains the component (CII-1), the content of the component (CII-1) in the external preparation is, from the viewpoint of improving the feel in use in application to skin, preferably 0.1% by mass or more, more preferably 1% by mass or more, even more preferably 3% by mass or more, further more preferably 5% by mass or more, further more preferably 8% by mass or more, further more preferably 10% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

In the case where the external preparation is an O/W type form and where the external preparation contains the component (CII-2), the content of the component (CII-2) in the external preparation is, from the viewpoint of improving the feel in use in application to skin, preferably 0.1% by mass or more, more preferably 0.5% by mass or more, even more preferably 1% by mass or more, and is, from the same viewpoint as above and from the viewpoint of improving the adhesion suppressing effect, preferably 15% by mass or less, more preferably 10% by mass or less, even more preferably 8% by mass or less, further more preferably 6% by mass or less.

In the fourth aspect of the invention where the external preparation is an O/W type form, the content and the mass ratio of each component in the external preparation are as described below.

In the O/W type external preparation, the content of the component (BIII) therein is, from the viewpoint of bettering the feel in use in application to skin, preferably 0.05% by mass or more, more preferably 0.1% by mass or more, even more preferably 0.5% by mass or more, further more preferably 1% by mass or more, and is, from the viewpoint of improving the adhesion suppressing effect and from the viewpoint of the feel in use such as stickiness, preferably 15% by mass or less, more preferably 10% by mass or less, even more preferably 8% by mass or less, further more preferably 6% by mass or less.

In the case where the external preparation is an O/W type form, the ratio by mass of the content of the component (BIII) to the component (AI) in the external preparation, [(BIII)/(AI)] is, from the viewpoint of improving the adhesion suppressing effect, 0.85 or less, preferably 0.80 or less, more preferably 0.75 or less, even more preferably 0.70 or less, and is, from the viewpoint of improving the feel in use in application to skin, preferably 0.01 or more, more preferably 0.03 or more, even more preferably 0.05 or more, further more preferably 0.10 or more.

In the case where the external preparation is an O/W type form and where the component (AI) is at least one selected from the group consisting of the component (AI-1), the component (AI-2) and the component (AI-3), the ratio by mass of the content of the component (BIII) to the total content of the component (AI-1), the component (AI-2) and the component (AI-3) in the external preparation, [(BIII)/[(AI-1)+(AI-2)+(AI-3)]] is, from the viewpoint of improving the adhesion suppressing effect, preferably 0.85 or less, preferably 0.80 or less, more preferably 0.75 or less, even more preferably 0.70 or less, and is, from the viewpoint of improving the feel in use in application to skin, preferably 0.01 or more, more preferably 0.03 or more, even more preferably 0.05 or more, further more preferably 0.10 or more.

In the case where the external preparation is an O/W type form and where the external preparation contains the component (CIII-1), the content of the component (CIII-1) in the external preparation is, from the viewpoint of improving the feel in use in application to skin, preferably 0.1% by mass or more, more preferably 1% by mass or more, even more preferably 3% by mass or more, further more preferably 5% by mass or more, further more preferably 8% by mass or more, further more preferably 10% by mass or more, and is, from the same viewpoint as above and from the viewpoint of improving the adhesion suppressing effect, preferably 25% by mass or less, more preferably 20% by mass or less, even more preferably 18% by mass or less, further more preferably 16% by mass or less.

In the case where the external preparation is an O/W type form and where the external preparation contains the component (CIII-2), the content of the component (CIII-2) in the external preparation is, from the viewpoint of improving the feel in use in application to skin, preferably 0.1% by mass or more, more preferably 1% by mass or more, even more preferably 3% by mass or more, further more preferably 5% by mass or more, further more preferably 8% by mass or more, further more preferably 10% by mass or more, and is, from the same viewpoint as above and from the viewpoint of improving the adhesion suppressing effect, preferably 25% by mass or less, more preferably 20% by mass or less, even more 16% by mass or less.

In the second to fourth aspects of the invention where the external preparation is an O/W type form and where the external preparation contains the component (D), the content of the component (D) in the external preparation is, from the viewpoint of improving the adhesion suppressing effect, preferably 0.01% by mass or more, more preferably 0.03% by mass or more, even more preferably 0.05% by mass or more, and is preferably 7% by mass or less, more preferably 5% by mass or less, even more preferably 3% by mass or less.

[Coating Method]

As a method for applying the external preparation to skin in the second to fourth aspects of the invention, any known method is employable in accordance with the use form and the intended object of the external preparation. Here, "applying to skin" includes not only direct application of the external preparation to the surface of skin by hand and the like but also adhesion of the external preparation to the surface of skin by spraying or the like. In general, the external preparation that is liquid, foam, paste, cream or solid can be applied to skin directly as it is or by spraying or the like.

(Coating Amount of Component (AI))

In the second to fourth aspects of the invention, the coating amount of the component (AI) on the surface of skin is, from the viewpoint of improving the adhesion suppressing effect, preferably 0.03 mg/cm$^2$ or more, more preferably 0.04 mg/cm$^2$ or more, even more preferably 0.05 mg/cm$^2$ or more, further more preferably 0.07 mg/cm$^2$ or more, and is, from the viewpoint of improving the feel in use in application to skin and from the viewpoint of economy, preferably 0.8 mg/cm$^2$ or less, more preferably 0.7 mg/cm$^2$ or less, even more preferably 0.6 mg/cm$^2$ or less. More specifically, the coating amount of the component (AI) on the surface of skin is, from the viewpoint of improving the adhesion suppressing effect and from the viewpoint of improving the feel in use in application to skin, and also from the viewpoint of economy, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.07 to 0.7 mg/cm$^2$, further more preferably 0.07 to 0.6 mg/cm$^2$.

In the second to fourth aspects of the invention where the component (AI) is at least one selected from the group consisting of the component (AI-1), the component (AI-2) and the component (AI-3), the total coating amount of the component (AI-1), the component (AI-2) and the component (AI-3) on the surface of skin is, from the viewpoint of improving the adhesion suppressing effect, preferably 0.03 mg/cm$^2$ or more, more preferably 0.04 mg/cm$^2$ or more, even more preferably 0.05 mg/cm$^2$ or more, further more preferably 0.07 mg/cm$^2$ or more, and is, from the viewpoint of improving the feel in use in application to skin and from the viewpoint of economy, preferably 0.8 mg/cm$^2$ or less, more preferably 0.7 mg/cm$^2$ or less, even more preferably 0.6 mg/cm$^2$ or less. More specifically, the total coating amount of the component (AI-1), the component (AI-2) and the component (AI-3) on the surface of skin is, from the viewpoint of improving the adhesion suppressing effect and from the viewpoint of improving the feel in use in application to skin, and also from the viewpoint of economy, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.07 to 0.7 mg/cm$^2$, further more preferably 0.07 to 0.6 mg/cm$^2$.

In the second to fourth aspects of the invention where the external preparation is a W/O type form, the coating amount of the component (AI) on the surface of skin is, from the viewpoint of improving the adhesion suppressing effect, preferably 0.03 mg/cm$^2$ or more, more preferably 0.04 mg/cm$^2$ or more, even more preferably 0.05 mg/cm$^2$ or more, further more preferably 0.07 mg/cm$^2$ or more, further more preferably 0.10 mg/cm$^2$ or more, further more preferably 0.20 mg/cm$^2$ or more, and is, from the viewpoint of improving the feel in use in application to skin and from the viewpoint of economy, preferably 0.8 mg/cm$^2$ or less, more preferably 0.7 mg/cm$^2$ or less, even more preferably 0.6 mg/cm$^2$ or less. More specifically, the coating amount of the component (AI) on the surface of skin is, from the viewpoint of improving the adhesion suppressing effect and from the viewpoint of improving the feel in use in application to skin, and also from the viewpoint of economy, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.10 to 0.8 mg/cm$^2$, further more preferably 0.20 to 0.7 mg/cm$^2$, further more preferably 0.20 to 0.6 mg/cm$^2$.

In the second to fourth aspects of the invention where the external preparation is a W/O type form and where the component (AI) is at least one selected from the group consisting of the component (AI-1), the component (AI-2) and the component (AI-3), the total coating amount of the component (AI-1), the component (AI-2) and the component (AI-3) on the surface of skin is, from the viewpoint of improving the adhesion suppressing effect, preferably 0.03 mg/cm$^2$ or more, more preferably 0.04 mg/cm$^2$ or more, even more preferably 0.05 mg/cm$^2$ or more, further more preferably 0.07 mg/cm$^2$ or more, further more preferably 0.10 mg/cm$^2$ or more, further more preferably 0.20 mg/cm$^2$ or more, and is, from the viewpoint of improving the feel in use in application to skin and from the viewpoint of economy, preferably 0.8 mg/cm$^2$ or less, more preferably 0.7 mg/cm$^2$ or less, even more preferably 0.6 mg/cm$^2$ or less. More specifically, the total coating amount of the component (AI-1), the component (AI-2) and the component (AI-3) on the surface of skin is, from the viewpoint of improving the adhesion suppressing effect and from the viewpoint of improving the feel in use in application to skin, and also from the viewpoint of economy, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.10 to 0.8 mg/cm$^2$, further more preferably 0.20 to 0.7 mg/cm$^2$, further more preferably 0.20 to 0.6 mg/cm$^2$.

In the second to fourth aspects of the invention where the external preparation is an O/W type form, the coating amount of the component (AI) on the surface of skin is, from the viewpoint of improving the adhesion suppressing effect, preferably 0.03 mg/cm$^2$ or more, more preferably 0.04 mg/cm$^2$ or more, even more preferably 0.05 mg/cm$^2$ or more, further more preferably 0.07 mg/cm$^2$ or more, and is, from the viewpoint of improving the feel in use in application to skin and from the viewpoint of economy, preferably 0.8 mg/cm$^2$ or less, more preferably 0.7 mg/cm$^2$ or less, even more preferably 0.6 mg/cm$^2$ or less, further more preferably 0.3 mg/cm$^2$ or less. More specifically, the coating amount of the component (AI) on the surface of skin is, from the viewpoint of improving the adhesion suppressing effect and from the viewpoint of improving the feel in use in application to skin, and also from the viewpoint of economy, preferably 0.03 to 0.8 mg/cm$^2$, more preferably 0.04 to 0.8 mg/cm$^2$, even more preferably 0.05 to 0.8 mg/cm$^2$, further more preferably 0.07 to 0.8 mg/cm$^2$, further more preferably 0.07 to 0.7 mg/cm$^2$, further more preferably 0.07 to 0.6 mg/cm$^2$, further more preferably 0.07 to 0.3 mg/cm$^2$.

In the second to fourth aspects of the invention where the external preparation is an O/W type form and where the component (AI) is one or more selected from the component (AI-1), the component (AI-2) and the component (AI-3), the total coating amount of the component (AI-1), the component (AI-2) and the component (AI-3) on the surface of skin is, from the viewpoint of improving the adhesion suppressing effect, preferably 0.03 mg/cm$^2$ or more, more preferably 0.04 mg/cm$^2$ or more, even more preferably 0.05 mg/cm$^2$ or more, further more preferably 0.07 mg/cm$^2$ or more, and is, from the viewpoint of improving the feel in use in application to skin and from the viewpoint of economy, preferably 0.8 mg/cm$^2$ or less, more preferably 0.7 mg/cm$^2$ or less, even more preferably 0.6 mg/cm$^2$ or less, even more preferably 0.3 mg/cm$^2$ or less. More specifically, the total coating amount of the component (AI-1), the component (AI-2) and the component (AI-3) on the surface of skin is, from the viewpoint of improving the adhesion suppressing effect and from the viewpoint of improving the feel in use in application to skin, and also from the viewpoint of economy, preferably 0.03 to 0.8 mg/cm$^2$, more preferably 0.04 to 0.8 mg/cm$^2$, even more preferably 0.05 to 0.8 mg/cm$^3$, further more preferably 0.07 to 0.8 mg/cm$^2$, further more preferably 0.07 to 0.7 mg/cm$^2$, further more preferably 0.07 to 0.6 mg/cm$^2$, further more preferably 0.07 to 0.3 mg/cm$^2$.

Regarding the above-mentioned embodiments, the present invention further discloses the following embodiments.

<1> A method for suppressing adhesion of air harmful substances, including applying a metal oxide (A) having an average primary particle diameter $d_A$ of 300 nm or less to skin in an amount of 0.07 mg/cm$^2$ or more to suppress adhesion of air harmful substances to the skin.

<2> The method for suppressing adhesion of air pollutants harmful substances according to the above <1>, wherein the metal oxide (A) is at least one selected from the group consisting of the group consisting of titanium oxide and zinc oxide.

<3> The method for suppressing adhesion of air harmful substances according to the above <1> or <2>, wherein the metal oxide (A) is one hydrophobized or hydrophilized on the surface thereof.

<4> The method for suppressing adhesion of air harmful substances according to any of the above <1> to <3>, wherein the metal oxide (A) is one hydrophobized on the surface thereof.

<5> The method for suppressing adhesion of air harmful substances according to the above <4>, wherein the hydrophobizing treatment is at least one selected from the group consisting of a silicone treatment, an alkylalkoxysilane treatment and a fatty acid treatment.

<6> The method for suppressing adhesion of air harmful substances according to any of the above <1> to <5>, wherein the average primary particle diameter $d_A$ of the metal oxide (A) is 80 nm or less.

<7> The method for suppressing adhesion of air harmful substances according to any of the above <1> to <6>, wherein the average primary particle diameter $d_A$ of the metal oxide (A) is 50 nm or less.

<8> The method for suppressing adhesion of air harmful substances according to any of the above <1> to <7>, wherein the average primary particle diameter $d_A$ of the metal oxide (A) is 5 nm or more.

<9> The method for suppressing adhesion of air harmful substances according to any of the above <1> to <8>, wherein the metal oxide (A) is applied to skin in an amount of 0.15 mg/cm$^2$ or more.

<10> The method for suppressing adhesion of air harmful substances according to any of the above <1> to <9>, wherein the metal oxide (A) is applied to skin in an amount of 0.8 mg/cm$^2$ or less.

<11> A method for suppressing adhesion of air harmful substances, including applying, as a metal oxide (A), at least one selected from the group consisting of hydrophobized titanium oxide and zinc oxide having an average primary particle diameter $d_A$ of 5 nm or more and 300 nm or less to skin in an amount of 0.07 mg/cm$^2$ or more and 0.8 mg/cm$^2$ or less to suppress adhesion of air harmful substances to the skin.

<12> A method for suppressing adhesion of air harmful substances, including applying, as a metal oxide (A), at least one selected from the group consisting of hydrophobized titanium oxide and zinc oxide having an average primary particle diameter $d_A$ of 5 nm or more and 80 nm or less to skin in an amount of 0.07 mg/cm$^2$ or more and 0.8 mg/cm$^2$ or less to suppress adhesion of air air harmful substances to the skin.

<13> A method for suppressing adhesion of air harmful substances, including applying, as a metal oxide (A), at least one selected from the group consisting of hydrophobized titanium oxide and zinc oxide having an average primary particle diameter $d_A$ of 5 nm or more and 50 nm or less to skin in an amount of 0.15 mg/cm$^2$ or more and 0.8 mg/cm$^2$ or less to suppress adhesion of air harmful substances to the skin.

<14> The method for suppressing adhesion of air harmful substances according to any of the above <11> to <13>, wherein the hydrophobizing treatment is at least one selected from the group consisting of a silicone treatment, an alkylalkoxysilane treatment and a fatty acid treatment.

<15> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI), and the ratio by mass of the content of the component (BI) to the total content of the component (AI-1), the component (AI-2) and the component (AI-3) in the external preparation, [(BI)/[(AI-1)+ (AI-2)+ (AI-3)]] is 9 or less, and 0.01 or more:

Component (AI-1): at least one selected from the group consisting of fatty acid-treated titanium oxide and zinc oxide having an average primary particle diameter $d_{AI}$ of 5 nm or more and 80 nm or less.

Component (AI-2): at least one selected from the group consisting of alkylalkoxysilane-treated titanium oxide and zinc oxide having an average primary particle diameter $d_{AI}$ of 5 nm or more and 80 nm or less.

Component (AI-3): at least one selected from the group consisting of silicone-treated titanium oxide and zinc oxide having an average primary particle diameter $d_{AI}$ of 5 nm or more and 80 nm or less.

Component (BI): an ester oil.

<16> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI), and the ratio by mass of the content of the component (BI) to the total content of the component (AI-1), the component (AI-2) and the component (AI-3) in the external preparation, [(BI)/[(AI-1)+(AI-2)+(AI-3)]] is 9 or less, and 0.01 or more:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BI): an ester oil.

<17> The method for suppressing adhesion of air harmful substances according to the above <15> or <16>, wherein the mass ratio [(BI)/[(AI-1)+(AI-2)+(AI-3)]] is 6 or less and 0.05 or more.

<18> The method for suppressing adhesion of air harmful substances according to the above <15> or <16>, wherein the mass ratio [(BI)/[(AI-1)+(AI-2)+(AI-3)]] is 4 or less and 0.1 or more.

<19> The method for suppressing adhesion of air harmful substances according to any of the above <15> to <18>, wherein the total coating amount on skin of the component (AI-1), the component (AI-2) and the component (AI-3) is 0.03 mg/cm² or more and 0.8 mg/cm² or less.

<20> The method for suppressing adhesion of air harmful substances according to any of the above <15> to <18>, wherein the total coating amount on skin of the component (AI-1), the component (AI-2) and the component (AI-3) is 0.05 mg/cm² or more and 0.8 mg/cm² or less.

<21> The method for suppressing adhesion of air harmful substances according to any of the above <15> to <18>, wherein the total coating amount on skin of the component (AI-1), the component (AI-2) and the component (AI-3) is 0.07 mg/cm² or more and 0.7 mg/cm² or less.

<22> The method for suppressing adhesion of air harmful substances according to any of the above <15> to <21>, wherein the total content of the component (AI-1), the component (AI-2) and the component (AI-3) in the external preparation is 1% by mass or more and 40% by mass or less.

<23> The method for suppressing adhesion of air harmful substances according to any of the above <15> to <21>, wherein the total content of the component (AI-1), the component (AI-2) and the component (AI-3) in the external preparation is 2% by mass or more and 35% by mass or less.

<24> The method for suppressing adhesion of air harmful substances according to any of the above <15> to <21>, wherein the total content of the component (AI-1), the component (AI-2) and the component (AI-3) in the external preparation is 3% by mass or more and 30% by mass or less.

<25> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI), and the ratio by mass of the content of the component (BI) to the total content of the component (AI-1), the component (AI-2) and the component (AI-3) in the external preparation, [(BI)/[(AI-1)+ (AI-2)+ (AI-3)]] is 6 or less and 0.05 or more, and the total coating amount on the skin of the component (AI-1), the component (AI-2) and the component (AI-3) is 0.03 mg/cm² or more and 0.8 mg/cm² or less:

Component (AI-1): at least one selected from the group consisting of fatty acid-treated titanium oxide and zinc oxide having an average primary particle diameter day of 5 nm or more and 80 nm or less.

Component (AI-2): at least one selected from the group consisting of alkylalkoxysilane-treated titanium oxide and zinc oxide having an average primary particle diameter $d_{AI}$ of 5 nm or more and 80 nm or less.

Component (AI-3): at least one selected from the group consisting of silicone-treated titanium oxide and zinc oxide having an average primary particle diameter $d_{AI}$ of 5 nm or more and 80 nm or less.

Component (BI): an ester oil.

<26> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI), and the ratio by mass of the content of the component (BI) to the total content of the component (AI-1), the component (AI-2) and the component (AI-3) in the external preparation, [(BI)/[(AI-1)+(AI-2)+(AI-3)]] is 4 or less and 0.05 or more, and the total coating amount on the skin of the component (AI-1), the component (AI-2) and the component (AI-3) is 0.03 mg/cm² or more and 0.8 mg/cm² or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BI): an ester oil.

<27> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI), and the ratio by mass of the content of the component (B) to the total content of the component (AI-1), the component (AI-2) and the component (AI-3) in the external preparation, [(BI)/[(AI)+(AI-2)+(AI-3)]] is 6 or less and 0.05 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 80 nm or less.

Component (AI-2): at least one selected from the group consisting of alkylalkoxysilane-treated titanium oxide and zinc oxide having an average primary particle diameter $d_{AI}$ of 5 nm or more and 80 nm or less.

Component (AI-3): at least one selected from the group consisting of silicone-treated titanium oxide and zinc oxide having an average primary particle diameter $d_{AI}$ of 5 nm or more and 80 nm or less.

Component (BI): an ester oil.

<28> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI), and the ratio by mass of the content of the component (BI) to the total content of the component (AI-1), the component (AI-2) and the component (AI-3) in the external preparation, [(BI)/[(AI-1)+ (AI-2)+ (AI-3)]] is 4 or less and 0.05 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BI): an ester oil.

<29> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI) and component (CI-1), and the ratio by mass of the content of the component (BI) to the total content of the component (AI-1), the component (AI-2) and the component (AI-3) in the external preparation, [(BI)/[(AI-1)+(AI-2)+(AI-3)]] is 4 or less and 0.1 or more, the ratio by mass of the content of the component (CI-1) to the total content of the component (AI-1), the component (AI-2) and the component (AI-3) in the external preparation, [(CI-1)/[(AI-1)+(AI-2)+(AI-3)]] is 2 or less and 0.1 or more, the ratio by mass of the total content of the component (BI) and the component (CI-1) to the total content of the component (AI-1), the component (AI-2) and the component (AI-3) in the external preparation, [[(BI)+(CI-1)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BI): an ester oil.

Component (CI-1): a nonvolatile hydrocarbon oil.

<30> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BI) and component (CI-2), and the ratio by mass of the content of the component (BI) to the total content of the component (AI-1), the component (AI-2) and the component (AI-3) in the external preparation, [(BI)/[(AI-1)+(AI-2)+(AI-3)]] is 4 or less and 0.1 or more, the ratio by mass of the content of the component (CI-2) to the total content of the component (AI-1), the component (AI-2) and the component (AI-3) in the external preparation, [(CI-2)/[(AI-1)+(AI-2)+(AI-3)]] is 0.70 or less and 0.03 or more, the ratio by mass of the total content of the component (BI) and the component (CI-2) to the total content of the component (AI-1), the component (AI-2) and the component (AI-3) in the external preparation, [[(BI)+(CI-2)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BI): an ester oil.

Component (CI-2): a nonvolatile silicone oil.

<31> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BI), component (CI-1) and component (CI-2), and the ratio by mass of the content of the component (BI) to the total content of the component (AI-1), the component (AI-2) and the component (AI-3) in the external preparation, [(BI)/[(AI-1)+(AI-2)+(AI-3)]] is 4 or less and 0.1 or more, the ratio by mass of the content of the component (CI-2) to the total content of the component (AI-1), the component (AI-2) and the component (AI-3) in the external preparation, [(CI-2)/[(AI-1)+(AI-2)+(AI-3)]] is 0.70 or less and 0.03 or more, the ratio by mass of the total content of the component (CI-1) and the component (CI-2) to the total content of the component (AI-1), the component (AI-2) and the component (AI-3) in the external preparation, [[(CI-1)+(CI-2)]/[(AI-1)+(AI-2)+(AI-3)]] is 2 or less and 0.1 or more, the ratio by mass of the total content of the component (BI), the component (CI-1) and the component (CI-2) to the total content of the component (AI-1), the component (AI-2) and the component (AI-3) in the external preparation, [[(BI)+(CI-1)+(CI-2)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BI): an ester oil.

Component (CI-1): a nonvolatile hydrocarbon oil.

Component (CI-2): a nonvolatile silicone oil.

<32> The method for suppressing adhesion of air harmful substances according to any of the above <25> to <31>, wherein the external preparation is a water-in-oil type and the total content of the component (AI-1), the component (AI-2) and the component (AI-3) in the external preparation is 10% by mass or more and 40% by mass or less.

<33> The method for suppressing adhesion of air harmful substances according to any of the above <25> to <31>, wherein the external preparation is an oil-in-water type and the total content of the component (AI-1), the component (AI-2) and the component (AI-3) in the external preparation is 1% by mass or more and 15% by mass or less.

<34> The method for suppressing adhesion of air harmful substances according to any of the above <25> to <33>, wherein the content of the component (BI) in the external preparation is 1% by mass or more and 18% by mass or less.

<35> The method for suppressing adhesion of air harmful substances according to any of the above <25> to <34>, wherein the total coating amount on skin of the component (AI-1), the component (AI-2) and the component (AI-3) is 0.05 mg/cm$^2$ or more and 0.8 mg/cm$^2$ or less.

<36> The method for suppressing adhesion of air harmful substances according to any of the above <25> to <34>, wherein the total coating amount on skin of the component (AI-1), the component (AI-2) and the component (AI-3) is 0.07 g/cm$^2$ or more and 0.7 mg/cm$^2$ or less.

<37> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BII), and the ratio by mass of the content of the component (B) to the total content of the component (AI-1), the component (AI-2) and the component (AI-3) in the external preparation, [(B)/[(AI-1)+(AI-2)+(AI-3)]] is 3.5 or less and 0.01 or more:

Component (AI-1): at least one selected from the group consisting of fatty acid-treated titanium oxide and zinc oxide having an average primary particle diameter $d_{AI}$ of 5 nm or more and 80 nm or less.

Component (AI-2): at least one selected from the group consisting of alkylalkoxysilane-treated titanium oxide and zinc oxide having an average primary particle diameter $d_{AI}$ of 5 nm or more and 80 nm or less.

Component (AI-3): at least one selected from the group consisting of silicone-treated titanium oxide and zinc oxide having an average primary particle diameter $d_{AI}$ of 5 nm or more and 80 nm or less.

Component (BII): a nonvolatile hydrocarbon oil.

<38> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BII), and the ratio by mass of the content of the component (BII) to the total content of the component (AI-1), the component (AI-2) and the component (AI-3) in the external preparation, [(BII)/[(AI-1)+(AI-2)+(AI-3)]] is 3.5 or less and 0.01 or more:
Component (AI-1): at least one selected from the group consisting of fatty acid-treated titanium oxide and zinc oxide having an average primary particle diameter $d_{AI}$ of 5 nm or more and 50 nm or less.
Component (AI-2): at least one selected from the group consisting of alkylalkoxysilane-treated titanium oxide and zinc oxide having an average primary particle diameter $d_{AI}$ of 5 nm or more and 50 nm or less.
Component (AI-3): at least one selected from the group consisting of silicone-treated titanium oxide and zinc oxide having an average primary particle diameter $d_{AI}$ of 5 nm or more and 50 nm or less.
Component (BII): a nonvolatile hydrocarbon oil.

<39> The method for suppressing adhesion of air harmful substances according to the above <37> or <38>, wherein the ratio by mass [(BII)/[(AI-1)+(AI-2)+(AI-3)]] is 2.5 or less and 0.05 or more.

<40> The method for suppressing adhesion of air harmful substances according to the above <37> or <38>, wherein the ratio by mass [(BII)/[(AI-1)+ (AI-2)+ (AI-3)]] is 2 or less and 0.1 or more.

<41> The method for suppressing adhesion of air harmful substances according to any of the above <37> to <40>, wherein the total coating amount on skin of the component (AI-1), the component (AI-2) and the component (AI-3) is 0.03 mg/cm² or more and 0.8 mg/cm² or less.

<42> The method for suppressing adhesion of air harmful substances according to any of the above <37> to <40>, wherein the total coating amount on skin of the component (AI-1), the component (AI-2) and the component (AI-3) is 0.05 mg/cm² or more and 0.8 mg/cm² or less.

<43> The method for suppressing adhesion of air harmful substances according to any of the above <37> to <40>, wherein the total coating amount on skin of the component (AI-1), the component (AI-2) and the component (AI-3) is 0.07 mg/cm² or more and 0.7 mg/cm² or less.

<44> The method for suppressing adhesion of air harmful substances according to any of the above <37> to <43>, wherein the total content of the component (AI-1), the component (AI-2) and the component (AI-3) in the external preparation is 1% by mass or more and 40% by mass or less.

<45> The method for suppressing adhesion of air harmful substances according to any of the above <37> to <43>, wherein the total content of the component (AI-1), the component (AI-2) and the component (AI-3) in the external preparation is 2% by mass or more and 35% by mass or less.

<46> The method for suppressing adhesion of air harmful substances according to any of the above <37> to <43>, wherein the total content of the component (AI-1), the component (AI-2) and the component (AI-3) in the external preparation is 3% by mass or more and 30% by mass or less.

<47> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BII), and the ratio by mass of the content of the component (BII) to the total content of the component (AI-1), the component (AI-2) and the component (AI-3) in the external preparation, [(BII)/[(AI-1)+(AI-2)+(AI-3)]] is 2.5 or less and 0.05 or more, and the total coating amount on skin of the component (AI-1), the component (AI-2) and the component (AI-3) is 0.03 mg/cm² or more and 0.8 mg/cm² or less:
Component (AI-1): at least one selected from the group consisting of fatty acid-treated titanium oxide and zinc oxide having an average primary particle diameter $d_{AI}$ of 5 nm or more and 80 nm or less.
Component (AI-2): at least one selected from the group consisting of alkylalkoxysilane-treated titanium oxide and zinc oxide having an average primary particle diameter $d_{AI}$ of 5 nm or more and 80 nm or less.
Component (AI-3): at least one selected from the group consisting of silicone-treated titanium oxide and zinc oxide having an average primary particle diameter $d_{AI}$ of 5 nm or more and 80 nm or less.
Component (BII): a nonvolatile hydrocarbon oil.

<48> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BII), and the ratio by mass of the content of the component (BII) to the total content of the component (AI-1), the component (AI-2) and the component (AI-3) in the external preparation, [(BII)/[(AI-1)+(AI-2)+(AI-3)]] is 2 or less and 0.1 or more, and the total coating amount on skin of the component (AI-1), the component (AI-2) and the component (AI-3) is 0.03 mg/cm² or more and 0.8 mg/cm² or less:
Component (AI-1): at least one selected from the group consisting of fatty acid-treated titanium oxide and zinc oxide having an average primary particle diameter $d_{AI}$ of 5 nm or more and 50 nm or less.
Component (AI-2): at least one selected from the group consisting of alkylalkoxysilane-treated titanium oxide and zinc oxide having an average primary particle diameter $d_{AI}$ of 5 nm or more and 50 nm or less.
Component (AI-3): at least one selected from the group consisting of silicone-treated titanium oxide and zinc oxide having an average primary particle diameter $d_{AI}$ of 5 nm or more and 50 nm or less.
Component (BII): a nonvolatile hydrocarbon oil.

<49> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BII), and the ratio by mass of the content of the component (BII) to the total content of the component (AI-1), the component (AI-2) and the component (AI-3) in the external preparation, [(BII)/[(AI-1)+(AI-2)+(AI-3)]] is 2.5 or less and 0.05 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 80 nm or less.

Component (AI-2): at least one selected from the group consisting of alkylalkoxysilane-treated titanium oxide and zinc oxide having an average primary particle diameter $d_{AI}$ of 5 nm or more and 80 nm or less.

Component (AI-3): at least one selected from the group consisting of silicone-treated titanium oxide and zinc oxide having an average primary particle diameter $d_{AI}$ of 5 nm or more and 80 nm or less.

Component (BII): a nonvolatile hydrocarbon oil.

<50> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BII), and the ratio by mass of the content of the component (BII) to the total content of the component (AI-1), the component (AI-2) and the component (AI-3) in the external preparation, [(BII)/[(AI-1)+(AI-2)+(AI-3)]] is 2 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BII): a nonvolatile hydrocarbon oil.

<51> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BII) and component (CII-1), and the ratio by mass of the content of the component (B) to the total content of the component (AI-1), the component (AI-2) and the component (AI-3) in the external preparation, [(BII)/[(AI-1)+(AI-2)+(AI-3)]] is 2 or less and 0.1 or more, the ratio by mass of the total content of the component (BII) and the component (CII-1) to the total content of the component (AI-1), the component (AI-2) and the component (AI-3) in the external preparation, [[(BII)+(CII-1)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BII): a nonvolatile hydrocarbon oil.

Component (CII-1): an ester oil.

<52> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BII) and component (CII-2), and the ratio by mass of the content of the component (BII) to the total content of the component (AI-1), the component (AI-2) and the component (AI-3) in the external preparation, [(BII)/[(AI-1)+(AI-2)+(AI-3)]] is 2 or less and 0.1 or more, the ratio by mass of the content of the component (CII-2) to the total content of the component (AI-1), the component (AI-2) and the component (AI-3) in the external preparation, [(CII-2)/[(AI-1)+(AI-2)+(AI-3)]] is 0.70 or less and 0.03 or more, the ratio by mass of the total content of the component (BII) and the component (CII-2) to the total content of the component (AI-1), the component (AI-2) and the component (AI-3) in the external preparation, [[(BII)+(CII-2)]/[(AI-1)+(AI-2)+(AI-3)]] is 2 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BII): a nonvolatile hydrocarbon oil.

Component (CII-2): a nonvolatile silicone oil.

<53> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BII), component (CII-1) and component (CII-2), and the ratio by mass of the content of the component (BIII) to the total content of the component (AI-1), the component (AI-2) and the component (AI-3) in the external preparation, [(BII)/[(AI-1)+(AI-2)+(AI-3)]] is 2 or less and 0.1 or more, the ratio by mass of the content of the component (CII-2) to the total content of the component (AI-1), the component (AI-2) and the component (AI-3) in the external preparation, [(CII-2)/[(AI-1)+(AI-2)+(AI-3)]] is 0.70 or less and 0.03 or more, the ratio by mass of the total content of the component (BIII) and the component (CIII-2) to the total content of the component (AI-1), the component (AI-2) and the component (AI-3) in the external preparation, [[(BII)+(CII-2)]/[(AI-1)+(AI-2)+(AI-3)]] is 2 or less and 0.1 or more, the ratio by mass of the total content of the component (BII), the component (CII-1) and the component (CII-2) to the total content of the component (AI-1), the component (AI-2) and the component (AI-3) in the external preparation, [[(BII)+(CII-1)+(CII-2)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:
- Component (AI-1): at least one selected from the group consisting of fatty acid-treated titanium oxide and zinc oxide having an average primary particle diameter $d_{AI}$ of 5 nm or more and 50 nm or less.
- Component (AI-2): at least one selected from the group consisting of alkylalkoxysilane-treated titanium oxide and zinc oxide having an average primary particle diameter $d_{AI}$ of 5 nm or more and 50 nm or less.
- Component (AI-3): at least one selected from the group consisting of silicone-treated titanium oxide and zinc oxide having an average primary particle diameter $d_{AI}$ of 5 nm or more and 50 nm or less.
- Component (BII): a nonvolatile hydrocarbon oil.
- Component (CII-1): an ester oil.
- Component (CII-2): a nonvolatile silicone oil.

<54> The method for suppressing adhesion of air harmful substances according to any of <47> to <53>, wherein the external preparation is a water-in-oil type and the total content of the component (AI-1), the component (AI-2) and the component (AI-3) in the external preparation is 10% by mass or more and 40% by mass or less.

<55> The method for suppressing adhesion of air harmful substances according to any of <47> to <53>, wherein the external preparation is an oil-in-water type and the total content of the component (AI-1), the component (AI-2) and the component (AI-3) in the external preparation is 1% by mass or more and 15% by mass or less.

<56> The method for suppressing adhesion of air harmful substances according to any of <47> to <55>, wherein the content of the component (BII) in the external preparation is 1% by mass or more and 18% by mass or less.

<57> The method for suppressing adhesion of air harmful substances according to any of <47> to <56>, wherein the total coating amount on skin of the component (AI-1), the component (AI-2) and the component (AI-3) is 0.05 mg/cm$^2$ or more and 0.8 mg/cm$^2$ or less.

<58> The method for suppressing adhesion of air harmful substances according to any of <47> to <56>, wherein the total coating amount on skin of the component (AI-1), the component (AI-2) and the component (AI-3) is 0.07 g/cm$^2$ or more and 0.7 mg/cm$^2$ or less.

<59> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BIII), and the ratio by mass of the content of the component (BIII) to the total content of the component (AI-1), the component (AI-2) and the component (AI-3) in the external preparation, [(BIII)/[(AI-1)+(AI-2)+(AI-3)]] is 0.85 or less and 0.01 or more:
- Component (AI-1): at least one selected from the group consisting of fatty acid-treated titanium oxide and zinc oxide having an average primary particle diameter $d_{AI}$ of 5 nm or more and 80 nm or less.
- Component (AI-2): at least one selected from the group consisting of alkylalkoxysilane-treated titanium oxide and zinc oxide having an average primary particle diameter $d_{AI}$ of 5 nm or more and 80 nm or less.
- Component (AI-3): at least one selected from the group consisting of silicone-treated titanium oxide and zinc oxide having an average primary particle diameter $d_{AI}$ of 5 nm or more and 80 nm or less.
- Component (BIII): a nonvolatile silicone oil.

<60> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BIII), and the ratio by mass of the content of the component (BIII) to the total content of the component (AI-1), the component (AI-2) and the component (AI-3) in the external preparation, [(BIII)/[(AI-1)+(AI-2)+(AI-3)]] is 0.85 or less and 0.01 or more:
- Component (AI-1): at least one selected from the group consisting of fatty acid-treated titanium oxide and zinc oxide having an average primary particle diameter $d_{AI}$ of 5 nm or more and 50 nm or less.
- Component (AI-2): at least one selected from the group consisting of alkylalkoxysilane-treated titanium oxide and zinc oxide having an average primary particle diameter $d_{AI}$ of 5 nm or more and 50 nm or less.
- Component (AI-3): at least one selected from the group consisting of silicone-treated titanium oxide and zinc oxide having an average primary particle diameter $d_{AI}$ of 5 nm or more and 50 nm or less.
- Component (BIII): a nonvolatile silicone oil.

<61> The method for suppressing adhesion of air harmful substances according to the above <59> or <60>, wherein the ratio by mass [(BIII)/[(AI-1)+(AI-2)+(AI-3)]] is 0.75 or less and 0.02 or more.

<62> The method for suppressing adhesion of air harmful substances according to the above <59> or <60>, wherein the ratio by mass [(BIII)/[(AI-1)+(AI-2)+(AI-3)]] is 0.70 or less and 0.03 or more.

<63> The method for suppressing adhesion of air harmful substances according to any of the above <59> to <62>, wherein the total coating amount on skin of the component (AI-1), the component (AI-2) and the component (AI-3) is 0.03 mg/cm$^2$ or more and 0.8 mg/cm$^2$ or less.

<64> The method for suppressing adhesion of air harmful substances according to any of the above <59> to <62>, wherein the total coating amount on skin of the component (AI-1), the component (AI-2) and the component (AI-3) is 0.05 mg/cm$^2$ or more and 0.8 mg/cm$^2$ or less.

<65> The method for suppressing adhesion of air harmful substances according to any of the above <59> to <62>, wherein the total coating amount on skin of the component (AI-1), the component (AI-2) and the component (AI-3) is 0.07 mg/cm$^2$ or more and 0.7 mg/cm$^2$ or less.

<66> The method for suppressing adhesion of air harmful substances according to any of the above <59> to <65>, wherein the total content of the component (AI-1), the component (AI-2) and the component (AI-3) in the external preparation is 1% by mass or more and 40% by mass or less.

<67> The method for suppressing adhesion of air harmful substances according to any of the above <59> to <65>, wherein the total content of the component (AI-1), the component (AI-2) and the component (AI-3) in the external preparation is 2% by mass or more and 35% by mass or less.

<68> The method for suppressing adhesion of air harmful substances according to any of the above <59> to <65>, wherein the total content of the component (AI-1), the component (AI-2) and the component (AI-3) in the external preparation is 3% by mass or more and 30% by mass or less.

<69> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BIII), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.75 or less and 0.02 or more, and the total coating amount on skin of the component (AI-1), the component (AI-2) and the component (AI-3) is 0.03 mg/cm$^2$ or more and 0.8 mg/cm$^2$ or less:
Component (AI-1): at least one selected from the group consisting of fatty acid-treated titanium oxide and zinc oxide having an average primary particle diameter $d_{AI}$ of 5 nm or more and 80 nm or less.
Component (AI-2): at least one selected from the group consisting of alkylalkoxysilane-treated titanium oxide and zinc oxide having an average primary particle diameter $d_{AI}$ of 5 nm or more and 80 nm or less.
Component (AI-3): at least one selected from the group consisting of silicone-treated titanium oxide and zinc oxide having an average primary particle diameter $d_{AI}$ of 5 nm or more and 80 nm or less.
Component (BIII): a nonvolatile silicone oil.

<70> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BIII), the ratio by mass of the content of the component (BIII) to the total content of the component (AI-1), the component (AI-2) and the component (AI-3) in the external preparation, [(BIII)/[(AI-1)+ (AI-2)+ (AI-3)]] is 0.70 or less and 0.03 or more, and the total coating amount on skin of the component (AI-1), the component (AI-2) and the component (AI-3) is 0.03 mg/cm$^2$ or more and 0.8 mg/cm$^2$ or less:
Component (AI-1): at least one selected from the group consisting of fatty acid-treated titanium oxide and zinc oxide having an average primary particle diameter $d_{AI}$ of 5 nm or more and 50 nm or less.
Component (AI-2): at least one selected from the group consisting of alkylalkoxysilane-treated titanium oxide and zinc oxide having an average primary particle diameter $d_{AI}$ of 5 nm or more and 50 nm or less.
Component (AI-3): at least one selected from the group consisting of silicone-treated titanium oxide and zinc oxide having an average primary particle diameter $d_{AI}$ of 5 nm or more and 50 nm or less.
Component (BIII): a nonvolatile silicone oil.

<71> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI-3), and the following component (BIII), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.75 or less and 0.02 or more, and the total content of the component (AI-1), the component (AI-2) and the component (AI-3) in the external preparation is 1% by mass or more and 40% by mass or less:
Component (AI-1): at least one selected from the group consisting of fatty acid-treated titanium oxide and zinc oxide having an average primary particle diameter $d_{AI}$ of 5 nm or more and 80 nm or less.
Component (AI-2): at least one selected from the group consisting of alkylalkoxysilane-treated titanium oxide and zinc oxide having an average primary particle diameter $d_{AI}$ of 5 nm or more and 80 nm or less.
Component (AI-3): at least one selected from the group consisting of silicone-treated titanium oxide and zinc oxide having an average primary particle diameter $d_{AI}$ of 5 nm or more and 80 nm or less.
Component (BIII): a nonvolatile silicone oil.

<72> A method for suppressing adhesion of air harmful substances, including applying an external preparation to skin to suppress adhesion of air harmful substances to the skin, wherein:
the external preparation contains at least one selected from the group consisting of the following component (AI-1), component (AI-2) and component (AI- 3), and the following component (BIII), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.70 or less and 0.03 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BIII): a nonvolatile silicone oil.

<73> A method for suppressing adhesion of air harmful substances, including applying an external preparation to skin to suppress adhesion of air harmful substances to the skin, wherein:

the external preparation contains one or more selected from the following component (AI-1), component (AI-2) and component (AI-3), and the following component (BIII) and component (CIII-1), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.70 or less and 0.03 or more, the ratio by mass of the total content of the component (B) and the component (C1) to the total content of the component (AI-1), the component (AI-2) and the component (AI-3) in the external preparation, [[(BIII)+(CIII-1)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BIII): a nonvolatile silicone oil.

Component (CIII-1): an ester oil.

<74> A method for suppressing adhesion of air harmful substances, including applying an external preparation to skin to suppress adhesion of air harmful substances to the skin, wherein:

the external preparation contains at least one selected from the group consisting of the following component (AI-1), component (AI-2) and component (AI-3), and the following component (BIII) and component (CIII-2), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.70 or less and 0.03 or more, the ratio by mass of the total content of the component (BIII) and the component (CIII-2) to the total content of the component (AI-1), the component (AI-2) and the component (AI-3) in the external preparation, [[(BIII)+(CIII-2)]/[(AI-1)+(AI-2)+(AI-3)]] is 2 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BIII): a nonvolatile silicone oil.

Component (CIII-2): a nonvolatile hydrocarbon oil.

<75> A method for suppressing adhesion of air harmful substances, including applying an external preparation to skin to suppress adhesion of air harmful substances to the skin, wherein:

the external preparation contains at least one selected from the following component (AI-1), component (AI-2) and component (AI-3), and the following component (BIII), component (CIII-1) and component (CIII-2), the ratio by mass of the content of the component (BIII) to the total content of the component (AI-1), the component (AI-2) and the component (AI-3) in the external preparation, [(BIII)/[(AI-1)+(AI-2)+(AI-3)]] is 0.70 or less and 0.03 or more, the ratio by mass of the total content of the component (BIII) and the component (CIII-2) to the total content of the component (AI-1), the component (AI-2) and the component (AI-3) in the external preparation, [[(BIII)+(CIII-2)]/[(AI-1)+(AI-2)+(A3)]] is 2 or less and 0.1 or more, the ratio by mass of the total content of the component (BIII), the component (CIII-1) and the component (CIII-2) to the total content of the component (AI-1), the component (AI-2) and the component (AI-3) in the external preparation, [[(BIII)+(CIII-1)+(CIII-2)]/[(AI-1)+(AI-2)+(AI-3)]] is 4 or less and 0.1 or more, and the total content of the component (AI-1), the component (AI-2) and the component (AI-3) in the external preparation is 1% by mass or more and 40% by mass or less:

Component (AI-1): at least one selected from the group consisting of fatty acid-treated titanium oxide and zinc oxide having an average primary particle diameter $d_{AI}$ of 5 nm or more and 50 nm or less.

Component (AI-2): at least one selected from the group consisting of alkylalkoxysilane-treated titanium oxide and zinc oxide having an average primary particle diameter $d_{AI}$ of 5 nm or more and 50 nm or less.

Component (AI-3): at least one selected from the group consisting of silicone-treated titanium oxide and zinc oxide having an average primary particle diameter $d_{AI}$ of 5 nm or more and 50 nm or less.

Component (BIII): a nonvolatile silicone oil.

Component (CIII-1): an ester oil.

Component (CIII-2): a nonvolatile hydrocarbon oil.

<76> The method for suppressing adhesion of air harmful substances according to any of the above <69> to <75>, wherein the external preparation is a water-in-oil type and the total content of the component (AI-1), the component (AI-2) and the component (AI-3) in the external preparation is 10% by mass or more and 40% by mass or less.

<77> The method for suppressing adhesion of air harmful substances according to any of the above <69> to <75>, wherein the external preparation is an oil-in-water type and the total content of the component (AI-1), the component (AI-2) and the component (AI-3) in the external preparation is 1% by mass or more and 15% by mass or less.

<78> The method for suppressing adhesion of air harmful substances according to any of the above <69> to <77>, wherein the content of the component (BIII) in the external preparation is 1% by mass or more and 6% by mass or less.

<79> The method for suppressing adhesion of air harmful substances according to any of the above <69> to <78>, wherein the total coating amount on skin of the component (AI-1), the component (AI-2) and the component (AI-3) is 0.05 mg/cm² or more and 0.8 mg/cm² or less.

<80> The method for suppressing adhesion of air harmful substances according to any of the above <69> to <78>, wherein the total coating amount on skin of the component (AI-1), the component (AI-2) and the component (AI-3) is 0.07 g/cm² or more and 0.7 mg/cm² or less.

EXAMPLES

In the following Examples and Comparative Examples, "part" and "%" are "part by mass" and "% by mass", respectively, unless otherwise specified.

(Average Primary Particle Diameter $d_A$ of Metal Oxide (A) and Average Primary Particle Diameter $d_{AI}$ of Component (AI))

In the case where the metal oxide (A) or the component (AI) has any other shape than a tabular one, a dispersion of the metal oxide (A) or the component (AI) prepared previously was put on a stage of a transmission electron microscope (TEM) (trade name "JEM1400Plus" by JEOL Corporation), air-dried thereon, and the maximum minor diameter of each of 300 primary particles on the image taken by TEM at an observation magnification of 50,000× was measured, and the resultant data were averaged to give a number-average value to be the average primary particle diameter $d_A$ or the average primary particle diameter daI. Here, the maximum minor diameter means a minor diameter having a maximum length of minor diameters perpendicular to the major diameter.

In the case where the metal oxide (A) or the component (AI) is a tabular one, the thickness of each of 300 primary particles was measured on the image taken according to the same method and under the same observation magnification condition as above, and the resultant data were averaged to give a number-average value to be the average primary particle diameter $d_A$ or the average primary particle diameter $d_{AI}$.

A dispersion of the metal oxide (A) or the component (AI) was prepared by ultrasonically dispersing 5 g of the metal oxide (A) or the component (AI) in 95 g of a solvent, ethanol added thereto.

(Kinematic Viscosity at 25° C.)

The kinematic viscosity at 25° C. was measured using a Ubellohde's viscometer according to ASTM D 445-46T or JIS Z 8803.

In Examples and Comparative Examples, commercial products of the metal oxide (A) shown in Table 1 or those of the component (AI) shown in Table 2 were used.

TABLE 1

| | Metal Oxide (A) | | Shape of Metal Oxide (A) | Average Primary Particle Diameter $d_A$ (nm) | Type of Surface Treatment |
|---|---|---|---|---|---|
| No. | Type | Trade Name | | | |
| A1 | Hydrophobized Zinc Oxide | MZ-504R3M (by Tayca Corporation) | spherical | 20 | silicone treatment |
| A2 | Hydrophobized Titanium Oxide | MPT-171 (by Ishihara Sangyo Kaisha Ltd.) | spindle-shaped | 15 | stearic acid treatment |
| A3 | Hydrophobized Zinc Oxide | FINEX-50-OTS (by Sakai Chemical Industry Co., Ltd) | spherical | 20 | octyltriethoxysilane treatment |
| A4 | Hydrophobized Titanium Oxide | JR-800S (by Tayca Corporation) | spindle-shaped | 270 | silicone treatment |
| A5 | Hydrophobized Titanium Oxide | MPY-70M (by Tayca Corporation) | spindle-shaped | 700 | silicone treatment |
| A6 | Hydrophobized Zinc Oxide | D-FZN (by Daito Chemical Industry Co., Ltd.) | tabular | 20 | silicone treatment |

TABLE 1-continued

| | Metal Oxide (A) | | Shape of Metal Oxide | Average Primary Particle Diameter | Type of |
|---|---|---|---|---|---|
| No. | Type | Trade Name | (A) | $d_A$ (nm) | Surface Treatment |
| A7 | Hydrophilized Titanium Oxide | STR-100W (by Sakai Chemical Industry Co., Ltd.) | spindle-shaped | 15 | hydrous silica treatment |
| AC1 | Titanium Oxide | MP-100 (by Tayca Corporation) | spindle-shaped | 1000 | untreated |

TABLE 2

| | Component (AI) Type | Trade Name | Shape of Component (AI) | Average Primary Particle Diameter $d_{AI}$ (nm) |
|---|---|---|---|---|
| Component (AI-1) | Stearic Acid-Treated Titanium Oxide A1-1 | STR-100C-LF (by Sakai Chemical Industry Co., Ltd.) | spindle-shaped | 10 |
| Component (AI-2) | Octyltriethoxysilane-Treated Titanium Oxide A2-1 | STR-100C-OTS (by Sakai Chemical Industry Co., Ltd.) | spindle-shaped | 10 |
| Component (AI-3) | Silicone-Treated Titanium Oxide A3-1 | STR-100A-LP (by Sakai Chemical Industry Co., Ltd.) | spindle-shaped | 10 |
| | Silicone-Treated Zinc Oxide A3-2 | MICRO ZINC OXIDE MZ-504R3M (by Tayca Corporation) | spherical | 20 |

Examples 1-1 to 1-9, Comparative Example 1-1

According to the formulation shown in Table 3, the metal oxide (A) and a volatile oil were stirred and mixed at room temperature to give samples used in Examples 1-1 to 1-9 and Comparative Example 1-1. As the volatile oil, dodecamethylpentasiloxane ("KF-96L-2cs" by Shin-Etsu Chemical Industry Co., Ltd., kinematic viscosity at 25° C.: 2 mm²/s) was used.

The adhesion suppressing effect against air harmful substances of the resultant samples was evaluated according to the method (1) mentioned below. The results are shown in Table 3.

Examples 1-10 to 1-13, Example 1-15, Comparative Example 1-2

3.5 parts of the metal oxide (A) shown in Table 4 and 96.5 parts of ethanol were stirred and mixed to prepare samples used in Examples 1-10 to 1-13, Example 1-15 and Comparative Example 1-2.

The adhesion suppressing effect against air harmful substances of the resultant samples was evaluated according to the method (1) mentioned below. The results are shown in Table 4.

Example 1-14

5 parts of the metal oxide (A) shown in Table 4 and 95 parts of ethanol were stirred and mixed to prepare a sample used in Examples 1-14.

The adhesion suppressing effect against air pollutants of the resultant sample was evaluated according to the method (1) mentioned below. The results are shown in Table 4.

<Evaluation Method (1) for Adhesion Suppressing Effect Against Air Harmful Substances>

The sample prepared in Examples and Comparative Examples was applied to a white artificial leather (trade name, "Laforet S2923" by Okamoto Shinwa Co., Ltd.) as a substitute for skin to have a coating amount of the metal oxide (A) shown in Table 3 and Table 4, and left overnight at room temperature to be dried.

The surface of the artificial leather coated with the metal oxide (A) was exposed to an air flow environment of air harmful substances for evaluation, and using a colorimeter, the L*a*b* value was measured, and a color difference ΔE before and after exposure was measured according to the following method.

[Measurement of Color Difference ΔE]

Using a colorimeter (trade name "CM-2002" by Konica Minolta Corporation), the $L_1*a_1*b_1*$ value of the surface of the artificial leather coated with the metal oxide (A), before exposed to air harmful substances for evaluation was measured.

Separately, a fan (trade name "Silky Wind 9ZF002RH02", size: 129×106×83 mm, by Rhythm Co., Ltd.) and a wire sieve (test sieve by JIS Z 8801, frame dimension: φ100×45 H, opening: 106 μm, by Tokyo Screen Co., Ltd.) were fixed in a glove bag (part number "3-118-01", by AS ONE Corporation). The installation height of the wire sieve was 17 cm.

The artificial leather (5 cm×4 cm) coated with the metal oxide (A) of the test sample was attached to a support so that the height of the lower end of the artificial leather was 11 cm. The distance between the coated surface of the artificial leather on the support and the fan was 15 cm, and as shown in FIG. 1, the coated surface of the artificial leather was set to be perpendicular to the blowing direction of the fan, and the height of the center of the blade of the fan was to be the same as the height of the center of the artificial leather.

pressing ratio indicates a more excellent adhesion suppressing effect against air harmful substances.

$$\text{Adhesion suppressing ratio against air harmful substances (\%)} = 100 \times (\Delta Es - \Delta Et)/\Delta Es \quad (1\text{-II})$$

TABLE 3

|  | No. | Sample Formulation Metal Oxide (A) Content in Sample (mass %) | Volatile Oil Content in Sample (mass %) | Coating Amount of Metal Oxide (A) (mg/cm$^2$) | Adhesion Suppressing Ratio against air harmful substances (%) |
|---|---|---|---|---|---|
| Example | 1-1 A1 | 2 | 98 | 0.04 | 39 |
|  | 1-2 A1 | 3 | 97 | 0.06 | 49 |
|  | 1-3 A1 | 4 | 96 | 0.08 | 82 |
|  | 1-4 A1 | 5 | 95 | 0.10 | 86 |
|  | 1-5 A1 | 10 | 90 | 0.20 | 97 |
|  | 1-6 A1 | 15 | 85 | 0.30 | 93 |
|  | 1-7 A1 | 20 | 80 | 0.40 | 95 |
|  | 1-8 A1 | 25 | 75 | 0.50 | 93 |
|  | 1-9 A1 | 30 | 70 | 0.60 | 96 |
| Comparative Example | 1-1 A1 | 1 | 99 | 0.02 | 16 |

TABLE 4

|  | No. | Metal Oxide (A) Shape | Average Primary Particle Diameter $d_A$ (nm) | Coating Amount of Metal Oxide (A) (mg/cm$^2$) | Adhesion Suppressing Ratio against air harmful substances (%) |
|---|---|---|---|---|---|
| Example | 1-10 A2 | spindle-shaped | 15 | 0.07 | 85 |
|  | 1-11 A3 | spherical | 20 | 0.07 | 89 |
|  | 1-12 A4 | spindle-shaped | 270 | 0.07 | 63 |
|  | 1-13 A5 | spindle-shaped | 700 | 0.07 | 33 |
|  | 1-14 A6 | tabular | 20 | 0.10 | 82 |
|  | 1-15 A7 | spindle-shaped | 15 | 0.07 | 88 |
| Comparative Example | 1-2 AC1 | spindle-shaped | 1000 | 0.07 | 17 |

The temperature in the glove bag was 25° C. and the relative humidity therein was 57% RH. Using a brush for removing clogging from the wire sieve (trade name "JNB-5", brush diameter 53 μm, by Tokyo Screen Co., Ltd.), 50 mg of a graphite powder (trade name, "J-CPB", average particle diameter: 5.5 μm, by Nippon Graphite Industries, Ltd.), as air harmful substances for evaluation was, while classified, dropped down for 1 minute before the blowout port of the fan whose blowout grade was set at 1. In that manner, the surface of the artificial leather coated with the metal oxide (A) was exposed to the air flow environment of air harmful substances for evaluation.

Next, using the above colorimeter, the $L_2^*$, $a_2^*$, $b_2^*$ values of the exposed surface of the artificial leather were measured, and the color difference ΔE value was calculated according to the following formula (1-I).

$$\Delta E = [(L_1^* - L_2^*)^2 + (a_1^* - a_2^*)^2 + (b_1^* - b_2^*)^2]^{0.5} \quad (1\text{-I})$$

The above operation was repeated three times for every sample, and the mean value of the color difference ΔE of the artificial leather coated with the metal oxide (A) of the test sample was referred to as ΔEt. Further, an artificial leather not coated with the metal oxide (A) as a standard sample was treated three times in the same manner as above, and the mean value of the color difference ΔE was referred to as ΔEs. According to the following formula (1-II), the adhesion suppressing ratio was calculated. A higher adhesion sup- From Table 3, it is known that, in Examples 1-1 to 1-9, the metal oxide (A) having an average primary particle diameter $d_A$ falling within a predetermined range was applied in an amount of 0.03 mg/cm$^2$ or more, and therefore, the samples have a higher adhesion suppressing effect as compared with that in Comparative Example 1-1.

From Table 4, it is known that, in Examples 1-10 to 1-15, the metal oxide (A) having an average primary particle diameter $d_A$ of 800 nm or less was applied in a predetermined coating amount, and therefore, the samples have a higher adhesion suppressing effect as compared with that in Comparative Example 1-2.

Examples 2-1 to 2-13, Comparative Examples 2-1 to 2-8, Reference Examples 2-1 to 2-4

According to the formulation shown in Tables 5 to 9, the component (AI) or the component (AI'), and the component (BI) and the component (D) were stirred and mixed at room temperature to prepare external preparations of Examples 2-1 to 2-13, and Comparative Examples 2-1 to 2-8.

As the component (BI), isopropyl palmitate (trade name "Exeparl IPP" by Kao Corporation) was used. As the component (D), dodecamethylpentasiloxane (trade name "KF-96L-2cs" by Shin-Etsu Chemical Industry Co., Ltd., kinematic viscosity at 25° C.: 2 mm$^2$/s) was used.

As the component (AI'), a methylsiloxane network polymer ("Tospearl 145A" by Momentive Performance Materials Japan Ltd. (true spherical silicone fine particles, average particle diameter: 4.5 μm (catalogue value))) and silica particles ("Sunsphere NP-30" by AGC SI-Tec Co., Ltd., (average particle diameter: 4 μm (catalogue value))) were used.

In Reference Examples 2-1 to 2-4, the component (BI) was not used, and the component (AI) and the component (D) were stirred and mixed according to the formulation shown in Tables 5 to 8 to give external preparations.

The resultant external preparations were evaluated for the adhesion suppressing effect against air harmful substances according to the following method (2). The results are shown in Tables 5 to 9.

<Evaluation Method (2) for Adhesion Suppressing Effect Against Air Harmful Substances>

The sample prepared in the above was applied to a white artificial leather (trade name, "Laforet S2923" by Okamoto Shinwa Co., Ltd.) as a substitute for skin to have a coating amount of the component (AI) or the component (AI') of 0.12 mg/cm², and left overnight at room temperature to be dried.

The surface of the artificial leather coated with the external preparation was exposed to an air flow environment of air harmful substances for evaluation, and using a colorimeter, the L*a*b*value was measured, and a color difference ΔE before and after exposure was measured according to the following method.

[Measurement of Color Difference ΔE]

Using a colorimeter (trade name "CM-2002" by Konica Minolta Corporation), the $L_1{}^*a_1{}^*b_1{}^*$ value of the surface of the artificial leather coated with the external preparation, before exposed to air harmful substances for evaluation was measured.

Separately, a fan (trade name "Silky Wind 9ZF002RH02", size: 129×106×83 mm, by Rhythm Co., Ltd.) and a wire sieve (test sieve by JIS Z 8801, frame dimension: φ100×45 H, opening: 106 μm, by Tokyo Screen Co., Ltd.) were fixed in a glove bag (part number "3-118-01", by AS ONE Corporation). The installation height of the wire sieve was 17 cm.

The artificial leather (5 cm×4 cm) coated with the external preparation of the test sample was attached to a support so that the height of the lower end of the artificial leather was 11 cm. The distance between the coated surface of the artificial leather on the support and the fan was 15 cm, and as shown in FIG. 1, the coated surface of the artificial leather was set to be perpendicular to the blowing direction of the fan, and the height of the center of the blade of the fan was to be the same as the height of the center of the artificial leather.

The temperature in the glove bag was 25° C. and the relative humidity therein was 57% RH. Using a brush for removing clogging from the wire sieve (trade name "JNB-5", brush diameter 53 μm, by Tokyo Screen Co., Ltd.), 50 mg of a graphite powder (trade name, "J-CPB", average particle diameter: 5.5 μm, by Nippon Graphite Industries, Ltd.), as air harmful substances for evaluation was, while classified, dropped down for 1 minute before the blowout port of the fan whose blowout grade was set at 1. In that manner, the surface of the artificial leather coated with the external preparation was exposed to the air flow environment of air harmful substances for evaluation.

Next, using the above colorimeter, the $L_2{}^*$, $a_2{}^*$, $b_2{}^*$ values of the exposed surface of the artificial leather were measured, and the color difference ΔE value was calculated according to the following formula (2-I).

$$\Delta E = [(L_1{}^*-L_2{}^*)^2+(a_1{}^*-a_2{}^*)^2+(b_1{}^*-b_2{}^*)^2]^{0.5} \quad (2\text{-}I)$$

The above operation was repeated three times for every sample, and the mean value of the color difference ΔE of the artificial leather coated with the external preparation of the test sample was referred to as ΔEt. Further, an artificial leather not coated with the external preparation as a standard sample was treated three times in the same manner as above, and the mean value of the color difference ΔE was referred to as ΔEs. According to the following formula (2-II), the adhesion suppressing ratio was calculated. A higher adhesion suppressing ratio indicates a more excellent adhesion suppressing effect against air harmful substances.

$$\text{Adhesion suppressing ratio against air harmful substances (\%)} = 100 \times (\Delta E - \Delta Et)/\Delta E\Sigma \quad (2\text{-}II)$$

TABLE 5

| | | | Reference Example | Example | | | | Comparative Example | |
|---|---|---|---|---|---|---|---|---|---|
| | | | 2-1 | 2-1 | 2-2 | 2-3 | 2-4 | 2-1 | 2-2 |
| Formulation of External Preparation (mass %) | Component (AI-1) | stearic acid-treated titanium oxide A1-1 | 6 | 6 | 6 | 6 | 6 | 6 | 6 |
| | Component (BI) | isopropyl palmitate | 0 | 12 | 18 | 36 | 48 | 60 | 94 |
| | Component (D) | dodecamethylpentasiloxane | 94 | 82 | 76 | 58 | 46 | 34 | 0 |
| | Total | | 100 | 100 | 100 | 100 | 100 | 100 | 100 |
| Mass Ratio [(BI)/(AI-1)] in external preparation | | | 0 | 2 | 3 | 6 | 8 | 10 | 16 |
| Coating Amount of Component (AI-1) (mg/cm²) | | | 0.12 | 0.12 | 0.12 | 0.12 | 0.12 | 0.12 | 0.12 |
| Evaluation | Adhesion Suppressing Ratio (%) | | 86 | 87 | 87 | 64 | 56 | −39 | −100 |

TABLE 6

|  |  |  | Reference Example 2-2 | Example 2-5 | Example 2-6 | Example 2-7 | Example 2-8 | Comparative Example 2-3 | Comparative Example 2-4 |
|---|---|---|---|---|---|---|---|---|---|
| Formulation of External Preparation (mass %) | Component (AI-2) | octyltriethoxysilane-treated titanium oxide A2-1 | 6 | 6 | 6 | 6 | 6 | 6 | 6 |
|  | Component (BI) | isopropyl palmitate | 0 | 12 | 18 | 36 | 48 | 60 | 94 |
|  | Component (D) | dodecamethylpentasiloxane | 94 | 82 | 76 | 58 | 46 | 34 | 0 |
|  |  | Total | 100 | 100 | 100 | 100 | 100 | 100 | 100 |
| Mass Ratio |(BI)/(AI-2)| in external preparation |  |  | 0 | 2 | 3 | 6 | 8 | 10 | 16 |
| Coating Amount of Component (AI-2) (mg/cm$^2$) |  |  | 0.12 | 0.12 | 0.12 | 0.12 | 0.12 | 0.12 | 0.12 |
| Evaluation | Adhesion Suppressing Ratio (%) |  | 95 | 98 | 98 | 91 | 79 | −35 | −126 |

TABLE 7

|  |  |  | Reference Example 2-3 | Example 2-9 | Example 2-10 | Example 2-11 | Example 2-12 | Comparative Example 2-5 |
|---|---|---|---|---|---|---|---|---|
| Formulation of External Preparation (mass %) | Component (AI-3) | silicone-treated titanium oxide A3-1 | 6 | 6 | 6 | 6 | 6 | 6 |
|  | Component (BI) | isopropyl palmitate | 0 | 12 | 24 | 36 | 48 | 84 |
|  | Component (D) | dodecamethylpentasiloxane | 94 | 82 | 70 | 58 | 46 | 10 |
|  |  | Total | 100 | 100 | 100 | 100 | 100 | 100 |
| Mass Ratio [(BI)/(AI-3)] in external preparation |  |  | 0 | 2 | 4 | 6 | 8 | 14 |
| Coating Amount of Component (AI-3) (mg/cm$^2$) |  |  | 0.12 | 0.12 | 0.12 | 0.12 | 0.12 | 0.12 |
| Evaluation | Adhesion Suppressing Ratio (%) |  | 91 | 91 | 89 | 89 | 84 | −51 |

TABLE 8

|  |  |  | Reference Example 2-4 | Example 2-13 | Comparative Example 2-6 |
|---|---|---|---|---|---|
| Formulation of External Preparation (mass %) | Component (AI-3) | silicone-treated titanium oxide A3-2 | 6 | 6 | 6 |
|  | Component (BI) | isopropyl palmitate | 0 | 48 | 84 |
|  | Component (D) | dodecamethylpentasiloxane | 94 | 46 | 10 |
|  |  | Total | 100 | 100 | 100 |
| Mass Ratio [(BI)/(AI-3)] in external preparation |  |  | 0 | 8 | 14 |
| Coating Amount of Component (AI-3) (mg/cm$^2$) |  |  | 0.12 | 0.12 | 0.12 |
| Evaluation | Adhesion Suppressing Ratio (%) |  | 91 | 82 | −33 |

TABLE 9

|  |  |  | Comparative Example 2-7 | Comparative Example 2-8 |
|---|---|---|---|---|
| Formulation of External Preparation (mass %) | Component (A') | methylsiloxane network polymer | 6 | 0 |
|  |  | silica particles | 0 | 6 |
|  | Component (BI) | isopropyl palmitate | 48 | 48 |

TABLE 9-continued

|  |  | Comparative Example | |
|---|---|---|---|
|  |  | 2-7 | 2-8 |
| Component (D) | dodecamethylpentasiloxane | 46 | 46 |
|  | Total | 100 | 100 |
| Mass Ratio [(BI)/(AI')] |  | 8 | 8 |
| Coating Amount of Component (AI') (mg/cm$^2$) |  | 0.12 | 0.12 |
| Evaluation | Adhesion Suppressing Ratio (%) | −11 | 2 |

From Tables 5 to 9, it is known that, in Examples 2-1 to 2-13, the external preparation containing the component (AI) and the component (BI), in which the mass ratio of the component (BI) to the component (AI) [(BI)/(AI)] was 9 or less, was applied, and therefore, the samples have a higher adhesion suppressing effect as compared with those in Comparative Example 2-1 to 2-8.

In addition, as compared with those in Reference Examples 2-1 to 2-4, the external preparations in Examples 2-1 to 2-13 contain the component (BI) and therefore give a good feel (touch) in use.

Examples 2-14 to 2-21

External preparations shown in the following Formulation Examples 2-1 to 2-8 were prepared and evaluated in the same manner as in the evaluation method (2) for the adhesion suppressing effect against air harmful substances mentioned above, except that each preparation was applied to a white artificial leather in an amount of 2 mg/cm$^2$. The results are shown in Table 10.

Expressions in the formulation examples are as follows.
1: "STR-100C-LF" by Sakai Chemical Industry Co., Ltd.
2: "MICRO ZINC OXIDE MZ-504R3M" by Tayca Corporation
3: "Estemol N-01" by The Nisshin OilliO Group, Ltd.
4: "Parleam EX" by NOF Corporation
5: "Nikkol Squalane" by Nippon Surfactant Industries Co., Ltd.
6: "KF-96A-10CS" by Shin-Etsu Chemical Industry Co., Ltd.
7: "Sphingolipid E" by Kao Corporation
8: "KF-6015" by Shin-Etsu Chemical Industry Co., Ltd.
9: "KF-96L-2CS" by Shin-Etsu Chemical Industry Co., Ltd.
10: "Tospearl 145A" by Momentive Performance Materials Japan Ltd.
11: "SI-Talc JA-46R" by Miyoshi Kasei Inc.
12: "Exeparl TGO" by Kao Corporation
13: "KF-96A-6CS" by Shin-Etsu Chemical Industry Co., Ltd.
14: "FINEX-30-OTS(K)" by Sakai Chemical Industry Co., Ltd.
15: "Uvinul MC80" by BASF Japan Ltd.
16: "TINOSORB S" by BASF Japan Ltd.
17: "Exeparl IPP" by Kao Corporation
18: "Silicone TSF405A" by Momentive Performance Materials Japan Ltd.
19: "MPT-171" by Ishihara Sangyo Kaisha Ltd.
20: "Cetyl Alcohol NX" by Koukyu Alcohol Kogyo Co., Ltd.
21: "Montex A" by Miyoshi Oil & Fat Co., Ltd.
22: "Emulgen 1620G" by Kao Corporation
23: "PEMULEN TR-1" by Lubrizol Advanced Materials, Inc.
24: "PEMULEN TR-2" by Lubrizol Advanced Materials, Inc.
25: "STR-100W-OTS" by Sakai Chemical Industry Co., Ltd.
26: "Uvinul T150" by BASF Japan Ltd.
27: "Rheodol TW-S120V" by Kao Corporation
28: "Parleam 4" by NOF Corporation
29: "FINEX-50-LPTM" by Sakai Chemical Industry Co., Ltd.
30: "D-FZN(SI01)" by Daito Chemical Industry Co., Ltd.
31: "Cosmol 525" by Nisshin OilliO Group, Ltd.
32: "Uvinul A Plus GRANULAR" by BASF Japan Ltd.
33: "Rheodol SP-S10V" by Kao Corporation
34: "SIMULGEL EG" by SEPPIC S.A.
35: "Silicone X-52-1621" by Shin-Etsu Chemical Industry Co., Ltd.
36: "Salacos 99" by Nisshin OilliO Group, Ltd.

| Formulation Example 2-1 (W/O type external preparation, mass ratio [(BI)/(AI)] = 0.12, mass ratio [(CI-1)/(AI)] = 0.35) (Blending Components (amount)) | |
|---|---|
| Stearic acid-treated titanium oxide (component (AI-1))*1 | 7 parts |
| Silicone-treated zinc oxide (component (AI-3))*2 | 19 parts |
| Neopentyl glycol dicaprylate (component (BI))*3 | 3 parts |
| Liquid isoparaffin (component (CI-1))*4 | 6 parts |
| Squalane (component (CI-1))*5 | 3 parts |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm$^2$/s) (component D))*9 | 40.1 parts |
| Methylsiloxane network polymer*10 | 1 part |
| Silicone-coated talc*11 | 1.9 parts |
| Glycerin (86%) | 1 part |
| Pure water | balance |
| Total | 100 parts |

| Formulation Example 2-2 (W/O type external preparation, mass ratio [(BI)/(AI)] = 0.31, mass ratio [(CI-1)/(AI)] = 0.35, mass ratio [CI-2)/(AI)] = 0.04) (Blending Components (amount)) | |
|---|---|
| Stearic acid-treated titanium oxide (component (AI-1))*1 | 7 parts |

Formulation Example 2-2 (W/O type external preparation, mass ratio [(BI)/(AI)] = 0.31, mass ratio [(CI-1)/(AI)] = 0.35, mass ratio [(CI-2)/(AI)] = 0.04)
(Blending Components (amount))

| | |
|---|---|
| Silicone-treated zinc oxide (component (AI-3))*2 | 19 parts |
| Neopentyl glycol dicaprylate (component (BI))*3 | 3 parts |
| Glyceryl tri-2-ethylhexanoate (component (BI))*12 | 5 parts |
| Liquid isoparaffin (component (CI-1))*4 | 5 parts |
| Squalane (component (CI-1))*5 | 4 parts |
| Dimethylpolysiloxane (25° C. kinematic viscosity: 10 mm$^2$/s) (component CI-2))*6 | 1 part |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm$^2$/s) (component D))*9 | 35.1 parts |
| Methylsiloxane network polymer*10 | 3 parts |
| Silicone-coated talc*11 | 1.9 parts |
| Glycerin (86%) | 1 part |
| Pure water | balance |
| Total | 100 parts |

Formulation Example 2-3 (W/O type external preparation) (mass ratio [(BI)/(AI)] = 0.12, mass ratio [(CI-1)/(AI)] = 0.35, mass ratio [(CI-2)/(AI)] = 0.23)
(Blending Components (amount))

| | |
|---|---|
| Stearic acid-treated titanium oxide (component (AI-1))*1 | 7 parts |
| Silicone-treated zinc oxide (component (AI-3))*2 | 19 parts |
| Neopentyl glycol dicaprylate (component (BI))*3 | 3 parts |
| Liquid isoparaffin (component (CI-1))*4 | 7 parts |
| Squalane (component (CI-1))*5 | 2 parts |
| Dimethylpolysiloxane (25° C. kinematic viscosity: 10 mm$^2$/s) (component CI-2))*6 | 1 part |
| Dimethylpolysiloxane (25° C. kinematic viscosity: 6 mm$^2$/s) (component CI-2))*13 | 5 parts |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm$^2$/s) (component D))*9 | 35.1 parts |
| Glycerin (86%) | 1 part |
| Pure water | balance |
| Total | 100 parts |

Formulation Example 2-4 (W/O type external preparation) (mass ratio [(BI)/(AI)] = 0.97, mass ratio [(CI-2)/(AI)] = 0.27)
(Blending Components (amount))

| | |
|---|---|
| Octyltriethoxysilane-treated zinc oxide (component )AI-2))*14 | 15 parts |
| 2-Ethylhexyl paramethoxycinnamate (component (BI))*15 | 10 parts |
| Neopentyl glycol dicaprylate (component (BI))*3 | 3 parts |
| Isopropyl palmitate (component (BI))*17 | 1.5 parts |
| Dimethylpolysiloxane (25° C. kinematic viscosity: 6 mm$^2$/s) (component CI-2))*13 | 4 parts |
| 2,4-Bis-[{4-(2-ethylhexyloxy)-2-hydroxy}-phenyl]-6-(4-methoxyphenyl)-1,3,5-triazine*16 | 2 parts |
| Polyoxyethylene/methylpolysiloxane copolymer (HLB: 4.5)*8 | 0.8 parts |
| Dodecamethylpentasiloxane (25° C. kinematic viscosity: 2 mm$^2$/s) (component D))*9 | 5 parts |
| Decamethylcyclopentasiloxane (25° C. kinematic viscosity: 4 mm$^2$/s) (component D))*18 | 28.7 parts |
| Silicone-coated talc*11 | 2 parts |
| Ethanol | 11 parts |
| 1,3-Butylene glycol | 2 parts |
| Pure water | balance |
| Total | 100 parts |

Formulation Example 2-5 (O/W type external preparation, mass ratio [(BI)/(AI)] = 3.0, mass ratio [(CI-2)/(AI)] = 0.25)
(Blending Components (amount))

| | |
|---|---|
| Stearic acid-treated titanium oxide (component (AI-1))*19 | 4 parts |
| Isopropyl palmitate (component (BI))*17 | 4 parts |
| 2-Ethylhexyl paramethoxycinnamate (component (BI))*15 | 8 parts |
| Dimethylpolysiloxane (25° C. kinematic viscosity: 10 mm$^2$/s) (component CI-2))*6 | 1 part |
| 2,4-Bis-[{4-(2-ethylhexyloxy)-2-hydroxy}-phenyl]-6-(4-methoxyphenyl)-1,3,5-triazine*16 | 1 part |
| Cetanol*20 | 0.2 parts |
| Glyceryl monostearate*21 | 0.3 parts |
| Isoceteth-20*22 | 0.03 parts |
| Acrylates/C10-30 alkyl acrylate cross polymer*23 | 0.2 parts |
| Acrylates/C10-30 alkyl acrylate cross polymer*24 | 0.2 parts |
| EDTA-2Na | 0.01 parts |
| Phenoxyethanol | 0.5 parts |
| Potassium hydroxide (48%) | 0.4 parts |
| Ethanol | 5 parts |
| Pure water | balance |
| Total | 100 parts |

Formulation Example 2-6 (O/W type external preparation, mass ratio [(BI)/(AI)] = 3.5, mass ratio [(CI-2)/(AI)] = 0.25)
(Blending Components (amount))

| | |
|---|---|
| Octyltriethoxysilane-treated titanium oxide (component (AI-2))*25 | 4 parts |
| Isopropyl palmitate (component (BI))*17 | 4 parts |

Formulation Example 2-6 (O/W type external preparation, mass ratio [(BI)/(AI)] = 3.5, mass ratio [(CI-2)/(AI)] = 0.25) (Blending Components (amount))

| | |
|---|---|
| 2-Ethylhexyl paramethoxycinnamate (component (BI))*15 | 8 parts |
| 2,4,6-Tris[4-(2-ethylhexyloxycarbonyl) anilino-1,3,5-triazine (component (BI))*26 | 2 parts |
| Dimethylpolysiloxane (25° C. kinematic viscosity: 10 mm²/s) (component CI-2))*6 | 1 part |
| 2,4-Bis-[{4-(2-ethylhexyloxy)-2-hydroxy}-phenyl]-6-(4-methoxyphenyl)-1,3,5-triazine*16 | 2 parts |
| Cetanol*20 | 0.2 parts |
| Glyceryl monostearate*21 | 0.3 parts |
| Isoceteth-20*22 | 0.03 parts |
| Polyoxyethylene sorbitan monostearate*27 | 0.1 parts |
| Acrylates/C10-30 alkyl acrylate cross polymer*23 | 0.2 parts |
| Acrylates/C10-30 alkyl acrylate cross polymer*24 | 0.2 parts |
| Light liquid isoparaffin (component (D))*28 | 1 part |
| EDTA-2Na | 0.01 parts |
| Phenoxyethanol | 0.5 parts |
| 1,3-Butylene glycol | 5 parts |
| Potassium hydroxide (48%) | 0.6 parts |
| Ethanol | 5 parts |
| Pure water | balance |
| Total | 100 parts |

Formulation Example 2-7 (O/W type external preparation, mass ratio [(BI)/(AI)] = 1.3 ) (Blending Components (amount))

| | |
|---|---|
| Silicone-treated zinc oxide (component (AI-3))*29 | 8 parts |
| Silicone-treated zinc oxide (component (AI-3))*30 | 3 parts |
| Neopentyl glycol di-2-ethylhexanoate (component (BI))*31 | 4 parts |
| 2-Ethylhexyl paramethoxycinnamate (component (BI))*15 | 8 parts |
| Hexyl diethylaminohydroxybenzoyl-benzoate (componant (BI))*32 | 2 parts |
| 2,4-Bis-[{4-(2-ethylhexyloxy)-2-hydroxy}-phenyl]-6-(4-methoxyphenyl)-1,3,5-triazine*16 | 2 parts |
| Behenyl alcohol | 0.5 parts |
| Sorbitan monostearate*33 | 1 part |
| Polyoxyethylene sorbitan monostearate*27 | 1 part |
| Sodium acrylate/sodium acryloyl-dimethyltaurate copolymer/isohexadecane/Polysorbate 80*34 | 2 parts |
| Methylsiloxane network polymer*35 | 0.5 parts |
| 1,3-Butylene glycol | 1 part |
| EDTA-2Na | 0.01 parts |
| Ethyl alcohol | 10 parts |
| Pure water | balance |
| Total | 100 parts |

Formulation Example 2-8 (O/W type external preparation, mass ratio [(BI)/(AI)] = 1.5, mass ratio [(CI-2)/(AI)] = 0.50) (Blending Components (amount))

| | |
|---|---|
| Stearic acid-treated titanium oxide (component (AI-1))*19 | 8 parts |
| Isononyl isononanoate (component (BI))*36 | 7.6 parts |
| Neopentyl glycol dicaprylate (component (BI))*3 | 4 parts |
| Dimethylpolysiloxane (25° C. kinematic viscosity: 6 mm²/s) (component (CI-2))*13 | 4 parts |
| Sorbitan monostearate*33 | 0.7 parts |
| Polyoxyethylene sorbitan monostearate*27 | 1 part |
| Stearyl alcohol | 1 part |
| Acrylates/C10-30 alkyl acrylate cross polymer*23 | 0.07 parts |
| Acrylates/C10-30 alkyl acrylate cross polymer*24 | 0.25 parts |
| Potassium hydroxide (48%) | 0.4 parts |
| 1,3-Butylene glycol | 8 parts |
| EDTA-2Na | 0.02 parts |
| Pure water | balance |
| Total | 100 parts |

TABLE 10

| | | Example | | | | | | | |
|---|---|---|---|---|---|---|---|---|---|
| | | 2-14 | 2-15 | 2-16 | 2-17 | 2-18 | 2-19 | 2-20 | 2-21 |
| Formulation Example of External Preparation | | 2-1 | 2-2 | 2-3 | 2-4 | 2-5 | 2-6 | 2-7 | 2-8 |
| Formulation of External Preparation (mass %) | Component (AI) | 26 | 26 | 26 | 15 | 4 | 4 | 11 | 8 |
| | Component (BI) | 3 | 8 | 3 | 14.5 | 12 | 14 | 14 | 11.6 |
| Mass Ratio [(BI)/(AI)] in External Preparation | | 0.12 | 0.31 | 0.12 | 0.97 | 3.0 | 3.5 | 1.3 | 1.5 |
| Coating Amount of Component (AI) (mg/cm²) | | 0.52 | 0.52 | 0.52 | 0.30 | 0.08 | 0.08 | 0.22 | 0.16 |
| Evaluation | Adhesion Suppressing Ratio (%) | 63 | 70 | 33 | 60 | 67 | 67 | 63 | 51 |

From Table 10, it is known that, in Examples 2-14 to 2-21, the external preparation of Formulation Examples 2-1 to 2-8 was applied, and therefore, the samples have an adhesion suppressing effect.

In addition, as compared with those in Reference Examples 2-1 to 2-4, the external preparations used in Examples 2-14 to 2-21 contain the component (BI) and therefore give a good feel (touch) in use.

Examples 3-1 to 3-22, Comparative Examples 3-1 to 3-10, Reference Examples 3-1 to 3-4

According to the formulation shown in Tables 11 to 15, the component (AI) or the component (AI'), and the component (BII) and the component (D) were stirred and mixed at room temperature to give external preparations in Examples 3-1 to 3-22, and Comparative Examples 3-1 to 3-10.

As the component (BII), used was liquid isoparaffin (trade name "Parleam EX", hydrogenated polyisobutene, by NOF Corporation), and as the component (D), used was dodecamethylpentasiloxane (trade name "KF-96L-2cs", 25° C. kinematic viscosity: 2 mm$^2$/s, by Shin-Etsu Chemical Industry Co., Ltd.). The component (AI') is as mentioned above.

In Reference Examples 3-1 to 3-4, the component (BII) was not used, and the component (AI) and the component (D) were stirred and mixed according to the formulation shown in Tables 11 to 14 to prepare external preparations.

The resultant external preparations were evaluated for the adhesion suppressing effect against air harmful substances according to the above-mentioned evaluation method (2). The results are shown in Tables 11 to 15.

TABLE 11

| | | | Reference Example | Example | | | | | | | Comparative Example | |
|---|---|---|---|---|---|---|---|---|---|---|---|---|
| | | | 3-1 | 3-1 | 3-2 | 3-3 | 3-4 | 3-5 | 3-6 | 3-7 | 3-1 | 3-2 |
| Formulation of External Preparation (mass %) | Component (AI-1) | stearic acid-treated titanium oxide A1-1 | 6 | 6 | 6 | 6 | 6 | 6 | 6 | 6 | 6 | 6 |
| | Component (BII) | liquid isoparaffin | 0 | 2 | 4 | 6 | 8 | 10 | 12 | 18 | 24 | 36 |
| | Component (D) | dodecamethyl-pentasiloxane | 94 | 92 | 90 | 88 | 86 | 84 | 82 | 76 | 70 | 58 |
| | | Total | 100 | 100 | 100 | 100 | 100 | 100 | 100 | 100 | 100 | 100 |
| Mass Ratio [(BII)/(AI-1)] | | | 0 | 0.33 | 0.67 | 1.0 | 1.3 | 1.7 | 2.0 | 3.0 | 4.0 | 6.0 |
| Coating Amount of Component (AI-1) (mg/cm$^2$) | | | 0.12 | 0.12 | 0.12 | 0.12 | 0.12 | 0.12 | 0.12 | 0.12 | 0.12 | 0.12 |
| Evaluation | Adhesion Suppressing Ratio (%) | | 86 | 90 | 89 | 85 | 85 | 87 | 85 | 63 | 0 | −70 |

TABLE 12

| | | | Reference Example | Example | | | | |
|---|---|---|---|---|---|---|---|---|
| | | | 3-2 | 3-8 | 3-9 | 3-10 | 3-11 | 3-12 |
| Formulation of External Preparation (mass %) | Component (AI-2) | octyltriethoxysilane-treated titanium oxide A2-1 | 6 | 6 | 6 | 6 | 6 | 6 |
| | Component (BII) | 1 liquid isoparaffin | 0 | 2 | 4 | 6 | 8 | 10 |
| | Component (D) | dodecamethyl-pentasiloxane | 94 | 92 | 90 | 88 | 86 | 84 |
| | | Total | 100 | 100 | 100 | 100 | 100 | 100 |
| Mass Ratio [(BII)/(AI-2)] | | | 0 | 0.33 | 0.67 | 1.0 | 1.3 | 1.7 |
| Coating Amount of Component (AI-2) (mg/cm$^2$) | | | 0.12 | 0.12 | 0.12 | 0.12 | 0.12 | 0.12 |
| Evaluation | Adhesion Suppressing Ratio (%) | | 95 | 98 | 99 | 98 | 98 | 97 |

| | | | Example | | Comparative Example | | |
|---|---|---|---|---|---|---|---|
| | | | 3-13 | 3-14 | 3-3 | 3-4 | 3-5 |
| Formulation of External Preparation (mass %) | Component (AI-2) | octyltriethoxysilane-treated titanium oxide A2-1 | 6 | 6 | 6 | 6 | 6 |
| | Component (BII) | 1 liquid isoparaffin | 12 | 18 | 24 | 30 | 36 |
| | Component (D) | dodecamethyl-pentasiloxane | 82 | 76 | 70 | 64 | 58 |
| | | Total | 100 | 100 | 100 | 100 | 100 |
| Mass Ratio [(BII)/(AI-2)] | | | 2.0 | 3.0 | 4.0 | 5.0 | 6.0 |
| Coating Amount of Component (AI-2) (mg/cm$^2$) | | | 0.12 | 0.12 | 0.12 | 0.12 | 0.12 |
| Evaluation | Adhesion Suppressing Ratio (%) | | 96 | 69 | −60 | −101 | −132 |

TABLE 13

|  |  |  | Reference Example | Example | | | | | Comparative Example | |
| --- | --- | --- | --- | --- | --- | --- | --- | --- | --- | --- |
|  |  |  | 3-3 | 3-15 | 3-16 | 3-17 | 3-18 | 3-19 | 3-6 | 3-7 |
| Formulation of External Preparation (mass %) | Component (AI-3) | silicone-treated titanium oxide A3-1 | 6 | 6 | 6 | 6 | 6 | 6 | 6 | 6 |
|  | Component (BII) | liquid isoparaffin | 0 | 4 | 6 | 8 | 12 | 18 | 36 | 42 |
|  | Component (D) | dodecamethyl-pentasiloxane | 94 | 90 | 88 | 86 | 82 | 76 | 58 | 52 |
|  | Total |  | 100 | 100 | 100 | 100 | 100 | 100 | 100 | 100 |
| Mass Ratio [(BII)/(AI-3)] |  |  | 0 | 0.67 | 1.0 | 1.3 | 2.0 | 3.0 | 6.0 | 7.0 |
| Coating Amount of Component (AI-3) (mg/cm$^2$) |  |  | 0.12 | 0.12 | 0.12 | 0.12 | 0.12 | 0.12 | 0.12 | 0.12 |
| Evaluation | Adhesion Suppressing Ratio (%) |  | 90 | 89 | 90 | 89 | 88 | 90 | −10 | −21 |

TABLE 14

|  |  |  | Reference Example | Example | | | Comparative Example |
| --- | --- | --- | --- | --- | --- | --- | --- |
|  |  |  | 3-4 | 3-20 | 3-21 | 3-22 | 3-8 |
| Formulation of External Preparation (mass %) | Component (AI-3) | silicone-treated zinc oxide A3-2 | 6 | 6 | 6 | 6 | 6 |
|  | Component (BII) | liquid isoparaffin | 0 | 8 | 12 | 18 | 30 |
|  | Component (D) | dodecamethyl-pentasiloxane | 94 | 86 | 82 | 76 | 64 |
|  | Total |  | 100 | 100 | 100 | 100 | 100 |
| Mass Ratio [(BII)/(AI-3)] |  |  | 0 | 1.3 | 2.0 | 3.0 | 5.0 |
| Coating Amount of Component (AI-3) (mg/cm$^2$) |  |  | 0.12 | 0.12 | 0.12 | 0.12 | 0.12 |
| Evaluation | Adhesion Suppressing Ratio (%) |  | 90 | 78 | 71 | 76 | −35 |

TABLE 15

|  |  |  | Comparative Example | |
| --- | --- | --- | --- | --- |
|  |  |  | 3-9 | 3-10 |
| Formulation of External Preparation (mass %) | Component (AI') | methylsiloxane network polymer | 6 | 0 |
|  |  | silica particles | 0 | 6 |
|  | Component (BII) | liquid isoparaffin | 18 | 18 |
|  | Component (D) | dodecamethyl-pentasiloxane | 76 | 76 |
|  | Total |  | 100 | 100 |
| Mass Ratio [(BII)/(AI')] |  |  | 3.0 | 3.0 |
| Coating Amount of Component (AI') (mg/cm$^2$) |  |  | 0.12 | 0.12 |
| Evaluation | Adhesion Suppressing Ratio (%) |  | −4 | 1 |

From Tables 11 to 15, it is known that, in Examples 3-1 to 3-22, the external preparation containing the component (AI) and the component (BII), in which the mass ratio of the component (BII) to the component (AI) [(BII)/(AI)] was 3.5 or less, was applied, and therefore, the samples have a higher adhesion suppressing effect as compared with those in Comparative Example 3-1 to 3-10.

In addition, as compared with those in Reference Examples 3-1 to 3-4, the external preparations in Examples 3-1 to 3-22 contain the component (BII) and therefore give a good feel (touch) in use.

Examples 3-23 to 3-26

External preparations shown in the following Formulation Examples 3-1 to 3-4 were prepared and evaluated in the same manner as in the evaluation method (2) for the adhesion suppressing effect against air harmful substances mentioned above, except that each preparation was applied to a white artificial leather in an amount of 2 mg/cm$^2$. The results are shown in Table 16.

Expressions *1 to *13 in the formulation examples are the same as above.

Formulation Example 3-1 (W/O type external preparation, mass ratio [(CII-1)/(AI)] = 0.12, mass ratio ([BII)/(AI)] = 0.35) (Blending Components (amount))

| | |
| --- | --- |
| Stearic acid-treated titanium oxide (component (AI-1))*1 | 7 parts |
| Silicone-treated zinc oxide (component (AI-3))*2 | 19 parts |
| Neopentyl glycol dicaprylate (component (CII-1))*3 | 3 parts |
| Liquid isoparaffin (component (BII))*4 | 6 parts |
| Squalane (component (BII))*5 | 3 parts |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm$^2$/s) (component D))*9 | 40.1 parts |

Formulation Example 3-1 (W/O type external preparation, mass ratio [(CII-1)/(AI)] = 0.12, mass ratio ([BII]/(AI)] = 0.35) (Blending Components (amount))

| | |
|---|---|
| Methylsiloxane network polymer*10 | 1 part |
| Silicone-coated talc*11 | 1.9 parts |
| Glycerin (86%) | 1 part |
| Pure water | balance |
| Total | 100 parts |

Formulation Example 3-2 (W/O type external preparation, mass ratio ([CII-1)/(AI)] = 0.31, mass ratio [(BII)/(AI)] = 0.35, mass ratio [(CII-2)/(AI)] = 0.04) (Blending Components (amount))

| | |
|---|---|
| Stearic acid-treated titanium oxide (component (AI-1))*1 | 7 parts |
| Silicone-treated zinc oxide (component (AI-3))*2 | 19 parts |
| Neopentyl glycol dicaprylate (component (CII-1))*3 | 3 parts |
| Glyceryl tri-2-ethylhexanoate (component (CII-1))*12 | 5 parts |
| Liquid isoparaffin (component (BII))*4 | 5 parts |
| Squalane (component (BII))*5 | 4 parts |
| Dimethylpolysiloxane (25° C. kinematic viscosity: 10 mm²/s) (component CII-2))*6 | 1 part |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm²/s) (component D))*9 | 35.1 parts |
| Methylsiloxane network polymer*10 | 3 parts |
| Silicone-coated talc*11 | 1.9 parts |
| Glycerin (86%) | 1 part |
| Pure water | balance |
| Total | 100 parts |

Formulation Example 3-3 (W/O type external preparation) (mass ratio [(CII-1)/(AI)] = 0.12, mass ratio [(BII)/(AI)] = 0.35, mass ratio [(CII-2)/(AI)] = 0.23) (Blending Components (amount))

| | |
|---|---|
| Stearic acid-treated titanium oxide (component (AI-1))*1 | 7 parts |
| Silicone-treated zinc oxide (component (AI-3))*2 | 19 parts |
| Neopentyl glycol dicaprylate (component (CII-1))*3 | 3 parts |
| Liquid isoparaffin (component (BII))*4 | 7 parts |
| Squalane (component (BII))*5 | 2 parts |
| Dimethylpolysiloxane (25° C. kinematic viscosity: 10 mm²/s) (component CII-2))*6 | 1 part |
| Dimethylpolysiloxane (25° C. kinematic viscosity: 6 mm²/s) (component CII-2))*13 | 5 parts |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm²/s) (component D))*9 | 35.1 parts |
| Glycerin (86%) | 1 part |
| Pure water | balance |
| Total | 100 parts |

Formulation Example 3-4 (W/O type external preparation) (mass ratio [(BII)/(AI)] = 0.41, mass ratio [(CII-2)/(AI)] = 0.14) (Blending Components (amount))

| | |
|---|---|
| Stearic acid-treated titanium oxide (component (AI-1))*1 | 10 parts |
| Silicone-treated zinc oxide (component (AI-3))*2 | 19 parts |
| Liquid isoparaffin (component (BII))*4 | 10 parts |
| Squalane (component (BII))*5 | 2 parts |
| Dimethylpolysiloxane (25° C. kinematic viscosity: 10 mm²/s) (component CII-2))*6 | 1 part |
| Dimethylpolysiloxane (25° C. kinematic viscosity: 6 mm²/s) (component CII-2))*13 | 3 parts |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm²/s) (component D))*9 | 35.1 parts |
| Glycerin (86%) | 1 part |
| Pure water | balance |
| Total | 100 parts |

TABLE 16

| | | Example | | | |
|---|---|---|---|---|---|
| | | 3-23 | 3-24 | 3-25 | 3-26 |
| Formulation Example of External Preparation | | 3-1 | 3-2 | 3-3 | 3-4 |
| Formulation of External Preparation (mass %) | Component (AI) | 26 | 26 | 26 | 29 |
| | Component (BII) | 9 | 9 | 9 | 12 |
| | Mass Ratio ([BII]/(AI]) in external preparation | 0.35 | 0.35 | 0.35 | 0.41 |
| | Coating Amount of Component (AI) (mg/cm²) | 0.52 | 0.52 | 0.52 | 0.58 |
| Evaluation | Adhesion Suppressing Ratio (%) | 63 | 70 | 33 | 61 |

From Table 16, it is known that, in Examples 3-23 to 3-26, the external preparation of Formulation Examples 3-1 to 3-4 was applied, and therefore, the samples have an adhesion suppressing effect.

In addition, as compared with those in Reference Examples 3-1 to 3-4, the external preparations in Examples 3-23 to 3-26 contain the component (BII) and therefore give a good feel (touch) in use.

Examples 4-1 to 4-12, Comparative Examples 4-1 to 4-9, Reference Examples 4-1 to 4-4

According to the formulation shown in Tables 17 to 21, the component (AI) or the component (AI'), and the component (BIII) and the component (D) were stirred and mixed at room temperature to give external preparations in Examples 4-1 to 4-12, and Comparative Examples 4-1 to 4-9.

As the component (BIII), used was dimethylpolysiloxane ("KF-96L-6cs", 25° C. kinematic viscosity=6 mm$^2$/s, by Shin-Etsu Chemical Industry Co., Ltd.), and as the component (D), used was dodecamethylpentasiloxane (trade name "KF-96L-2cs", 25° C. kinematic viscosity: 2 mm$^2$/s, by Shin-Etsu Chemical Industry Co., Ltd.). The component (AI') is as mentioned above.

In Reference Examples 4-1 to 4-4, the component (BIII) was not used, and the component (AI) and the component (D) were stirred and mixed according to the formulation shown in Tables 17 to 20 to prepare external preparations.

The resultant external preparations were evaluated for the adhesion suppressing effect against air harmful substances according to the above-mentioned evaluation method (2). The results are shown in Tables 17 to 21.

TABLE 17

| | | | Reference Example | Example | | | Comparative Example | |
|---|---|---|---|---|---|---|---|---|
| | | | 4-1 | 4-1 | 4-2 | 4-3 | 4-1 | 4-2 |
| Formulation of External Preparation (mass %) | Component (AI-1) | stearic acid-treated titanium oxide A1-1 | 6 | 6 | 6 | 6 | 6 | 6 |
| | Component (BIII) | dimethylpolysiloxane (25° C. kinematic viscosity: 6 mm$^2$/sec) | 0 | 2 | 4 | 4.8 | 6 | 8 |
| | Component (D) | dodecamethylpentasiloxane | 94 | 92 | 90 | 89.2 | 88 | 86 |
| | Total | | 100 | 100 | 100 | 100 | 100 | 100 |
| Mass Ratio [(BIII)/(AI-1)] | | | 0 | 0.33 | 0.67 | 0.80 | 1.0 | 1.3 |
| Coating Amount of Component (AI-1) (mg/cm$^2$) | | | 0.12 | 0.12 | 0.12 | 0.12 | 0.12 | 0.12 |
| Evaluation | Adhesion Suppressing Ratio (%) | | 86 | 86 | 84 | 68 | −8 | −45 |

TABLE 18

| | | | Reference Example | Example | | | Comparative Example | |
|---|---|---|---|---|---|---|---|---|
| | | | 4-2 | 4-4 | 4-5 | 4-6 | 4-3 | 4-4 |
| Formulation of External Preparation (mass %) | Component (AI-2) | octyltriethoxysilane-treated titanium oxide A2-1 | 6 | 6 | 6 | 6 | 6 | 6 |
| | Component (BIII) | dimethylpolysiloxane (25° C. kinematic viscosity: 6 mm$^2$/sec) | 0 | 2 | 4 | 4.8 | 6 | 8 |
| | Component (D) | dodecamethylpentasiloxane | 94 | 92 | 90 | 89.2 | 88 | 86 |
| | Total | | 100 | 100 | 100 | 100 | 100 | 100 |
| Mass Ratio [(BIII)/(AI-2)] | | | 0 | 0.33 | 0.67 | 0.80 | 1.0 | 1.3 |
| Coating Amount of Component (AI-2) (mg/cm$^2$) | | | 0.12 | 0.12 | 0.12 | 0.12 | 0.12 | 0.12 |
| Evaluation | Adhesion Suppressing Ratio (%) | | 95 | 97 | 90 | 77 | −28 | −66 |

TABLE 19

| | | | Reference Example | Example | | Comparative Example |
|---|---|---|---|---|---|---|
| | | | 4-3 | 4-7 | 4-8 | 4-5 |
| Formulation of External Preparation (mass %) | Component (AI-3) | silicone-treated titanium oxide A3-1 | 6 | 6 | 6 | 6 |
| | Component (BIII) | dimethylpolysiloxane (25° C. kinematic viscosity: 6 mm$^2$/sec) | 0 | 2 | 4 | 10 |

TABLE 19-continued

|  |  |  | Reference Example | Example | | Comparative Example |
|---|---|---|---|---|---|---|
|  |  |  | 4-3 | 4-7 | 4-8 | 4-5 |
|  | Component (D) | dodecamethylpentasiloxane | 94 | 92 | 90 | 84 |
|  | Total |  | 100 | 100 | 100 | 100 |
| Mass Ratio |(BIII)/(AI-3)| |  |  | 0 | 0.33 | 0.67 | 1.7 |
| Coating Amount of Component (AI-3) (mg/cm$^2$) |  |  | 0.12 | 0.12 | 0.12 | 0.12 |
| Evaluation | Adhesion Suppressing Ratio (%) |  | 90 | 76 | 73 | −22 |

TABLE 20

|  |  |  | Reference Example | Example | | | | Comparative Example | |
|---|---|---|---|---|---|---|---|---|---|
|  |  |  | 4-4 | 4-9 | 4-10 | 4-11 | 4-12 | 4-6 | 4-7 |
| Formulation of External Preparation (mass %) | Component (AI-3) | silicone-treated zinc oxide A3-2 | 6 | 6 | 6 | 6 | 6 | 6 | 6 |
|  | Component (BIII) | dimethylpolysiloxane (25° C. kinematic viscosity: 6 mm$^2$/sec) | 0 | 2.4 | 3 | 4 | 4.8 | 5.4 | 6.6 |
|  | Component (D) | dodecamethyl-pentasiloxane | 94 | 91.6 | 91 | 90 | 89.2 | 88.6 | 87.4 |
|  | Total |  | 100 | 100 | 100 | 100 | 100 | 100 | 100 |
| Mass Ratio [(BIII)/(AI-3)] |  |  | 0 | 0.40 | 0.50 | 0.67 | 0.80 | 0.90 | 1.1 |
| Coating Amount of Component (AI-3) (mg/cm$^2$) |  |  | 0.12 | 0.12 | 0.12 | 0.12 | 0.12 | 0.12 | 0.12 |
| Evaluation | Adhesion Suppressing Ratio (%) |  | 91 | 90 | 66 | 58 | 32 | −11 | −55 |

TABLE 21

|  |  |  | Comparative Example | |
|---|---|---|---|---|
|  |  |  | 4-8 | 4-9 |
| Formulation of External Preparation (mass %) | Component (AI') | methylsiloxane network polymer | 6 | 0 |
|  |  | silica particles | 0 | 6 |
|  | Component (BIII) | dimethylpolysiloxane (25° C. kinematic viscosity: 6 mm$^2$/sec) | 4.8 | 4.8 |
|  | Component (D) | dodecamethylpentasiloxane | 89.2 | 89.2 |
|  | Total |  | 100 | 100 |
| Mass Ratio ([BIII)/(AI')] |  |  | 0.80 | 0.80 |
| Coating Amount of Component (AI') (mg/cm$^2$) |  |  | 0.12 | 0.12 |
| Evaluation | Adhesion Suppressing Ratio (%) |  | −49 | −18 |

From Tables 17 to 21, it is known that, in Examples 4-1 to 4-12, the external preparation containing the component (AI) and component (BIII), in which the mass ratio of the component (BIII) to the component (AI) [(BIII)/(AI)] was 0.85 or less, was applied, and therefore, the samples have a higher adhesion suppressing effect as compared with those in Comparative Example 4-1 to 4-9.

In addition, as compared with those in Reference Examples 4-1 to 4-4, the external preparations in Examples 4-1 to 4-12 contain the component (BIII) and therefore give a good feel (touch) in use.

Examples 4-13 to 4-19

External preparations shown in the following Formulation Examples 4-1 to 4-7 were prepared and evaluated in the same manner as in the evaluation method (2) for the adhesion suppressing effect against air harmful substances mentioned above, except that each preparation was applied to a white artificial leather in an amount of 2 mg/cm$^2$. The results are shown in Table 22.

Expressions *1 to *28, *33 and *36 in the formulation examples are the same as above.

Formulation Example 4-1 (W/O type external preparation, mass ratio [(CIII-1)/(AI)] = 0.31, mass ratio [(CIII-2)/(AI)] = 0.35, mass ratio [(BIII)/(AI)] = 0.04) (Blending Components (amount))

| Stearic acid-treated titanium oxide (component (AI-1))*1 | 7 parts |
|---|---|
| Silicone-treated zinc oxide (component (AI-3))*2 | 19 parts |
| Neopentyl glycol dicaprylate (component (CIII-1))*3 | 3 parts |
| Glyceryl tri-2-ethylhexanoate (component (CIII-1))*12 | 5 parts |
| Liquid isoparaffin (component (CIII-2))*4 | 5 parts |

Formulation Example 4-1 (W/O type external preparation, mass ratio [(CIII-1)/(AI)] = 0.31, mass ratio [(CIII-2)/(AI)] = 0.35, mass ratio [(BIII)/(AI)] = 0.04) (Blending Components (amount))

| | |
|---|---|
| Squalane (component (CIII-2))*5 | 4 parts |
| Dimethylpolysiloxane (25° C. kinematic viscosity: 10 mm²/s) (component (BIIN*6 | 1 part |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm²/s) (component (D))*9 | 35.1 parts |
| Methylsiloxane network polymer*10 | 3 parts |
| Silicone-coated talc*11 | 1.9 parts |
| Glycerin (86%) | 1 part |
| Pure water | balance |
| Total | 100 parts |

Formulation Example 4-2 (W/O type external preparation) (mass ratio [(CIII-1)/(AI)] = 0.12, mass ratio ([CIII-2)/(AI)] = 0.35, mass ratio [(BIII)/(AI)] = 0.23) (Blending Components (amount))

| | |
|---|---|
| Stearic acid-treated titanium oxide (component (AI-1))*1 | 7 parts |
| Silicone-treated zinc oxide (component (AI-3))*2 | 19 parts |
| Neopentyl glycol dicaprylate (component (CIII-1))*3 | 3 parts |
| Liquid isoparaffin (component (CIII-2))*4 | 7 parts |
| Squalane (component (CIII-2))*5 | 2 parts |
| Dimethylpolysiloxane (25° C. kinematic viscosity: 10 mm²/s) (component BIII))*6 | 1 part |
| Dimethylpolysiloxane (25° C. kinematic viscosity: 6 mm²/s) (component BIII))*13 | 5 parts |
| N-(hexadecyloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm²/s) (component (D))*9 | 35.1 parts |
| Glycerin (86%) | 1 part |
| Pure water | balance |
| Total | 100 parts |

Formulation Example 4-3 (W/O type external preparation) (mass ratio [(CIII-1)/(AI)] = 0.97, mass ratio [(BIII)/(AI)] = 0.27) (Blending Components (amount))

| | |
|---|---|
| Octyltriethoxysilane-treated zinc oxide (component (AI-2))*14 | 15 parts |
| 2-Ethylhexyl paramethoxycinnamate (component (CIII-1))*15 | 10 parts |
| Neopentyl glycol dicaprylate (component (CIII-1))*3 | 3 parts |
| Isopropyl palmitate (component (CIII-1))*17 | 1.5 parts |
| Dimethylpolysiloxane (25° C. kinematic viscosity: 6 mm²/s) (component BIII))*13 | 4 parts |
| 2,4-Bis-[{4-(2-ethylhexyloxy)-2-hydroxy}-phenyl]-6-(4-methoxyphenyl)-1,3,5-triazine*16 | 2 parts |
| Polyoxyethylene/methylpolysiloxane copolymer (HLB: 4.5)*8 | 0.8 parts |
| Dodecamethylpentasiloxane (25° C. kinematic viscosity: 2 mm²/s) (component (D))*9 | 5 parts |

Formulation Example 4-3 (W/O type external preparation) (mass ratio [(CIII-1)/(AI)] = 0.97, mass ratio [(BIII)/(AI)] = 0.27) (Blending Components (amount))

| | |
|---|---|
| Decamethylcyclopentasiloxane (25° C. kinematic viscosity: 4 mm²/s) (component D))*18 | 28.7 parts |
| Silicone-coated talc*11 | 2 parts |
| Ethanol | 11 parts |
| 1,3-Butylene glycol | 2 parts |
| Pure water | balance |
| Total | 100 parts |

Formulation Example 4-4 (W/O type external preparation, mass ratio [(CIII-2)/(AI)] = 0.41, mass ratio [(BIII)/(AI)] = 0.14) (Blending Components (amount))

| | |
|---|---|
| Stearic acid-treated titanium oxide (component (AI-1))*1 | 10 parts |
| Silicone-treated zinc oxide (component (AI-3))*2 | 19 parts |
| Liquid isoparaffin (component (CIII-2))*4 | 10 parts |
| Squalane (component (CIII-2))*5 | 2 parts |
| Dimethylpolysiloxane (25° C. kinematic viscosity: 10 mm²/s) (component (BIII))*6 | 1 part |
| Dimethylpolysiloxane (25° C. kinematic viscosity: 6 mm²/s) (component (BIII))*13 | 3 parts |
| N-(hexadesiloxyhydroxypropyl)-N-hydroxyethylhexadecanamide*7 | 1.5 parts |
| Polyoxyethylene/methylpolysiloxane copolymer (HLB: 4.5)*8 | 1.4 parts |
| Dodecamethylpentasiloxane (25° C. kinematic viscosity: 2 mm²/s) (component (D))*9 | 35.1 parts |
| Glycerin (86%) | 1 part |
| Pure water | balance |
| Total | 100 parts |

Formulation Example 4-5 (O/W type external preparation, mass ratio [(CIII-1)/(AI)] = 3.0, mass ratio [(BIII)/(AI)] = 0.25) (Blending Components (amount))

| | |
|---|---|
| Stearic acid-treated titanium oxide (component (AI-1))*19 | 4 parts |
| Isopropyl palmitate (component (CIII-1))*17 | 4 parts |
| 2-Ethylhexyl paramethoxycinnamate (component (CIII-1))*15 | 8 parts |
| Dimethylpolysiloxane (25° C. kinematic viscosity: 10 mm²/s) (component BIII))*6 | 1 part |
| 2,4-Bis-[{4-(2-ethylhexyloxy)-2-hydroxy}-phenyl]-6-(4-methoxyphenyl)-1,3,5-triazine*16 | 1 part |
| Cetanol*20 | 0.2 parts |
| Glyceryl monostearate*21 | 0.3 parts |
| Isoceteth-20*22 | 0.03 parts |
| Acrylates/C10-30 alkyl acrylate cross polymer*23 | 0.2 parts |
| Acrylates/C10-30 alkyl acrylate cross polymer*24 | 0.2 parts |
| EDTA-2Na | 0.01 parts |
| Phenoxyethanol | 0.5 parts |
| Potassium hydroxide (48%) | 0.4 parts |
| Ethanol | 5 parts |
| Pure water | balance |
| Total | 100 parts |

Formulation Example 4-6 (O/W type external preparation, mass ratio [(CIII-1)/(AI)] = 3.5, mass ratio [(BIII)/(AI)] = 0.25) (Blending Components (amount))

| | |
|---|---|
| Octyltriethoxysilane-treated titanium oxide (component (AI-2))*25 | 4 parts |
| Isopropyl palmitate (component (CIII-1))*17 | 4 parts |
| 2-Ethylhexyl paramethoxycinnamate (component (CIII-1))*15 | 8 parts |
| 2,4,6-Tris[4-(2-ethylhexyloxycarbonyl)anilino-1,3,5-triazine(component (CIII-1))*26 | 2 parts |
| Dimethylpolysiloxane (25° C. kinematic viscosity: 10 mm$^2$/s) (component BIII))*6 | 1 part |
| 2,4-Bis-[{4-(2-ethylhexyloxy)-2-hydroxy}-phenyl]-6-(4-methoxyphenyl)-1,3,5-triazine*16 | 2 parts |
| Cetanol*20 | 0.2 parts |
| Glyceryl monostearate*21 | 0.3 parts |
| Isoceteth-20*22 | 0.03 parts |
| Polyoxyethylene sorbitan monostearate*27 | 0.1 parts |
| Acrylates/C10-30 alkyl acrylate cross polymer*23 | 0.2 parts |
| Acrylates/C10-30 alkyl acrylate cross polymer*24 | 0.2 parts |
| Light liquid isoparaffin (component (D))*28 | 1 part |
| EDTA-2Na | 0.01 parts |
| Phenoxyethanol | 0.5 parts |
| 1,3-Butylene glycol | 5 parts |
| Potassium hydroxide (48%) | 0.6 parts |
| Ethanol | 5 parts |
| Pure water | balance |
| Total | 100 parts |

Formulation Example 4-7 (O/W type external preparation, mass ratio [(CIII-1)/(AI)] = 1.5, mass ratio [(BIII)/(AI)] = 0.50) (Blending Components (amount))

| | |
|---|---|
| Stearic acid-treated titanium oxide (component (AI-1))*19 | 8 parts |
| Isononyl isononanoate (component (CIII-1))*36 | 7.6 parts |
| Neopentyl glycol dicaprylate (component (CIII-1))*3 | 4 parts |
| Dimethylpolysiloxane (25° C. kinematic viscosity: 6 mm$^2$/s) (component (BIII))*13 | 4 parts |
| Sorbitan monostearate*33 | 0.7 parts |
| Polyoxyethylene sorbitan monostearate*27 | 1 part |
| Stearyl alcohol | 1 part |
| Acrylates/C10-30 alkyl acrylate cross polymer*23 | 0.07 parts |
| Acrylates/C10-30 alkyl acrylate cross polymer*24 | 0.25 parts |
| Potassium hydroxide (48%) | 0.4 parts |
| 1,3-Butylene glycol | 8 parts |
| EDTA-2Na | 0.02 parts |
| Pure water | balance |
| Total | 100 parts |

From Table 22, it is known that, in Examples 4-13 to 4-19, the external preparation of Formulation Examples 4-1 to 4-7 was applied, and therefore the samples have an adhesion suppressing effect.

In addition, as compared with those in Reference Examples 4-1 to 4-4, the external preparations in Examples 4-13 to 4-19 contain the component (BIII) and therefore give a good feel (touch) in use.

INDUSTRIAL APPLICABILITY

The adhesion suppressing method of the present invention provides a high adhesion suppressing effect against air harmful substances, and is therefore especially useful as a method of suppressing adhesion of air harmful substances to skin.

REFERENCE SIGNS LIST

1: Sample Targeted for Evaluation
2: Support
3: Wire Sieve
4: Air harmful substances for Evaluation
5: Fan

The invention claimed is:

1. A method for suppressing adhesion of air harmful substances, the method comprising applying an external preparation to skin to suppress adhesion of air pollutants to the skin, wherein:
    the external preparation comprises the following component (AI) and one of components (BI), (BII), or (BIII), and
    the ratio by mass of the content of the component (BI), if present, to the content of the component (AI) in the external preparation [(BI)/(AI)] is 9 or less;
    the ratio by mass of the content of the component (BII), if present, to the content of the component (AI) in the external preparation [(BII)/(AI)] is 3.5 or less; and
    the ratio by mass of the content of the component (BIII), if present, to the content of the component (AI) in the external preparation [(BIII)/(AI)] is 0.85 or less:
    Component (AI): a hydrophobized metal oxide having an average primary particle diameter $d_{AI}$ of 5 nm or more and 700 nm or less,
    Component (BI): an ester oil,
    Component (BII): a nonvolatile hydrocarbon oil,
    Component (BIII): a nonvolatile silicone oil, and

TABLE 22

| | | Example | | | | | | |
|---|---|---|---|---|---|---|---|---|
| | | 4-13 | 4-14 | 4-15 | 4-16 | 4-17 | 4-18 | 4-19 |
| Formulation of External Preparation (mass %) | Formulation Example of External Preparation | 4-1 | 4-2 | 4-3 | 4-4 | 4-5 | 4-6 | 4-7 |
| | Component (AI) | 26 | 26 | 15 | 29 | 4 | 4 | 8 |
| | Component (BIII) | 1 | 6 | 4 | 4 | 1 | 1 | 4 |
| Mass Ratio [(BIII)/(AI)] in external preparation | | 0.04 | 0.23 | 0.27 | 0.14 | 0.25 | 0.25 | 0.50 |
| Coating Amount of Component (AI) (mg/cm$^2$) | | 0.52 | 0.52 | 0.30 | 0.58 | 0.08 | 0.08 | 0.16 |
| Evaluation | Adhesion Suppressing Ratio (%) | 70 | 33 | 60 | 61 | 67 | 67 | 51 | said metal oxide (AI) is applied to said skin in an amount of 0.03 mg/cm$^2$ or more and 0.8 mg/cm$^2$ or less.

2. The method for suppressing adhesion of air harmful substances according to claim 1, wherein the metal oxide of the component (AI) is at least one selected from the group consisting of titanium oxide and zinc oxide.

3. The method for suppressing adhesion of air harmful substances according to claim 1, wherein the content of the component (AI) in the external preparation is 1% by mass or more and 40% by mass or less.

4. The method for suppressing adhesion of air harmful substances according to claim 1, wherein the average primary particle diameter $d_{AI}$ of the component (AI) is 5 nm or more.

5. The method for suppressing adhesion of air harmful substances according to claim 1, wherein the component (AI) is at least one selected from the group consisting of the following component (AI-1), component (AI-2) and component (AI-3):

Component (AI-1): a fatty acid-treated metal oxide having an average primary particle diameter $d_{AI}$ of 800 nm or less, Component (AI-2): an alkylalkoxysilane-treated metal oxide having an average primary particle diameter $d_{AI}$ of 800 nm or less, Component (AI-3): a silicone-treated metal oxide having an average primary particle diameter $d_{AI}$ of 800 nm or less.

6. The method for suppressing adhesion of air harmful substances according to claim 5, wherein the ratio by mass of the content of the component (BI) to the total content of the component (AI-1), the component (AI-2) and the component (AI-3) in the external preparation, [(BI)/[(AI-1)+ (AI-2)+ (AI-3)]] is 9 or less.

7. The method for suppressing adhesion of air harmful substances according to claim 5, wherein the ratio by mass of the content of the component (BII) to the total content of the component (AI-1), the component (AI-2) and the component (AI-3) in the external preparation, [(BII)/[(AI-1)+ (AI-2)+ (AI-3)]] is 3.5 or less.

8. The method for suppressing adhesion of air harmful substances according to claim 5, wherein the ratio by mass of the content of the component (BIII) to the total content of the component (AI-1), the component (AI-2) and the component (AI-3) in the external preparation, [(BIII)/[(AI-1)+ (AI-2)+ (AI-3)]] is 0.85 or less.

9. The method for suppressing adhesion of air harmful substances according to claim 5, wherein the total content of the component (AI-1), the component (AI-2) and the component (AI-3) in the external preparation is 1% by mass or more and 40% by mass or less.

10. The method for suppressing adhesion of air harmful substances according to claim 5, wherein the metal oxide of the component (AI-1), the component (AI-2) and the component (AI-3) is at least one selected from the group consisting of titanium oxide and zinc oxide.

11. The method for suppressing adhesion of air harmful substances according to claim 1, wherein said hydrophobized metal oxide having an average primary particle diameter $d_{AI}$ of 15 nm or more and 700 nm or less.

12. The method for suppressing adhesion of air harmful substances according to claim 1, wherein said hydrophobized metal oxide having an average primary particle diameter $d_{AI}$ of 20 nm or more and 700 nm or less.

13. A method for suppressing adhesion of air harmful substances, the method comprising applying a metal oxide (A) having an average primary particle diameter $d_A$ of 5 nm or more and 700 nm or less to skin in an amount of 0.03 mg/cm$^2$ or more and 0.8 mg/cm$^2$ or less to suppress adhesion of air pollutants to the skin.

14. The method for suppressing adhesion of air harmful substances according to claim 13, wherein the metal oxide (A) is at least one selected from the group consisting of titanium oxide and zinc oxide.

15. The method for suppressing adhesion of air harmful substances according to claim 14, wherein the metal oxide (A) is one hydrophobized or hydrophilized on the surface thereof.

16. The method for suppressing adhesion of air harmful substances according to claim 15, wherein said hydrophobized metal oxide having an average primary particle diameter $d_{AI}$ of 15 nm or more and 700 nm or less.

17. The method for suppressing adhesion of air harmful substances according to claim 16, wherein said hydrophobized metal oxide having an average primary particle diameter $d_{AI}$ of 20 nm or more and 700 nm or less.

* * * * *